United States Patent
Chou et al.

(10) Patent No.: US 12,066,434 B2
(45) Date of Patent: *Aug. 20, 2024

(54) QMAX ASSAYS AND APPLICATIONS

(71) Applicant: Essenlix Corporation, Monmouth Junction, NJ (US)

(72) Inventors: Stephen Y. Chou, Princeton, NJ (US); Wei Ding, East Windsor, NJ (US); Yufan Zhang, Monmouth Junction, NJ (US); Ji Qi, Hillsborough, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 857 days.

This patent is subject to a terminal disclaimer.

(21) Appl. No.: 16/484,678

(22) PCT Filed: Feb. 8, 2018

(86) PCT No.: PCT/US2018/017499
§ 371 (c)(1),
(2) Date: Aug. 8, 2019

(87) PCT Pub. No.: WO2018/152005
PCT Pub. Date: Aug. 23, 2018

(65) Prior Publication Data
US 2020/0319176 A1    Oct. 8, 2020

Related U.S. Application Data

(60) Provisional application No. 62/456,528, filed on Feb. 8, 2017, provisional application No. 62/456,537, filed
(Continued)

(51) Int. Cl.
*G01N 33/543*   (2006.01)
*G01N 1/40*   (2006.01)
(Continued)

(52) U.S. Cl.
CPC ....... *G01N 33/54366* (2013.01); *G01N 1/405* (2013.01); *G01N 21/648* (2013.01);
(Continued)

(58) Field of Classification Search
CPC ....... G01N 33/54313; G01N 33/54386; G01N 33/54393; G01N 33/543; G01N 2470/10;
(Continued)

(56) References Cited

U.S. PATENT DOCUMENTS 3,368,872 A    2/1968  Natelson
3,447,863 A    6/1969  Patterson
(Continued)

FOREIGN PATENT DOCUMENTS

AU    198813789 A    9/1988
AU       619459 B    1/1992
(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.
(Continued)

*Primary Examiner* — Christopher L Chin

(57) ABSTRACT

The present invention provides, among other things, QMAX card based assays in different forms for various analytes, offering simpler, fast, more sensitive assaying.

46 Claims, 23 Drawing Sheets

Related U.S. Application Data on Feb. 8, 2017, provisional application No. 62/456,631, filed on Feb. 8, 2017, provisional application No. 62/456,628, filed on Feb. 8, 2017, provisional application No. 62/456,585, filed on Feb. 8, 2017.

(51) Int. Cl.
  *G01N 21/64* (2006.01)
  *G01N 21/65* (2006.01)
  *G01N 21/69* (2006.01)
  *G01N 21/76* (2006.01)
  *G01N 33/558* (2006.01)

(52) U.S. Cl.
  CPC ............ *G01N 21/65* (2013.01); *G01N 21/69* (2013.01); *G01N 21/76* (2013.01); *G01N 33/558* (2013.01)

(58) Field of Classification Search
  CPC .............. C12Q 1/6804; C12Q 1/6869; C12Q 1/6837; C12Q 2537/125; C12Q 2537/1373; C12Q 2537/161; C12Q 2563/149; C12Q 2565/601; G06K 9/00134; G06K 9/00147
  USPC ........ 356/244, 246; 422/401, 408, 425, 436, 422/551, 561, 563; 435/7.93, 288.3, 435/288.7, 40.5, 40.52, 165; 436/805, 436/807
  See application file for complete search history.

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A * | 5/1977 | Hall ...................... G02B 21/34 359/398 |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,027,944 A * | 2/2000 | Robinson .......... G01N 33/54366 435/7.1 |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 * | 8/2002 | Chee ................. G01N 33/54393 977/924 |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,713,703 B1 * | 5/2010 | Buechler .......... G01N 33/54386 435/7.1 |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |

(56) References Cited

U.S. PATENT DOCUMENTS

| | | |
|---|---|---|
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1* | 10/2004 | Parker .................... B01L 3/508 435/288.3 |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0092389 A1 | 4/2011 | Dickinson et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0280752 A1* | 10/2013 | Ozcan ................ G01B 9/02041 356/482 |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2014/0370616 A1* | 12/2014 | Gupta .................... G01N 33/82 422/69 |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1* | 2/2016 | Chou ................ G01N 33/54386 422/69 |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| JP | 2010190880 A | 9/2010 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |

(56) References Cited

FOREIGN PATENT DOCUMENTS

| | | |
|---|---|---|
| WO | 2014205576 | 12/2014 |
| WO | 2017048871 | 3/2017 |

OTHER PUBLICATIONS

Written Opinion for PCT/US2018/017713 established by ISA/KR, dated Jun. 20, 2018.

* cited by examiner (i)

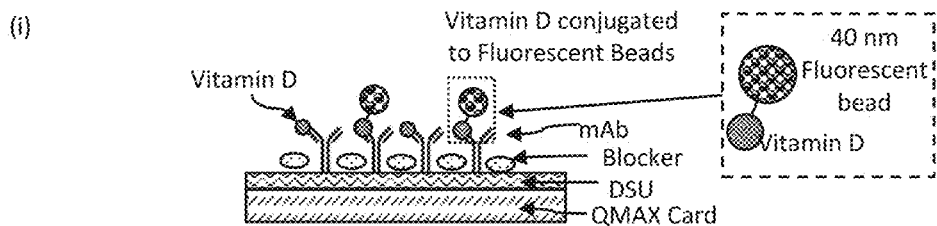

(ii)

| Material/Reagent | Concentration | Condition |
|---|---|---|
| Molecule Adhesion Layer (DSU) | 0.5 mM | Bound to QMAX card's Metal surface |
| Mouse anti-25OH mAb | 1 pM ~ 1000 nM (prefer 300 pM) | Chemically Bonded to DSU via Fc region |
| Sample | 0 nM ~ 375 nM | serum |
| Releasing Reagent (PFOA) | 0.01% ~ 5% (prefer 0.5%) | Drop dried on top of second plate |
| Vitamin D conjugated to fluorescent beads | 1 pM ~ 1000 nM (prefer 200 nM) | Drop dried on top of second plate |

(iii)

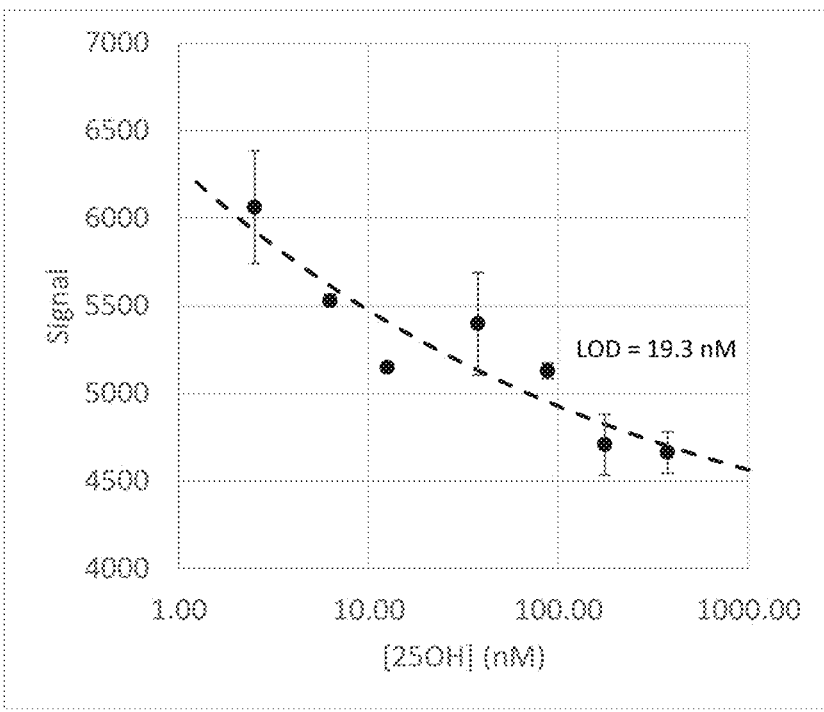

Fig. 3

A
Perspective view    Cross-sectional view
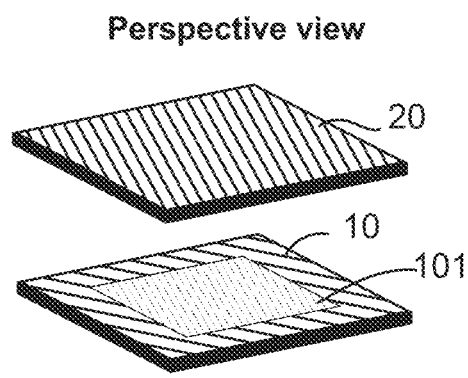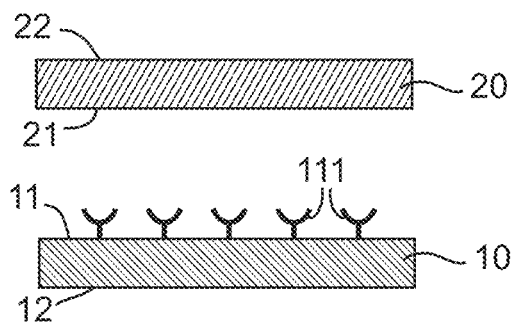
B
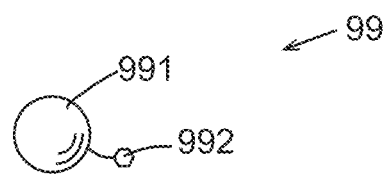
C
Perspective view    Cross-sectional view
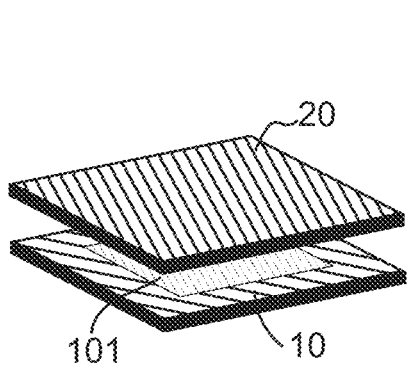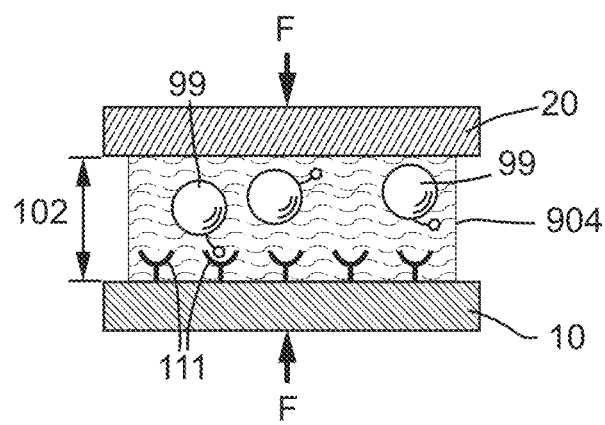
Fig. 4

A
Perspective view
Cross-sectional view
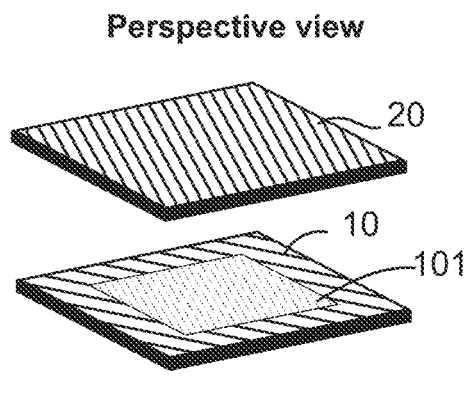
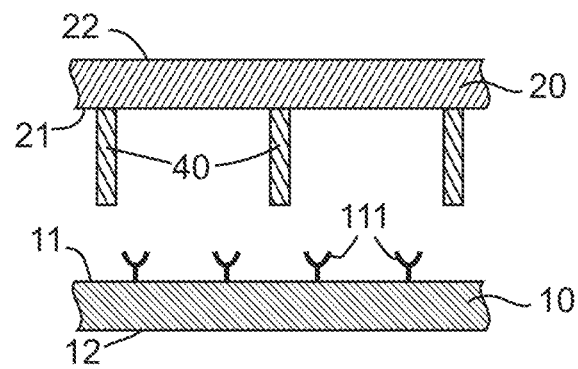
B
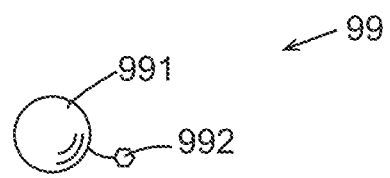
C
Perspective view
Cross-sectional view
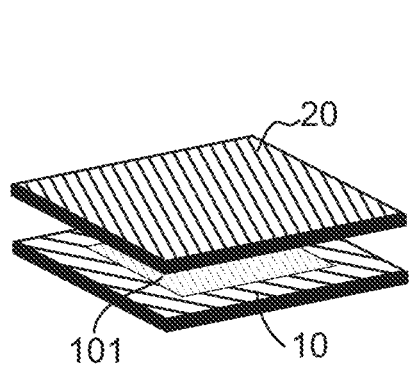
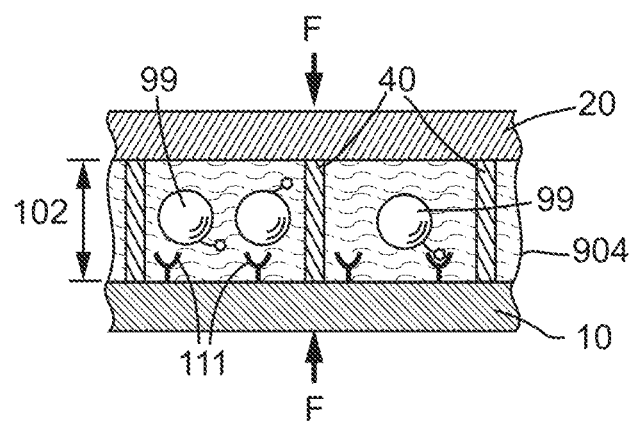
Fig. 6

Provide a first plate 10, second plate 20, a spacing mechanism, and at least one nanoparticle label 99.

Add the nanoparticle label 99 into a liquid sample to form a label solution.

Deposit the label solution on the inner surface of at least one of the two plates when the two plates are configured in the open configuration.

Compress the deposited label solution by bringing the two plates into the closed configuration, in which the thickness of a relevant volume of the deposited label solution is reduced into a layer of reduced thickness.

Fig. 7

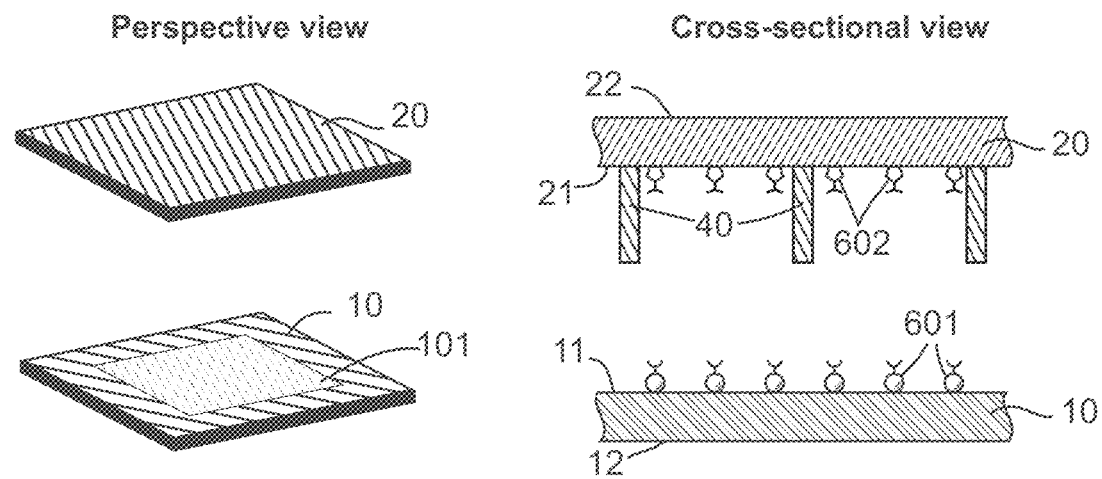
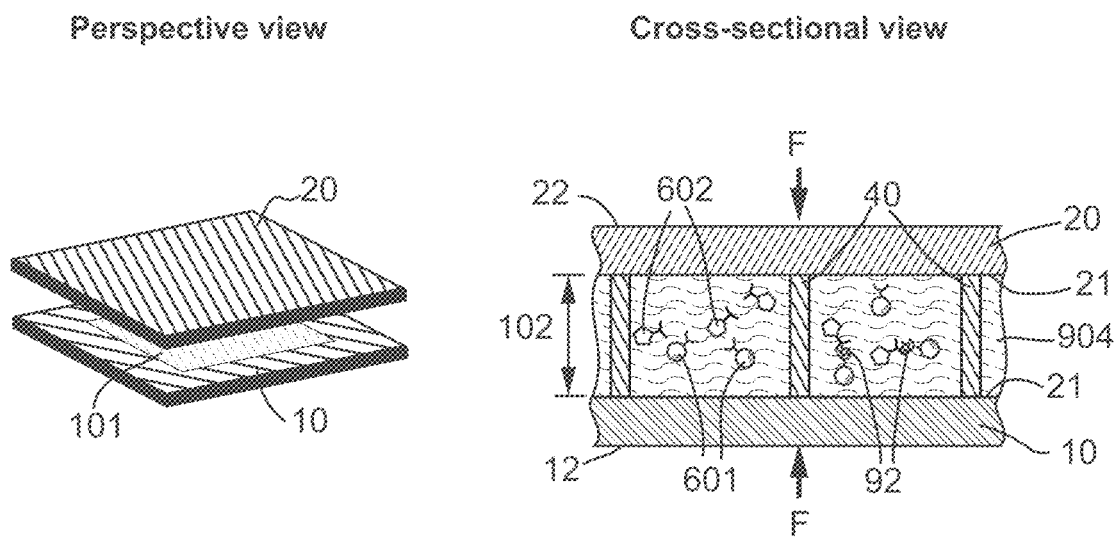
Fig. 21

Provide a first plate 10, second plate 20, a spacing mechanism, one first bead 601 and one second bead 602.

Deposit a sample 90 containing a target analyte 92 on the inner surface of at least one of the two plates when the two plates are configured in the open configuration.

Compress the deposited sample by bringing the two plates into the closed configuration, in which the thickness of a relevant volume of the deposited sample is reduced into a layer of reduced thickness 904.

Fig. 22

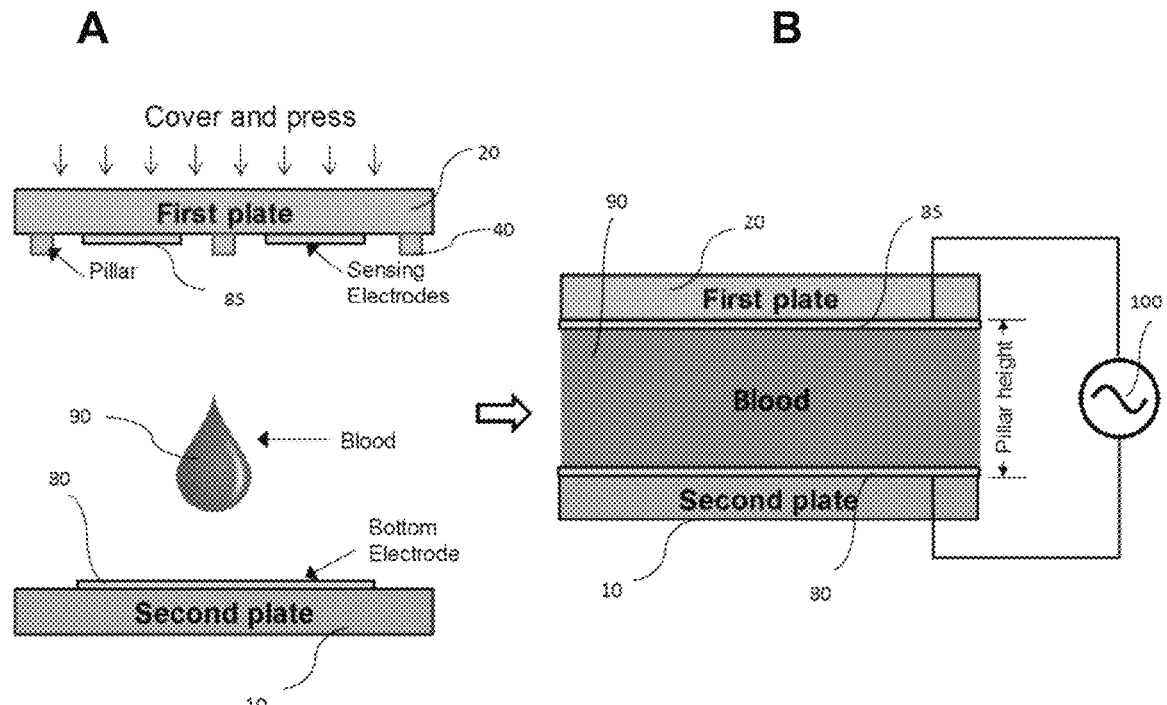

Fig. 23 ized Patent Application U.S. Ser. No. 62/456,628, filed on

QMAX ASSAYS AND APPLICATIONS

CROSS-REFERENCE TO RELATED APPLICATIONS

This application is a § 371 national stage application of International Application PCT/US2018/017499 filed on Feb. 8, 2018, which claims the benefit of priority to U.S. Provisional Patent Application U.S. Ser. No. 62/456,628, filed on Feb. 8, 2017, U.S. Provisional Patent Application U.S. Ser. No. 62/456,631, filed on Feb. 8, 2017, U.S. Provisional Patent Application U.S. Ser. No. 62/456,528, filed on Feb. 8, 2017, U.S. Provisional Patent Application U.S. Ser. No. 62/456,537, filed on Feb. 8, 2017, and U.S. Provisional Patent Application U.S. Ser. No. 62/456,585, filed on Feb. 8, 2017, the contents of which are relied upon and incorporated herein by reference in their entirety. The entire disclosure of any publication or patent document mentioned herein is entirely incorporated by reference.

FIELD

Among other things, the present invention is related to the field of bio/chemical sampling, sensing, assays and other applications. Particularly, the present invention is related to how to perform a bio/chemical assay using nanoparticle labels.

BACKGROUND

In biological and chemical assays (e.g. diagnostic testing), nanoparticle labels are used for assaying, where the nanoparticle label is configured to bind to other binding entities (e.g. target analyte and binding agent) and provide a detectable signal that is related to the binding. However, the binding time is typically in the range of 30 mins to hours. The present invention provides the devices and methods that can reduce the binding time into a few minutes or even less than 60 sec.

Among other things, the present invention relates to competitive assays. In some embodiments, the device and method herein disclosed can be used to detect and/or measure vitamin D. Vitamin D is the active form of which plays a role in the formation and maintenance of bone, as well as in other processes in the human or animal body. In clinical practice, the serum level of 25-hydroxy-vitamin D (25OH Vitamin D) is the primary indicator of the vitamin D status. Traditional Vitamin D assays (e.g. 25-OH competitive immunoasssay), require relatively large volume of sample (>20 uL) and sample pre-treatment to release the 25OH Vitamin D before being tested in immunoassay. It is complex, time-consuming, laborious and require lab setups and significant amount of consumable lab materials. It is desirable to develop a device and method that can measure the 25OH Vitamin D in the sample, quickly and simply, and can be conducted by a non-professional. The current invention provides devices and methods for achieving these goals.

BRIEF DESCRIPTION OF THE DRAWINGS

The skilled artisan will understand that the drawings, described below, are for illustration purposes only. The drawings are not intended to limit the scope of the present teachings in any way. The drawings not are not entirely in scale. In the figures that present experimental data points, the lines that connect the data points are for guiding a viewing of the data only and have no other means.

In FIG. 1 the QMAX device is in an open configuration.

In FIG. 2 (iv) and (v) the QMAX device is in a closed configuration FIG. 3 shows an example of a standard curve of a A Vitamin D Assay performed on QMAX card with Au surface and uses 40 nm fluorescent beads as label.

FIG. 4 shows an exemplary embodiment of a device for analyzing a liquid sample provided by the present invention. Panel (A) shows a prospective view of a first plate and a second plate; panel (B) shows a nanoparticle label; panel (C) shows using the first plate and the second plate to compress the sample into a thin layer, and in which the nanoparticle label binds to the binding agent on the first plate directly.

FIG. 6 shows another exemplary embodiment of a device for analyzing a liquid sample provided by the present invention. Panel (A) shows a prospective view of a first plate, a second plate and spacers; panel (B) shows a nanoparticle label; panel (C) shows using the first plate and the second plate to compress the sample into a layer of uniform thickness, which is regulated by the height of the spacers, and in which the nanoparticle label binds to the binding agent on the first plate directly.

FIG. 7 is a flow chart of an exemplary embodiment of a method of analyzing a liquid sample using nanoparticle labels.

FIG. 21 shows another exemplary embodiment of a device for analyzing a liquid sample provided by the present invention.

FIG. 22 is a flow chart of an exemplary embodiment of a method of analyzing a liquid sample provided by the present invention.

FIG. 23 is a schematic drawing for an exemplary embodiment of a QMAX (Q: quantification; M: magnifying; A: adding reagents; X: acceleration; also known as compressed regulated open flow (CROF)) device that employs electrodes for electro-detection. In some embodiments, electrical measurement can be used to measure sample permittivity, which can in turn serve as the basis for assessment of blood coagulation.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

A. Competitive Assay of Vitamin D (042)

Figure 1:
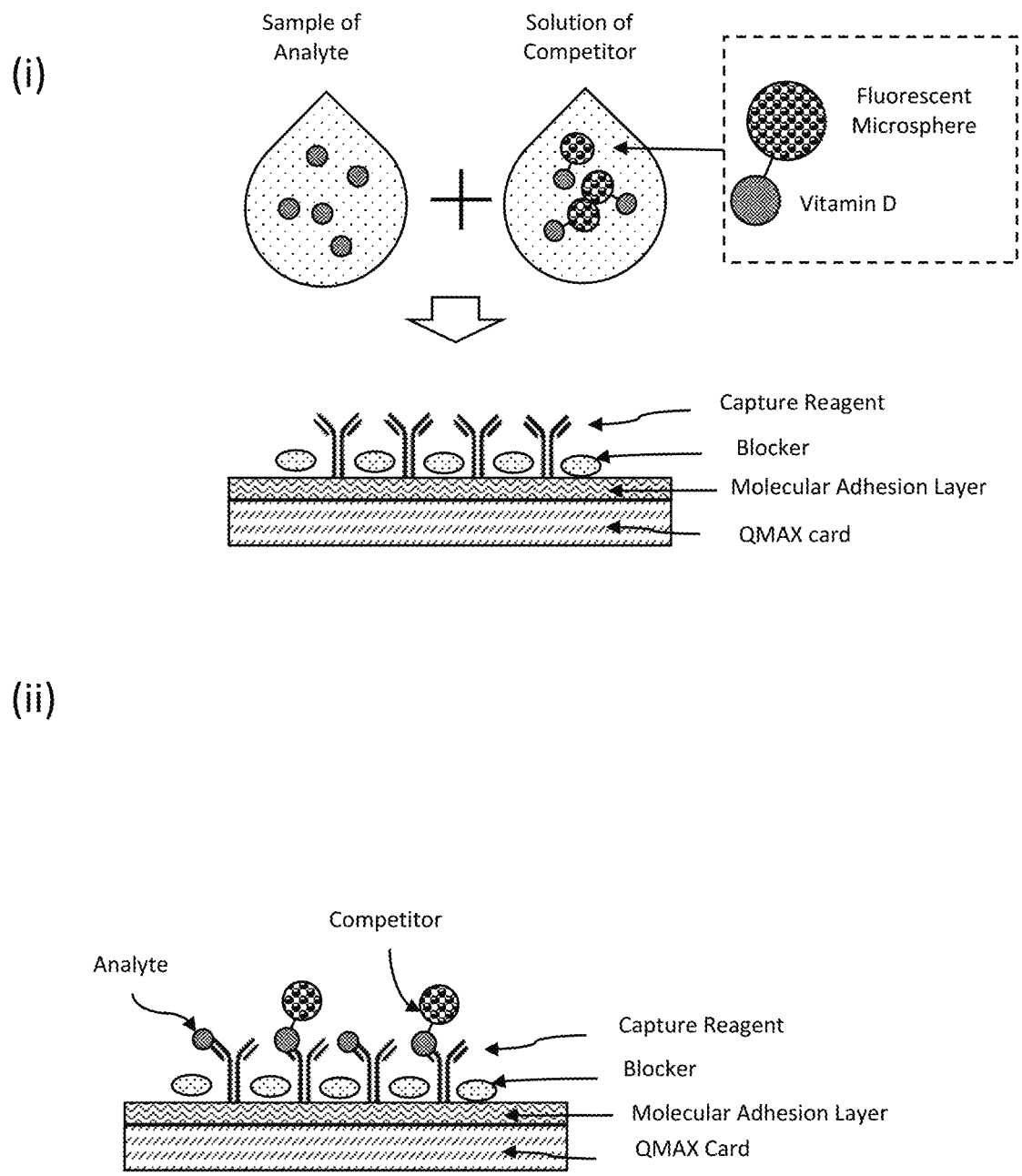
FIG. 1 is a schematic drawing of a Vitamin D competitive Assay on a QMAX card. (Q: quantification; M: magnifying; A: adding reagents; X: acceleration; also known as compressed regulated open flow (CROF)) device that can be used for an immunoassay.

As Shown in FIG. 1, on the solid surface, capture reagent that can specifically capture of Vitamin D is immobilized via bio/chemical binding. The capture reagent can be anti-VD antibody, or a VD binding protein.

As shown in FIG. 1, in some embodiments the first plate comprises a capture antibody that is coated on the inner surface of the first plate. In some embodiments, the capture antibody can be applied to the surface by printing, spraying, soaking or any other method that applies homogenous layer of reagents. In certain embodiments, the capture antibody is dried on the first plate. In some embodiments, the capture antibody is either monocolonal, polyclonal antibody, engineered antibody (e.g. single chain variable fragments (scFv)) or fragments thereof. In some embodiments, the concentration of coated capture antibody ranges from 1 fg/mL to 1 g/mL.

As shown in FIG. 1, the bio/chemical binding can be a self-assembled monolayer, or polymer layers thereof, with molecule adhesion layer that has function groups whose one end with bind the capture reagent and the other bind to the surface of the first plate.

As shown in FIG. 1, after blocking and stabilizing the capture reagent, Sample that contains analyte is directly dropped on the prepared first plate, then followed by adding the competitor is Vitamin-D conjugated to labels. The sample can be any liquid that needs testing. In some embodiments, the sample is a body fluid that is with or without processing or dilution. For example, the body fluid can be whole blood, blood plasma, serum, urine, saliva, sweat, or breath condensate. In some embodiments, the sample is blood. In certain embodiments, the sample comprises plasma. In certain embodiments, the sample comprises whole blood. In certain embodiments, the sample is a blood or plasma that has been diluted with buffer 0.5, 1, 2, 3, 4, 5, 6, 7, 8, 9, 10, 20, 30, 40, 50, 60, 70, 80, 90, 100, 200, 300, 400, 500, 600, 700, 800, 900, 1,000, 5,000, 10,000, 50,000, 100,000, 500,000, or 1,000,000 times or in a range between any of the two values.

As shown in FIG. 1, in some embodiments the first plate comprises blockers that are coated on the inner surface of the first plate. In some embodiments, the blockers block any unoccupied sites on the solid surface that can cause unwanted nonspecific bindings in assays. In certain embodiments, the blocker reduces nonspecific binding. In certain embodiments, the blockers can be applied to the surface by printing, spraying, soaking or any other method that applies homogenous layer of reagents. In some embodiments, the blockers are bovine serum albumin (BSA), casein or total proteins from whole milk, etc. In certain embodiments, the concentration of blocker ranges from 0.1% to 10% (w/v).

As shown in FIG. 1, The competitor is the bio/chemical conjugation of 25OH Vitamin D with a label. The label is fluorescent. In certain embodiment, the label is fluorescent particles with diameter of 10, 20, 30, 40, 50, 60, 70, 80, 90, 100, 200, 500, 1000, 2000 nanometers or in a range between any of the two values. In certain embodiment, the label is fluorescent protein, i.e. R-phycoerythrin. In certain embodiment, the label is quantum dot, i.e. CdSe, CdS. In certain embodiment, the label is enzyme that react with a fluorescent substrate, i.e. Horseradish peroxidase (HRP).

The competitor is used to compete with analyte in samples for the capture agent immobilized on QMAX card. The competitor's signal is used to correlate to the amount of analyte bound to capture agent. For example, in some embodiments of the present invention, the more analyte in the sample, the less the competitor with label is bound by capture agent, thus lower signal is detectable. In some embodiments of the present invention, the less analyte in the sample, the more the competitor with label is bound by capture agent, thus higher signal is detectable. The level of signal from detectable competitive agent is correlated with the amount of analyte bound by the capture agent.

As shown in FIG. 1, the analyte in sample and competitor with label is mixed. Once they are in contact with each other, they start mixing by diffusion. During the incubation, the Vitamin D in the sample and the competitor will compete for the limited capture reagent on the first plate. The more analyte (without label) bound to capture agent, the less competitive agent (with label) bound to capture agent. Therefore, The higher the concentration of Vitamin D analyte, the lower the signal can be measured.

Figure 2:
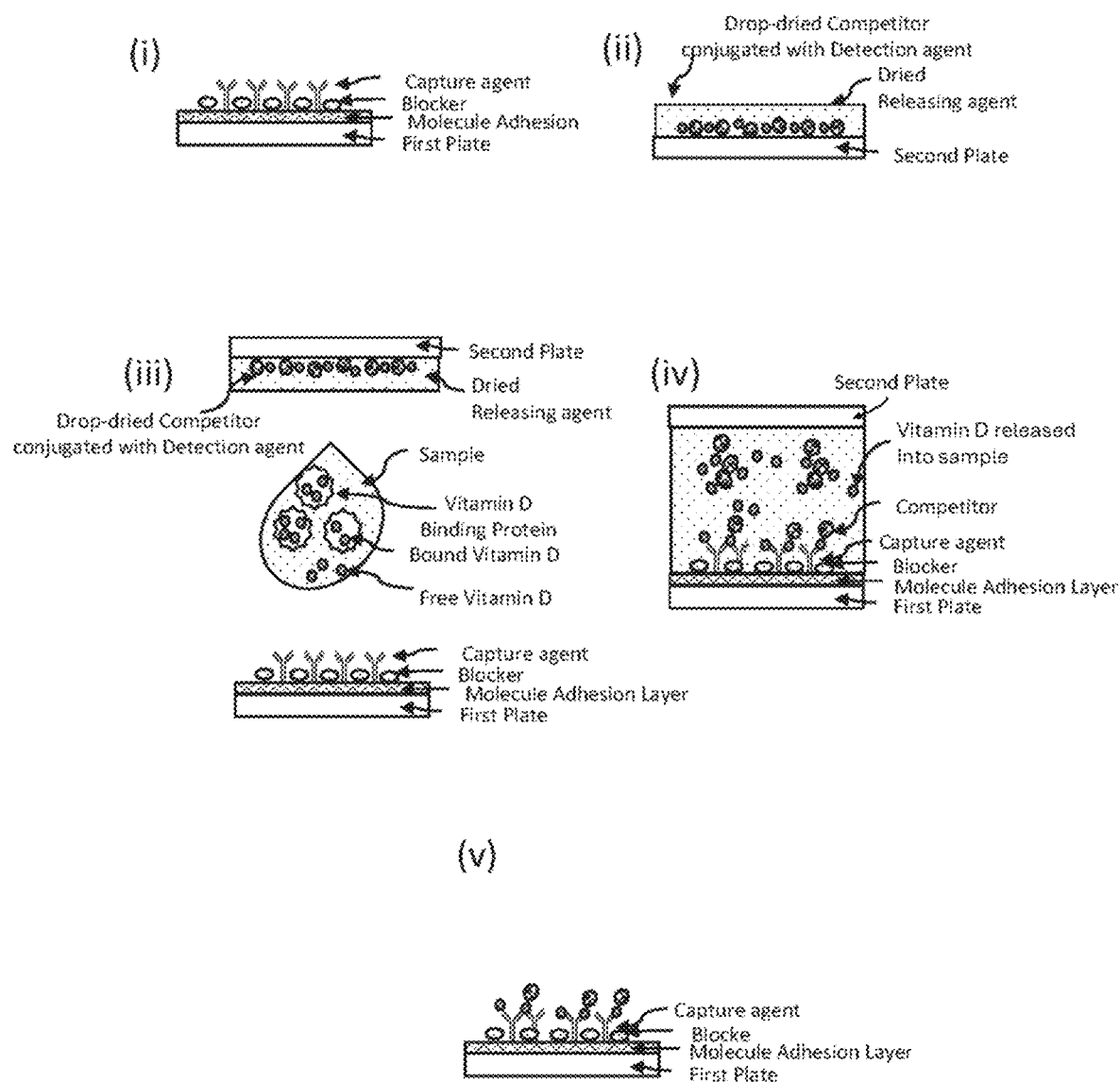
FIG. 2 is a schematic drawing of performing Vitamin D competitive Assay on QMAX card.

As shown in FIG. 2, both the sample and the competitor is contacted with an anti-25(OH) antibody. Antibodies for vitamin D are known in the art, and are widely used in the existing immunoassays for vitamin D. These same antibodies, as well as other binding proteins, can be used in the present invention as well. E.g., in the place of an antibody for Vitamin D an antibody fragment can be used such as produced with phage display technology. Suitable antibodies can be monoclonal or polyclonal antibodies. They can be obtained in known manner, e.g. polyclonal goat anti-vitamin D, polyclonal rabbit anti-vitamin D, or any other suitable antibody for vitamin D as known in the art from application in immunoassays for vitamin D. The antibodies as used are preferably immobilized. They are preferably used in a particulate form comprising solid carriers. Typically, the antibody is coated on a solid phase, e.g. on a QMAX card. In a preferred embodiment, the antibodies are coated onto the first plate of QMAX, which facilitates their speed to capture the analyte and competitor by reducing diffusing time.

A.1 the Process of Using the QMAX Device for Competitive Immunoassay of Vitamin D FIG. 2 illustrate the process of using the QMAX device for a competitive immunoassay of Vitamin D, comprising: (a) prepare first plate with bound capture agent (b) prepare second plate with dried competitive agent and releasing agent (c) adding sample onto the surface of prepared first plate; (d) Close and press prepared second plate onto the sample; (c) Incubation for an amount of time, then (d) an optional wash; (e) determining the amount of the competitor with fluorescence label bound.

As shown in FIG. 2, (i) On the first plate, capture agent is bio/chemically bound on the surface, then dried, blocked and stabilized.

As shown in FIG. 2, (ii) On the second plate, detection agent and releasing agent is drop dried on the surface. The conjugate of vitamin D with a functional label is drop-dried on the QMAX second plate. Numerous labeled compounds are known that are capable of serving as competitive binding antigens in immunoassays for the determination of vitamin D. Typical labels are radiolabels, fluorescent labels, luminescent labels, biotin labels, gold labels, enzyme labels. Competitive binding assays are known to the skilled person, and do not require elucidation, notably since this part of the method of the invention can be carried out using any label known to be suitable for the determination of vitamin D. Labels that can be used are, inter alia, those disclosed in the foregoing references on existing vitamin D immunoassays.

As shown in FIG. 2, (ii) The Releasing agent of Vitamin D from sample is perfluoro alkyl acid with a carbon chain of 4~12 atoms, or a combination of such thereof. In certain embodiments, the releasing agent is hydroxylated aromatic carboxylic acid. In certain embodiments, the releasing agent is pH regulating agent, i.e. formic acid, phosphoric acid. In certain embodiments, the releasing agent is enzymic reagent proteolytic to digest DBP protein.

As shown in FIG. 2 (iii) Drop the sample directly on the first plate's surface, which has capture reagent, then press the second plate onto the sample with the side of surface that has detection agent and releasing agent.

As shown in FIG. 2 (iv) During this incubation time, the sample start to release vitamin D by the releasing agent and the competitor on the second plate start to dissolved in the sample and diffuse to the first plate. Both the competitor and released Vitamin D in the sample will compete for the limited binding sites of the capture reagent.

As shown in FIG. 2 (v) After incubation, an optional step of wash is carried by removing the second plate and washing with washing buffer (Tris buffer contain surfactants). After drying, the QMAX card is ready for measurement. Fluorescence signal is measured by a fluorimetry setup, which uses an light that matches the fluorescence label's excitation band to excite the fluorescence emission, which can be detected either from reflection or transmission direction.

The two plates, first plate and second plate, are moveable relative to each other into different configuration. One of the configurations is an open configuration, in which the two plates are partially or entirely separated apart and the spacing between the plates are not regulated by the spacers. FIG. 1 shows the plates in the open configuration, in which a sample, such as but not limited to blood, can be added to first plate, the second plate, or both, of the plates and. In some embodiments, the inner surface of a respective plate comprises a sample contact area, which occupies a part of the entirety of the inner surface. In certain embodiments, the spacers are positioned within the sample contact area. In some embodiments, the spacers are not fixed to any one of the plates, but are mixed in the sample.

FIG. 2 (iv) shows the sectional view of the plates at the closed configuration, which is another of the configurations between the first plates and the second. In the closed configuration, the inner surfaces of the plates are pressed against each other, at least part of the sample is pressed into a layer of highly uniform thickness. In some embodiments, the layer of uniform thickness is confined by the inner surfaces of the two plates and the thickness is regulated by the height of the spacers. For clarity purposes, the spacer are not shown to scale in FIG. 2 and the thickness of the sample layer is not in proportion to the spacer height as shown in FIG. 1. In some embodiments, the uniform thickness of the sample is the same as the spacing between the plates; in certain embodiments the thickness of the sample and the spacing between the plates are the same as the height of the spacers.

In some embodiments, the first plate can be any material with flat or engineered solid surface. Examples for the first plate include but are but not limited to: plastic, silicon, PMMA, gold and glass. In some embodiments, the second plate can be any material with flat or engineered solid surface. Examples for the first plate include but are but not limited to: plastic, silicon, PMMA, gold and glass.

In some embodiments, the method of the present invention, before step (v) and after step (iv), further comprise incubating the layer of uniform thickness for a predetermined period of time. In certain embodiments, the predetermined period of time is equal to or longer than the time needed for the detection antibody to diffuse into the sample across the layer of uniform thickness. In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

In some embodiments, the inner surface can be washed with washing solution absorbed in a sponge. In some embodiments, the washing is conducted by squeezing the sponge to release the wash solution onto the inner surface of the first plate and releasing the sponge to reabsorb the wash solution. In some embodiments, the washing improves the limit of detection (LOD) for the detectable signal.

For detection and/or measurement of the signal, a plate reader can be used. In some embodiments, the plates are read without washing and both plates (in the closed configuration) are inserted into the reader. In some embodiments, the inner surface of the first plate is washed and the second plate is put back onto the first plate before reading so that both plates (in the closed configuration) are inserted into the reader. In some embodiments, the inner surface of the first plate is washed and the second plate is not put back onto the first plate before reading so that only the first plate is inserted into the reader. In certain embodiments, if only the first plate is read, the user can dry the first plate before inserting into the reader.

In some embodiments, the reader is configured to be connected to a computing device, such as but not limited to tablet computers and smart phones. For example, in certain embodiments the reader is configured to be connected to a smart phone, which can provide hardware and software for sample detection and quantification, such as but not limited to illumination, image capturing, image analysis, and calculation of analyte amount.

A.2 Examples for Immunoassay Results

FIG. 3 shows an example of a standard curve of a competitive immunoassay of vitamin D performed on QMAX card coated with 50 nm thickness of gold, with a competitor of Vitamin D conjugated to fluorescent beads with 40 nm diameter; and releasing agent of Perfluorooctanoic acid PFOA. The concentration of vitamin D in the sample is determined by competitive assay. It will be understood that the interpretation of the values measured, is determined by a measurement of the label, i.e. the fluorescence intensity, or the number of fluorescent labels. The calibration for the assay can be done by providing standards comprising a predetermined concentration of 25-OH vitamin D. The concentration of Vitamin D in the calibrators is preferably determined using an LC-MS-MS method.

The competitive assay on QMAX card for 25OHD was performed according to the following protocol.

1. First, prepare the first plate with Au surface (3 mm by 3 mm) with dithiobis(succinimidyl undecanoate) (DSU) SAM. DSU at preferable concentration is dropped on top of the Au surface by immersion and incubated overnight.
2. After washing, Monoclonal mouse anti-VD antibody (BBI solution) at preferable concentration is drop by immersion and incubated for 5 hrs at room temperature. The plate is blocked with casine in Tris buffer by immersion and dried with antibody stabilizer reagent, whose composition is standard and well-known thus does not require elucidations.
3. The second plate is drop-dried with the 20 uL of competitor agent and releasing agent with preferable concentrations. The competitor is prepared by mixing preferable concentration Vitamin D conjugated with biotin to preferable concentration 40 nm fluorescent beads coated with streptavidin. The releasing agent is PFOA.
4. On the first plate, 2 uL of sample is dropped on the surface. Immediately after the step, close and press tightly the second plate. Let the QMAX card incubate for 5 min.
5. (Optional) After incubation, remove the second plate and wash with washing buffer (Tris buffer contain surfactants). After drying, the QMAX card is ready for measurement.

The signal generated by the assay on the QMAX card is inversely proportional to the concentration of 25 (OH) Vitamin D in the sample or standards. The concentration of 25(OH) vitamin D in the unknown sample can be calculated by comparing the signal of unknowns with the response of standards As shown in FIG. 3 (ii). Samples (Vitamin D spiked in serum) with concentration from 0 nM~375 nM is measured. Their fluorescence intensity vs. concentration is plotted as standard curve. By using the well-established criterion for Limit of Detection (LOD), which is the background sample signals minus 3 times their standard deviation. The LOD is found to be 19.3 nM. (Typical threshold level that considered as VD deficiency is 50 nM.)

A.3 More Embodiments of Present Invention

A1 A method for performing a competitive assay, comprising
  (a) obtaining a first plate comprising, on its inner surface, a sample contact area that has a binding site, wherein the binding site comprises immobilized capture agent that binds a target analyte in a sample;
  (b) obtaining a second plate comprising a sample contact area that has a storage site, wherein the storage site comprises competitive agent that is capable of, upon contacting the sample, diffusing in the sample, wherein the competitive agent competes with the analyte for binding to the capture agents at the binding site, wherein the first plate and second plate are movable relative to each other into different configurations, including an open and a closed configurations;
  (c) depositing, in an open configuration, the sample on one or both of the sample contact areas of the plates, wherein in the open configuration, the sample contact areas of the plates are separated larger than 200 um;
  (d) after (c), bringing the two plates to a closed configuration, wherein, in the closed configuration, at least part of the sample deposited in (c) is confined between the sample contact areas of the two plates, and has an average thickness in the range of 0.01 to 200 μm; and
  (e) detecting a signal from (i) a competitive agent that is captured by the binding site, (ii) an analyte that is captured by the binding site, or (iii) both (i) and (ii).

B1 A device for performing a competitive assay, comprising:
  a first plate, a second plate, a binding site, and a storage site, wherein:
    the first plate comprises, on its inner surface, a sample contact area that has a binding site, wherein the binding site comprises immobilized capture agent that binds a target analyte in a sample;
    the second plate comprising a sample contact area that has a storage site, wherein the storage site comprises a competitive agent that is capable of, upon contacting the sample, diffusing in the sample, wherein the competitive agent competes with the analyte for binding to the capture agents at the binding site;
    wherein the first plate and second plate are movable relative to each other into different configurations;
    wherein one of the configurations is an open configuration, in which the plates are partially or entirely separated apart, and the average spacing between the sample contact areas of the plates is larger than 300 um; and
    wherein another configuration is a closed configuration in which the average spacing between the sample contact areas of the plates is 200 μm or less.

C1. The method or device of any prior embodiment, wherein one or both of the sample contact areas comprise spacers, wherein the spacers regulate the spacing between the sample contact areas of the plates when the plates are in the closed configuration.

C2. The method of any prior embodiment, wherein the spacing between the sample contact areas when the plates are in a closed configuration is regulated by spacers.

C3. The device of any prior embodiment, wherein the device further comprises spacers that regulate the spacing between the sample contact areas when the plates are in a closed configuration.

C4. The method or device of any prior embodiment, wherein the storage site further comprises another reagent, in addition to the competitive agent.

C5. The method or device of any prior embodiment, wherein the binding site comprises, in addition to immobilized capture agent, another reagent that is, upon contacting the sample, capable of diffusion in the sample, C6. The method or device of any prior embodiment, wherein the binding site faces the storage site when the plates are in the closed configuration.

C7. The method or device of any prior embodiment, wherein the first plate comprises a plurality of binding sites and the second plate comprises a plurality of corresponding storage sites, wherein each biding site faces a corresponding storage site when the plates are in the closed configuration.

C8. The method and device of any prior embodiment, wherein the detection agent is dried on the storage site.

C9. The method or device of any prior embodiment, wherein the capture agents at the binding site are on an amplification surface that amplifies an optical signal of the analytes or the captured competitive agents.

C10. The method or device of any prior embodiment, wherein the capture agents at the binding site are on an amplification surface that amplifies an optical signal of the analytes or the captured competitive agents in the embodiment 1, 2 and 3, wherein the amplification is proximity-dependent in that the amplification significantly reduced as the distance between the capture agents and the analytes or the competitive agents increases.

C11. The method or device of any prior embodiment, wherein the detection of the signal is electrical, optical, or both. (Will add more on the detection later. Fluorescence, SPR, etc.).

C12. The method or device of any prior embodiment, wherein the target analyte is 25OH vitamin D.

C13. The method or device of any prior embodiment, wherein the sample is a blood sample (whole blood, plasma, or serum).

C14. The method or device of any prior embodiment, wherein the target analyte is 25OH Vitamin D.

C15. The method or device of any prior embodiment, wherein the capture agents for vitamin D are antibodies that specifically binds to 25OH Vitamin D; and C16. The method or device of any prior embodiment, wherein the immobilized capture agents are immobilized on the binding site through molecule adhesion layer.

C17. The method or device of any prior embodiment, wherein the molecule adhesion layers are molecules that has functions groups bind bio/chemically to the surface of first plate.

C18. The method or device of any prior embodiment, wherein the molecule adhesion layers are molecules that has functions groups bind bio/chemically to the capture agents.

C19. The method or device of any prior embodiment, wherein the storage site further stores, in addition to the detection agent, a 25OH Vitamin D releasing agent that frees a Vitamin D from its binding agent, e.g. binding protein.

C20. The method or device of any prior embodiment, wherein the capture agent specifically binds to free 25OH Vitamin D.

C21. The method or device of any prior embodiment, wherein the Vitamin D releasing agent is perfluoro alkyl acid with a carbon chain of 4~12 atoms, or a combination of acid thereof.

C22. The method or device of any prior embodiment, wherein the Vitamin D releasing agent is drop-dried on the surface of the first plate.

C23. The method or device of any prior embodiment, wherein the releasing agent's concentration is from 0.1% to 5% after the releasing reagent forms a homogeneous mixture with the sample.

[Competitive Agent]

C24. The method or device of any prior embodiment, wherein a competitive agent is mixed with samples in the presence of releasing agent.

C25. The method or device of any prior embodiment, wherein the competitive agent has specific binding to capture agent.

C26. The method or device of any prior embodiment, wherein a competitive agent is drop-dried on the second plate.

C27. The method or device of any prior embodiment, wherein a competitive agent is dissolved instantaneously into samples after sample contact the second plate.

C28. The method or device of any prior embodiment, wherein the competitive agent forms a homogeneous mixture with the sample after dissolving into the sample.

C29. The method or device of any prior embodiment, wherein the competitive agent is 25OH Vitamin D conjugate to biotin.

C30. The method or device of any prior embodiment, wherein the total amount of binding sites on the capture agent of the first plate is equal or less than the total amount of competitor agent C31. The method or device of any prior embodiment, wherein the competitive agent and 25OH Vitamin D released from sample compete for binding to the limited binding site on the first plate C32. The method or device of any prior embodiment, wherein the amount of competitor bound to capture agent is subject to the amount of 25OH Vitamin D in the sample C33. The method or device of any prior embodiment, wherein the amount of competitive agent bound to capture agent is determined by the amount of detection agent bound to competitive agent C34. The method or device of any prior embodiment, wherein the detection agent is fluorescence label that specifically binds to biotin.

C35. The method or device of any prior embodiment, wherein the fluorescence label is fluorescent microsphere coated with a plurality of streptavidin, or neutravidin, or a combination avidin-complex thereof.

C36. The method or device of any prior embodiment, wherein the fluorescence microsphere's diameter is from 20 nm to 2 um.

C37. The method or device of any prior embodiment, wherein the amount of fluorescence dye in the microsphere is from 1 nM~1 uM.

C38. The method or device of any prior embodiment, wherein the material of fluorescent microsphere is dielectric, (e.g. SiO2, Polystyrene,) or the combination of dielectric materials thereof.

C39. The method or device of any prior embodiment, which comprises steps of adding the detection agent of said fluorescence label to the first plate to bind competitive agent.

C40. The method or device of any prior embodiment, which comprises steps of washing after the detection agent is added to the first plate AA1. AA device for a competitive assay, comprising:
  a first plate, a second plate, a binding site, and a storage site, wherein:
   i. the plates are movable relative to each other into different configurations;
   ii. each plate respectively comprises an inner surface that has a sample contact area for contacting a sample that comprises a target analyte,
   iii. the first plate, at the binding site in its sample contact area, comprises a capture agent, and
   iv. the second plate, at the storage site in its sample contact area, comprises a detection agent;
    wherein one of the configurations is an open configuration, in which the plates are partially or entirely separated apart, and the average spacing between the sample contact areas of the plates is larger than 300 um;
    wherein another of the configurations is a closed configuration, which is configured after the sample deposition in the open configuration, and in which the average spacing between the sample contact areas of the plates is 200 μm or less;
    wherein the capture agent is configured to bind to the target analyte and immobilize the analyte to the inner surface of the first plate; and
    wherein the detection agent is configured to diffuse into layer of uniform thickness and specifically bind to the analyte to produce a detectable signal.

BB1 AA method for a competitive assay, comprising
  (f) obtaining the device of embodiment AA1;
  (g) depositing the sample on one or both of the sample contact areas of the plates;
  (h) after (b), bring the two plates to a closed configuration, wherein, in the closed configuration;
  (i) incubating for a predetermined period of time, and
  (j) detecting a signal of: (i) the detection agent that are captured by the binding site, (ii) the analyte that are captured by the binding site, or (iii) both (i) and (ii).

CC1. The device and method in any prior embodiments, wherein the binding site faces the storage site when the plates are in the closed configuration.

CC2. The device and method in any prior embodiments, wherein the first plate comprise a plurality of binding sites and the second plate comprises a plurality of corresponding storage sites, wherein each biding site faces a corresponding storage site when the plates are in the closed configuration.

CC3. The device and method in any prior embodiments, wherein one or both of the sample contact areas comprise spacers, wherein the spacers regulate, in the closed configuration of the plates, the spacing between the sample contact surface of the plates.

CC4. The device and method in any prior embodiments, wherein the capture agents at the binding site are on an amplification surface, which is configured to amplify an optical signal of the analytes or the captured detection agents.

CC5. The device and method in any prior embodiments, wherein the capture agents at the binding site are on an amplification surface, which is configured to amplify an optical signal of the analytes or the captured detection agents, and the amplification is proximity-dependent.

CC6. The device and method in any prior embodiments, wherein the detection of the signal is by electrical, optical, or both types of signals.

CC7. The device and method in any prior embodiments, wherein the target analyte is vitamin D.

CC8. The device and method in any prior embodiments, wherein the sample is a blood sample (whole blood, plasma, or serum).

[Capture Agent]

CC9. The device and method in any prior embodiments, wherein the capture agents for vitamin D are antibodies that specifically binds to 25OH Vitamin D.

CC10. The device and method in any prior embodiments, wherein the capture agents are antibodies that are immobilized on the sample contact surface through one or more molecule adhesion layers.

[Molecule Adhesion Layer]

CC11. The device and method of embodiment CC10, wherein the molecule adhesion layers comprise molecules that have function groups configured to bind bio/chemically to the inner surface of first plate.

CC12. The device and method of embodiment CC10, wherein the molecule adhesion layers comprise molecules that have function groups configured bind bio/chemically to the capture agents.

[Releasing Agent]

CC13. The device and method in any prior embodiments, wherein the target analyte is 25OH Vitamin D, which is released free from sample by a releasing agent.

CC14. The device and method of embodiment CC13, wherein the capture agent specifically binds to 25OH Vitamin D in the presence of the releasing agent.

CC15. The device and method of embodiment CC13, wherein the releasing agent is perfluoro alkyl acid with a carbon chain of 4~12 atoms, or a combination of acid thereof.

CC16. The device and method of embodiment CC13, wherein the releasing agent is drop-dried on the surface of the first plate.

CC17. The device and method of embodiment CC13, wherein the releasing agent is dissolved instantaneously into samples after sample contact the first plate.

CC18. The device and method of embodiment CC13, wherein the releasing agent forms a homogeneous mixture with the sample.

CC19. The device and method of embodiment CC13, wherein the concentration of the releasing agent is from 0.1% to 5% after the releasing reagent forms a homogeneous mixture with the sample.

[Competitive Agent]

CC20. The device and method in any prior embodiments, wherein the sample further comprises a competitive agent.

CC21. The device and method of embodiment CC20, wherein the competitive agent is configured to specifically bind to capture agent.

CC22. The device and method of embodiment CC20, wherein a competitive agent is drop-dried on the second plate.

CC23. The device and method of embodiment CC20, wherein a competitive agent is dissolved instantaneously into samples after sample contact the second plate.

CC24. The device and method of embodiment CC20, wherein the competitive agent forms a homogeneous mixture with the sample after dissolving into the sample.

CC25. The device and method of embodiment CC20, wherein the competitive agent is 25OH Vitamin D conjugate to biotin.

[Competitive Assay]

CC26. The device and method in any prior embodiments, wherein the total amount of molecule binding sites on the capture agent of the first plate is equal to or less than the total amount of competitor agent.

CC27. The device and method of embodiment CC20, wherein the competitive agent and 25OH Vitamin D released from the sample compete for binding to the limited binding site on the first plate CC28. The device and method in any prior embodiments, wherein the amount of competitor bound to capture agent is subject to the amount of 25OH Vitamin D in the sample CC29. The device and method in any prior embodiments, wherein the amount of competitive agent bound to capture agent is determined by the amount of detection agent bound to competitive agent

[Detection Agent]

CC30. The device and method in any prior embodiments, wherein the detection agent comprises a fluorescence label that specifically binds to biotin.

CC31. The device and method of embodiment CC30, wherein the fluorescence label is fluorescent microsphere coated with a plurality of streptavidin, or neutravidin, or a combination avidin-complex thereof.

CC32. The device and method of embodiment CC31, wherein the fluorescence microsphere's diameter is from 20 nm to 2 um.

CC33. The device and method of embodiment CC30, wherein the amount of fluorescence dye in the microsphere is from 1 nM~1 uM.

CC34. The device and method of embodiment CC30, wherein the material of fluorescent microsphere is dielectric, (e.g. SiO2, Polystyrene,) or the combination of dielectric materials thereof.

CC35. The method of any prior embodiments, further comprising the step of adding the detection agent having a fluorescence label to the first plate to bind the competitive agent.

CC36. The method of any prior embodiments, further comprising the step of washing after the detection agent is added to the first plate Related Documents The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

B. Assay with Beads Label (O11)

One aspect of the present invention is to accelerate the nanoparticle label binding time by making, prior to a binding, the nanoparticle label located at vicinity from the binding agent, such that the nanoparticle label will bind to the binding agent without diffusing through a long distance (hence without a long diffusion time).

Another aspect of the present invention is to accelerate the nanoparticle label binding time by (a) prior to providing a liquid sample, putting the binding agent on an inner surface of a first plate and the nanoparticle label on an inner surface of a second plate, (b) providing a sample to be assayed between the inner surfaces of the two plates, (c) pressing the plates into a final configuration that has a smaller plate-spacing than that before pressing the plates, and (d) releasing the nanoparticle label on the inner surface of the plates into the solution, wherein the spacing in the final configuration is equal to or less than 250 microns.

Another aspect of the present invention is to accelerate the nanoparticle label binding time by making at least portion of the final sample film having a significant uniform thickness.

Another aspect of the present invention is to accelerate the nanoparticle label binding time by making at least portion of the final sample film having a significant uniform thickness, wherein the uniform thickness is regulated by a plurality of spacers.

Another aspect of the present invention is to accelerate the nanoparticle label binding time by making at least portion of the final sample film having a significant uniform thickness, wherein the uniform thickness is regulated by a plurality of spacers, and the final sample film is achieved by hand pressing the outer surface of the plates.

Device

FIG. 4 schematically shows an exemplary embodiment of a device for analyzing a liquid sample provided by the present invention, which comprises a first plate 10, a second plate 20, at least one nanoparticle label 99, and, optionally, a spacing mechanism (not shown).

In particular, FIG. 4 panel (A) shows the perspective and cross-sectional views of the first plate 10 and second plate 20. As illustrated in the figure, each plate respectively comprises an outer surface (12 and 22) and inner surface (11 and 21), and each inner surface has a sample contact area (not indicated) for contacting a sample that may contain a target analyte. Furthermore, the first plate inner surface 11 has a binding site 101 (not shown in the cross-sectional views) that has a predetermined area and is coated with at least one binding agent 111 (not shown in the perspective views). It should be noted, however, there may be more than one binding sites, and the binding site 101 may also exist on the second plate inner surface 21 (not shown), or both the first plate and second plate inner surfaces (11 and 21, not shown).

FIG. 4 panel (B) is a schematic illustration of the nanoparticle label 99, which comprises two interconnected parts: a nanoparticle 991 and a detection agent 992. The line segment in the figure that connects the two parts 991 and 992 symbolizes the interconnection between the two.

The term "nanoparticle" as used herein refers to a range of particles between 1 nm and 5 μm in size that are used in the field of bio/chemical sensing, assays, and reactions. The term "nanoparticle label" as used herein refers to a functionalized nanoparticle that is capable of affinity binding, as disclosed below, through its detection agent, which is capable of bringing about a change in a nanoparticle label-related signal. In particular embodiments, for assay purposes, the detection agent 992 and the binding agent 111 in the binding site 101 are configured to bind to each other in a specific manner either directly or indirectly, and their binding is configured to bring about a change in the nanoparticle label-related signal.

In some embodiments, the nanoparticle label-related signal is a signal provided by the nanoparticle 991 and/or the detection agent 992 themselves. For instance, the nanoparticle may be a gold nanoparticle, which can be used as a colorimetric sensor by changing the color it manifests depending on its aggregation state, indicative of whether or not and to what extent the nanoparticle labels bind to the detection agent. In other embodiments, the nanoparticle label 99 may comprise a third component that provides such a signal. In yet other embodiments, the nanoparticle label-related signal maybe a signal provided by other entity in the device and/or external entity, and the binding between the nanoparticle label 99 and the binding agent 111 causes physical or chemical alterations that lead to the changes in the signal. For instance, when the binding agent binds to the nanoparticle label containing a noble metal nanoparticle, the proximity of the noble metal may create a plasmonic effect that enhances or decreases a fluorescent signal that may be provided by the binding site or other binding entities pre-existing in or added to the sample solution.

In some embodiments, the first plate 10, second plate 20, or both may comprise one or more amplification sites that are each capable of amplifying the nanoparticle label-related signal when the nanoparticle label is in proximity of the amplification site. For instance, the amplification site can amplify the signal when the nanoparticle label in 100 nm or less, 200 nm or less, 500 nm or less, 1 μm or less, 5 μm or less, 20 nm or more, 80 nm or more, 320 nm or less, or 1.5 μm or more, from the amplification site. For instance, the binding site may be coated with a layer of noble metallic material, which may provide, among others, a plasmonic effect that enhances the fluorescence signal the nanoparticle label, the analyte, and/or the binding site may carry.

In some embodiments, the nanoparticle 991 may be selected from a group of nano-scale materials including, but not limited to, carbon nanotubes, fullerenes, dendrimers, quantum dots, noble metal nanoparticles, fluorophore-doped nanoparticles, rare earth-doped nanoparticles, superparamagnetic nanoparticles, and any combination thereof. Based on its composition and size, the nanoparticle may be capable of providing a luminescence signal, a chromatic signal, an electric signal, a magnetic signal, other forms of signal, or any combination thereof.

In some embodiments, the detection agent 992 may be selected from a group of molecules including, but not limited to, protein, peptide, peptidomimetics, streptavidin, biotin, oligonucleotide, oligonucleotide mimetics, any other affinity ligand and any combination thereof.

In some embodiments, the detection agent 992 and the binding agent 111 are configured to bind to each other specifically in a target analyte-related manner, so that they may bind to each other in a specific manner directly, indirectly, or both, and their binding is affected by the concentration of the target analyte. In some embodiments, the detection agent and the binding agent may bind directly to each other, for example, in a competitive immunoassay, the nanoparticle label may be configured to bind to the target analyte in the sample either directly or indirectly, which competes with the specific and direct binding between the nanoparticle label and the binding agent. In other embodiments, the detection agent and the binding agent are configured to bind to each other indirectly through the mediation of the target analyte in the sample, or in some other cases, through the mediation of the target analyte and other binding entities. For example, in a typical sandwich immunoassay, the binding agent, and the nanoparticle label may not bind to each other directly, but they may both bind to the target analyte at its different locations, forming a binding agent-target analyte-nanoparticle label sandwich structure. In yet other embodiments, the detection agent and the binding agent may be configured to bind to each other both directly and indirectly, and their distance, e.g. whether they bind directly or indirectly, or how many mediators exist in between the detection agent and the binding agent, is affected by the concentration of the target analyte. Skilled artisans in the field will be able to choose the appropriate nanoparticle label and binding agent for their specific applications without undue experimentation.

Referring to FIG. 4, the first plate 10 and the second plate 20 are movable relative to each other into different configurations. In some embodiments, one of the configurations is an open configuration, as illustrated in panel (A), in which the two plates are separated from each other either partially or completely, and the spacing between the two plates is not regulated by the spacing mechanism. In some embodiments, for analyzing a liquid sample, the sample may be deposited on one or both of the plates when they are in the open configuration.

FIG. 4 panel (C) shows another configuration of the two plates, a closed configuration. In some embodiments, after sample deposition in the open configuration of the plates, the sample analysis may be then performed when the plates are in the closed configuration. In the closed configuration, the spacing 102 between the two plates is regulated by the spacing mechanism; and more importantly, the thickness of a relevant volume of the deposited sample is reduced, compared to that in the open configuration of the plates, into a thin layer 904. The term "a relevant volume" as used herein refers to a part or entirety of the deposited sample. The reduced thickness of the layer 904 is confined by the inner surfaces of the plates (11 and 21) and in touch with the binding site 101, and is regulated by the plates (10 and 20) and the spacing mechanism. Moreover, as shown in the figure, the nanoparticle label 99 is in the thin layer 904, which allows the diffusion of the nanoparticle label 99 to the binding site 101 and the potential binding between the nanoparticle label 99 and the binding agent 111.

Reducing the spacing between the two plates 102 and therefore the thickness of the relevant volume of the sample 904 may significantly reduce the time for the binding between the binding agent and the nanoparticle label to reach equilibrium. Consequently, the speed for bio/chemical assays of a liquid sample using the device of the present invention can be significantly accelerated. In some embodiments, the spacing mechanism-regulated reduced thickness is 5 mm or less, 1 mm or less, 500 µm or less, 250 µm or less, 100 µm or less, 50 µm or less, 1 µm or less, 500 nm or less, 100 nm or less, 50 nm or less, 10 nm or less, 2 nm or more, 5 nm or more, 20 nm or more, 200 nm or more, 2 µm or more, 20 µm or more, 200 µm or more, or 2 mm or more. In other embodiments, the reduced thickness is substantially less than the average linear dimension of the predetermined area of the binding site 101.

In some embodiments, the spacing mechanism comprises a plurality of spacers that may be positioned between the first plate 10 and second plate 20 when the plates are in the closed configuration. In some embodiments, the spacers may have a range of different heights, but a maximum height of 5 mm or less, 1 mm or less, 500 µm or less, 250 µm or less, 100 µm or less, 50 µm or less, 1 µm or less, 500 nm or less, 100 nm or less, 50 nm or less, 10 nm or less, 2 nm or more, 5 nm or more, 20 nm or more, 200 nm or more, 2 µm or more, 20 µm or more, 200 µm or more, or 2 mm or more. In other embodiments, the spacers may have a predetermined substantially uniform height of 5 mm or less, 1 mm or less, 500 µm or less, 250 µm or less, 100 µm or less, 50 µm or less, 1 µm or less, 500 nm or less, 100 nm or less, 50 nm or less, 10 nm or less, 2 nm or more, 5 nm or more, 20 nm or more, 200 nm or more, 2 µm or more, 20 µm or more, 200 µm or more, or 2 mm or more.

The features as stated for the common device, as shown in FIG. 4 described thereof, are also applicable to the embodiments shown in FIGS. 5 to 10 and described thereof. In addition, it should be noted that the device serves as an example for the features shown in all figures and described thereof. In general, in the drawings, elements that serve a similar, or at least substantially similar, purpose are labeled with numbers consistent among the figures. Like numbers in each of the figures, and the corresponding elements, may not be discussed in detail herein with reference to each of the figures. Similarly, all elements may not be labeled or shown in each of the figures, but reference numerals associated therewith may be used for consistency. Elements, components, and/or features that are discussed with reference to one or more of the figures may be included in and/or used with any of the figures without departing from the scope of the present disclosure. Elements shown in each of the figures are for illustrative purposes only, their relative positioning, proportions, and/or sequences may be altered in particular embodiments without departing from the scope of the present disclosure.

Figure 5:
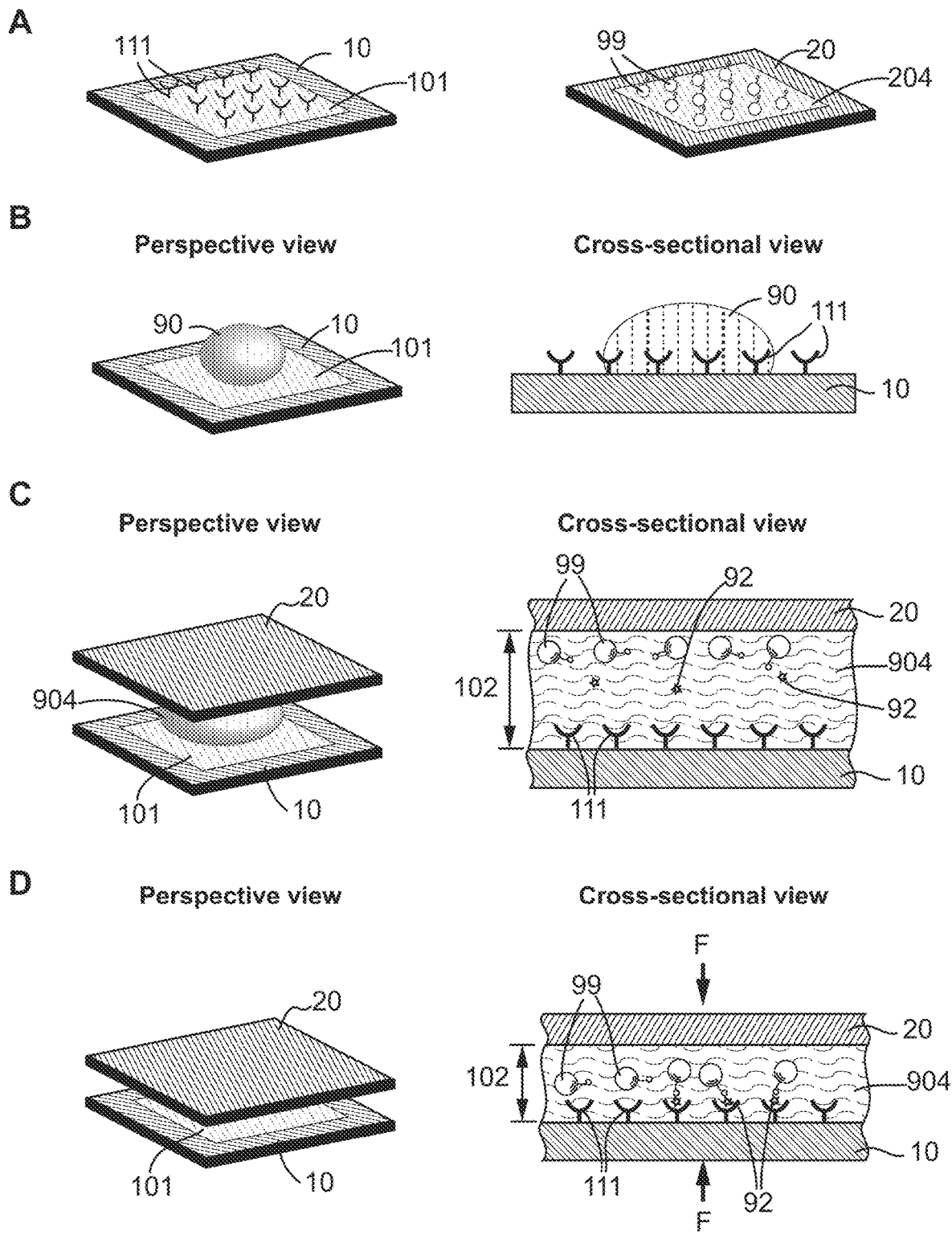
FIG. 5 shows another exemplary embodiment of a device for analyzing a liquid sample provided by the present invention. Panel (A) shows a prospective view of a first plate and a second plate, on which nanoparticle labels are attached, in the open configuration before the deposition of any sample; panel (B) shows that a sample is deposited on one of the plates in the open configuration; panel (C) shows that the two plates are brought from an open configuration to a closed configuration, confining the deposited sample in between, and the nanoparticle labels are released and diffuse in the sample after contacting the sample; panel (D) shows that using the first plate and the second plate to compress the sample into a thin layer, in which the nanoparticle label binds to the binding agent on the first plate indirectly through mediation of the target analyte in the sample.

FIG. 5 shows another exemplary embodiment of the device provided by the present invention In particular, panel (A) shows that the first plate 10 has at least one binding agent 111 on its binding site 101, and the nanoparticle label 99 is coated on the second plate sample contact area 20. Panel (B) shows that a liquid sample 90 containing an analyte 92 is deposited on on the first plate 10, the second plate 20 (not shown), or both (not shown) in the open configuration. Panel (C) shows an embodiment of the open configuration, in which the spacing between the two plates 102 is not regulated by the spacing mechanism (not shown), while the two plates are brought to face each other and contact the sample 90 with their sample contact areas (not marked). As shown in panel (C), the nanoparticle label 99 coated on the second plate 20 may be configured to, upon contacting the deposited liquid sample 90, be dissolved into the sample and then diffuse in it, forming the label solution 904. It should be noted that, however, the nanoparticle 99 may also be coated on the first plate 10, or both the first plate 10 and the second plate 20. In certain embodiments, the binding agent 111 and the nanoparticle 99 may be coated on different plates. In other embodiments, some of the binding agent 111 and some of the nanoparticle 99 may be coated at different locations on the same plate, or even at the same location on the same plate. Panel (D) shows that in this particular embodiment, in the closed configuration, in which the spacing between the two plates 102, and therefore the thickness of the relevant volume of the label solution 904, are reduced compared to the thickness of the label solution in the open configuration or the spacing between the two plates 102 in panel (C), the nanoparticle label 99 diffuses in the relevant volume of the label solution 904 and specifically binds to the analyte that is captured and immobilized by the specific binding of the binding agent 111, forming the binding agent-analyte-nanoparticle label sandwich structure. As disclosed above, in other embodiments, the nanoparticle label may also be configured to bind to the binding agent directly. And in yet other embodiments, the nanoparticle label and the binding agent may be configured to bind to each other through the mediation of the analyte and other matter(s) in the label solution.

In other embodiments, the nanoparticle label 99 may be separate from the two plates (10 and 20), and may be added into the sample before, during, or after the sample deposition on one or both of the plates.

FIG. 6 shows another exemplary embodiment of the device provided by the present invention. The device comprises a first plate 10, a second plate 20, spacers 40, and at least one nanoparticle 99 (only one shown in panel (B)). Particularly, as shown in panel (A), the second plate 20 comprises a plurality of spacers 40 that are fixed on its inner surface 21, and at least one of the spacers is inside the sample contact area (not indicated). It should be noted, however, the spacers 40 may also be fixed on the first plate inner surface 11 (not shown), or both of the first plate and second plate inner surfaces (11 and 21, not shown). In these embodiments, the spacers 40 serve as the spacing mechanism and are a part of the first plate 10, second plate 20, or both. In some embodiments, the spacers have a highly uniform height, and/or a predetermined constant inter-spacer distance. In the closed configuration of the two plates, as shown in panel (C), the spacing between the two plates 102 is regulated by the spacers 40. In some embodiments, the spacing 102 may be about equal to the uniform height of the spacers 40, and consequently, the thin layer 904 may become a layer of substantially uniform thickness and the uniform thickness is about the uniform height of the spacers. In these particular embodiments, the two plates form a part of a compressed regulated open flow (CROF) device or otherwise named QMAX (Q: quantitative, M: multiplexing, A: adding reagents, X: acceleration) device, such as but not limited to the CORF device or QMAX device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

FIG. 7 is a flow chart of an exemplary embodiment of a method of analyzing a liquid sample using nanoparticle label. The assay method utilizes the device as disclosed above. As illustrated, the method may comprise:

a) providing a first plate 10, second plate 20, a spacing mechanism, and at least one nanoparticle label 99, wherein as disclosed above:
   i. the first plate 10 and second plate 20 are movable relative to each other into different configurations;
   ii. each plate respectively comprises an outer surface and an inner surface that has a sample contact area for contacting a liquid sample; and
   iii. one or both of the plates comprise, in a respective sample contact area, one or a plurality of binding sites 101 that have a predetermined area and is coated with at least one binding agent 111;

b) adding the nanoparticle label 99 into a liquid sample to form a label solution,
   wherein the nanoparticle label 99 comprises two interconnected parts: a nanoparticle 991 and a detection agent 992,
   wherein the detection agent 992 and the binding agent 111 are configured to bind to each other specifically in a target analyte-related manner, and
   wherein the binding between the detection agent 992 and the binding agent 111 is configured to bring about a change in a detectable signal related to the nanoparticle label 99;

c) depositing the label solution on the inner surface of at least one of the two plates when the two plates are configured in the open configuration, in which: the two plates are partially or entirely separated apart and the spacing between the plates is not regulated by the spacing mechanism; and d) compressing a relevant volume of the deposited label solution by bringing the two plates into the closed configuration, in which: the thickness of the relevant volume of the deposited label solution is reduced, compared to that in the open configuration of the plates, into a thin layer 904 that is confined by the inner surfaces of the plates and in touch with the binding site; the reduced thickness of the layer is regulated by the plates and the spacing mechanism; and the nanoparticle label is in the thin layer,
   wherein the relevant volume is a portion or an entire volume of the label solution; and
   wherein reducing the thickness of the relevant volume of the label solution reduces the time for the binding between the binding agent and the nanoparticle label to reach equilibrium.

As disclosed, in the closed configuration of the two plates, the reduction of the thickness of the relevant volume of the label solution may significantly reduce the time for the binding between the binding agent and the nanoparticle label to reach equilibrium (termed "saturation time" hereinafter). In some embodiments, the reduced thickness is 5 mm or less, 1 mm or less, 500 µm or less, 250 µm or less, 150 µm or less, 50 µm or less, 1 µm or less, 500 nm or less, 100 nm or less, 50 nm or less, 10 nm or less, 2 nm or more, 5 nm or more, 20 nm or more, 200 nm or more, 2 µm or more, 20 µm or more, 200 µm or more, or 2 mm or more. In other embodiments, the reduced thickness is substantially less than the average linear dimension of the predetermined area of the binding site 101.

In some embodiments, the method may further comprise a step of e) after step (d) and while the plates are in the closed configuration, assessing the binding between the binding agent 111 and the nanoparticle label 99 in the thin layer 904, through analyzing the nanoparticle label-related signal, after incubating for a time that is about equal to or longer than the time that it takes for the nanoparticle label to diffuse across the thickness of the layer of the reduced thickness.

In some embodiments, the step (e) may comprise stopping the incubation after said time, and then assessing the binding between the binding agent and the nanoparticle label in the thin layer.

In some embodiments, the signal analyzing in step (e) may comprise measuring the nanoparticle-related signal such as, but not limited to, (i) luminescence selected from photoluminescence, electroluminescence, and electrochemiluminescence; (ii) light absorption, reflection, transmission, diffraction, scattering, or diffusion; (iii) surface Raman scattering; (iv) electrical impedance selected from resistance, capacitance, and inductance; (v) magnetic relaxivity; (vi) any combination of (i)-(v).

As disclosed above, in some embodiments of the device for analyzing a liquid sample, the spacing mechanism may comprise spacers 40 that are fixed to the first plate 10, the second plate 20, or both, and that the first plate 10 and the second plate 20 may form part of the "CROF device". Correspondingly, in some embodiments, the assay method using nanoparticle label may comprise:

(a) providing a first plate and a second plate, wherein:
  i. the first plate and second plate are movable relative to each other into different configurations,
  ii. each plate respectively comprises an outer surface and an inner surface that has a sample contact area for contacting a liquid sample that contains a target analyte,
  iii. one or both of the plates comprise, in a respective sample contact area, one or a plurality of binding sites that have a predetermined area and is coated with at least one binding agent, and
  iv. one or both of the plates comprise a plurality of spacers that are fixed with a respective sample contact area, wherein the spacers have a predetermined substantially uniform height and a predetermined constant inter-spacer distance, and at least one of the spacers is inside the sample contact area;

(b) adding at least one nanoparticle label to the sample to form a label solution,
  wherein the nanoparticle label comprises two interconnected parts: a nanoparticle and a detection agent,
  wherein the detection agent and the binding agent are configured to bind to each other specifically in a target analyte-related manner, and
  wherein the binding between the detection agent and the binding agent is configured to bring about a change in a detectable signal related to the nanoparticle;

(c) depositing the label solution on the inner surface of at least one of the two plates when the two plates are configured in an open configuration, in which: the two plates are partially or entirely separated apart and the spacing between the plates is not regulated by the spacers; and (d) compressing a relevant volume of the deposited label solution by bringing the two plates into a closed configuration, in which: the thickness of the relevant volume of the deposited label solution is reduced, compared to that in the open configuration of the plates, into a layer of highly uniform thickness that is confined by the inner surfaces of the plates and in touch with the binding site; the uniform thickness of the layer is regulated by the plates and the spacers, and is 250 µm or less and substantially less than the average linear dimension of the predetermined area of the binding site; and the nanoparticle labels is in the layer of uniform thickness,
  wherein the relevant volume is a portion or an entire volume of the label solution; and
  wherein reducing the thickness of the relevant volume of the label solution reduces the time for the binding between the binding agent and the nanoparticle label to reach equilibrium.

In these embodiments, the configuration of the spacers with substantially uniform height and constant inter-spacer distance and the achievement of a layer of highly uniform thickness with at least part of the deposited label solution may provide manifold advantages. Particularly, the uniform thickness of the layer may be about equal to the uniform height of the spacers. In some embodiments, the reduction of sample thickness to the uniform thickness may uniformly reduce the time needed for the binding between the nanoparticle label and the binding agent to reach equilibrium, and accelerate the assay in a uniform manner. In some embodiments, the relevant volume of the layer of uniform thickness may be determined by timing the predetermined uniform height with the lateral area of the relevant volume, therefore, the concentration of the target analyte may be determined, without knowing the exact volume of the label solution that is deposited and being analyzed, by dividing the assessed quantity of the target analyte in the layer of uniform thickness by the volume of the uniform thickness layer. In other embodiments, only a part of the relevant volume, in which the target analyte is quantified, may be determined. The volume of said part may be calculated by times the spacer height with the lateral area of said part, which may be calculated based on the number of the spacers in the part and the predetermined spacer height and inter-spacer distance. Accordingly, the concentration of the analyte may be calculated by dividing the quantity of the analyte in said part of the layer of uniform thickness by the volume of said part. In some embodiments, the conformable pressing force may be removed after bringing the two plate into the closed configuration, as the two plates may remain self-held and the thickness of the layer of uniform thickness after removal of the conformable pressing force may be substantially the same as of the layer of uniform thickness before removing the conformable pressing force and deviate from the spacer height by less than 10%. Such configuration may allow for ease to operate the device.

Example

The device and method provided by the present invention have been achieved experimentally according to some embodiments. In the experiments described below, two different types of devices were tested in direct assays, in which streptavidin-coupled microspheres were used as the nanoparticle label and human IgG-biotin antibody (IgG) as the binding agent. The experimental data as presented below suggest that: 1) the disclosed device and method can be used to shorten the saturation time for the nanoparticle label to bind to the binding agent and therefore significantly accelerate the bio/chemical assays, in the example presented here, the saturation time could be reduced to as short as between 30 sec and 60 sec; 2) furthermore, with the shortened saturation time, fluorescence amplification surface (gold surface in this case), an exemplary amplification site on the inner surface of one of the plates, can significantly amplify the fluorescence signal of the nanoparticle label and reduce limit of detection in the nanoparticle-enabled bio/chemical assays.

One type of device tested here consisted of: a 3.5 mm×3.5 mm plain glass plate coated with gold on the surface (named "Au plate" herein), on which a layer of IgG was coated, a 5 mm×5 mm X-plate with pillar spacers of 30 μm uniform height, and 40 nm diameter streptavidin-coupled red fluorescent (580/605 nm) microspheres (40 nm streptavidin-beads). Another type of device consisted of: a 3.5 mm×3.5 mm plain glass plate with one surface coated with a layer of IgG, an X-plate (same as above), and 1 μm diameter streptavidin-coupled red fluorescent (580/605 nm) microspheres (1 μm streptavidin-beads). The term "X-plate" as used herein refers to part of the device of the present disclosure, the plate with spacers fixed on one of its surfaces, wherein the spacers have a pre-determined uniform height and a constant inter-spacer distance.

Plates Preparation:

For Au plates, given that proteins do not bind to metal surface well, a self-assemble-monolayer (SAM) of dithiobis succinimidyl undecanoate (DSU) was used as the adhesion layer. First, Au plate was coated in DSU solution (1 mM in Dioxane) overnight at room temperature (RT). Second, after the formation of DSU adhesion layer, binding agent (human IgG-biotin) was bound to the plate. Briefly, 10 μL human IgG-biotin antibody (IgG) solution was dropped onto the gold surface of the Au plate to form a 1 mm thick layer for a 2-hour incubation at RT, and then washed away by PBST, which allowed the binding of IgG to the adhesion layer on the Au plate. Here the human IgG-biotin was dissolved in PBS solution in a series of concentrations from 1 μg/mL to 1 fg/mL, and each plate was coated with a pre-determined concentration of IgG. Last, 10 μL BSA (4% in PBS) was dropped onto the plate for a 2-hour blocking at RT and then washed away by PBST.

For plain glass plates, they were prepared following a similar protocol as for Au plates except that there was not a step of DSU coating due the efficient direct binding of proteins to glass, so that IgG and BSA were dropped onto the glass plate directly for binding agent coating and blocking.

Preparation of Beads:

Both 40 nm and 1 μm streptavidin-beads were kept in 1% (w/v) stock solution and added into BSA solution (4% in PBS) overnight at 4° C. for blocking, forming a working solution with a final concentration of beads at 0.1% (w/v). The final molar concentration for 40 nm beads is 50 nM, and for 1 μm beads is 32 pM.

Assay Steps:

For each assay with different plate and bead solution:
(1) 1 μL blocked bead solution was dropped onto the binding site of the assay plate (Au or glass plate);
(2) An X-plate was then put on top of the assay plate with the spacer pillars facing toward the deposited bead solution, and the two plates were pressed against each other by hand, and then left "self-held" in the closed configuration for a certain amount of time of assay incubation;
(3) After the incubation, the X-plate was peeled off and the assay plate was washed in PBST for 1 min and then in $H_2O$ for 1 min, after which fluorescence measurement was taken with the assay plate.

Figure 8:
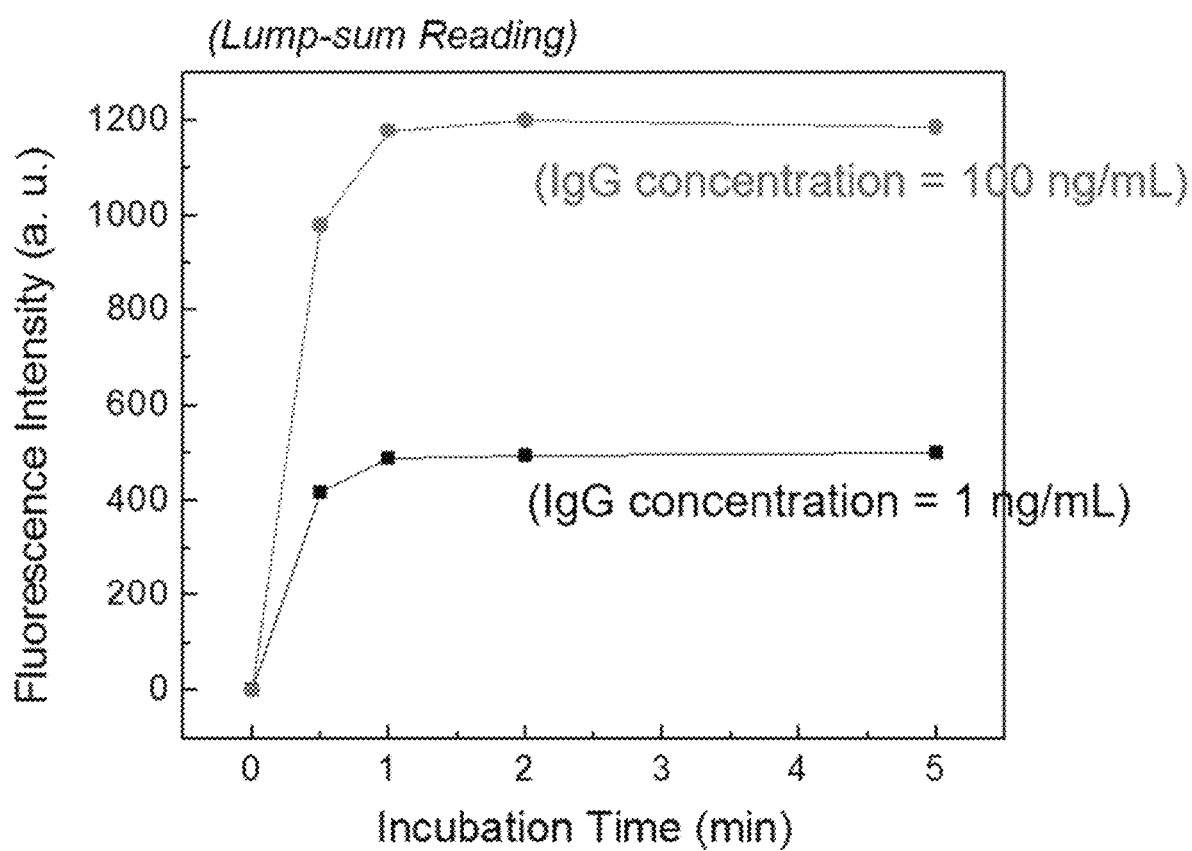
FIG. 8 shows the relationship between measured fluorescence intensity and incubation time in assays using Au plate (plate with gold surface) and 40 nm beads for two different binding agent concentrations.

Results:

FIG. 8 shows the relationship between measured fluorescence intensity and incubation time in assays using Au plate (plate with gold surface) and 40 nm beads for two different binding agent concentrations. Fluorescent signal in this experiment was detected using a "lump-sum" method. Black squares are data points collected from plates coated with 1 ng/mL (7 pM) IgG, and red filled circles are data points from plates coated with 100 ng/mL (700 pM) IgG. For both conditions, the fluorescent signal significantly increased as the incubation time was increased from 0 min to 1 min, however, it remained relatively stable when the incubation time exceeded 1 min. This data suggests that the saturation time for the assays using Au plate, under the experimental condition, is between 30 sec and 1 min, regardless whether 1 ng/mL or 100 ng/mL of IgG was coated on the binding site.

Figure 9:
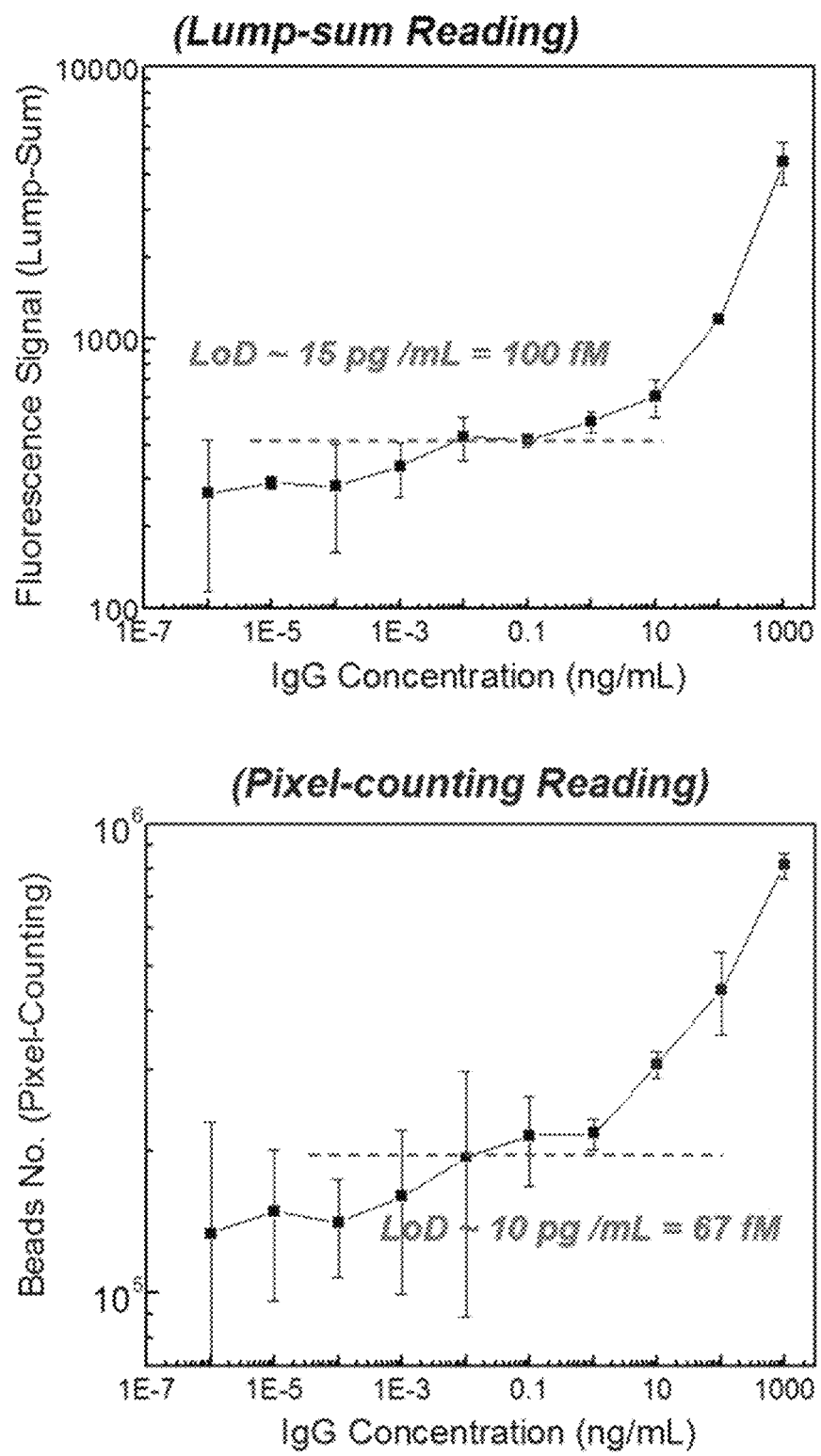
FIG. 9 shows the relationship between measured fluorescence intensity and IgG concentration, as well as the limit of detection (LoD) in assays using Au plate and 40 nm beads with 1-min incubation time.

FIG. 9 shows the relationship between measured fluorescence intensity and IgG concentration, as well as the limit of detection (LoD) in assays using Au plate and 40 nm beads with 1-min incubation time. Here, Au plates coated with different concentration of IgG were tested under the same condition, and fluorescent signal was detected using both "lump-sum" (a) and "pixel-counting" (b) methods. As shown in both plots, the fluorescent signal increased as a function of the concentration of IgG used to coat the plate. Under the experimental condition, LoD of IgG for the assay is around 15 pg/mL (100 fM) when the "lump-sum" method was used, and it is around 10 pg/mL (67 fM) when the "pixel-counting" method was used. LoD was determined as the IgG concentration corresponding to the fluorescent signal that is equal to the background optical noise plus three times of its standard deviation. Error bars are the standard deviation, calculated from the measurements at five different sample areas for each concentration.

Table 1 lists the raw data from the experiments that determined the LoD for assays using Au plate and "pixel-counting" detection method. In this table, "Total IgG coated" was calculated by multiplying the concentration and volume of the IgG solution used to prepare the plates, assuming all the IgG molecules in the solution were bound to the plate. "Average IgG distance" was then calculated by averaging the surface area of the Au plate over the number of IgG molecules. "Total Beads added" was calculated by multiplying the concentration and volume of the bead solution loaded to the Au plate during the assay. "Estimated Total Beads Captured" was estimated based on the pixel counting and the counting area. Two different types of "Capture Rate" were calculated, one is a quotient of "Estimated Total Beads Captured" and the number of "Total beads", and the other is a quotient of "Estimated Total Beads Captured" and the number of "Total IgG coated". "Captured beads average distance" was calculated by averaging the surface area of the Au plate over "Estimated Total Beads Captured".

TABLE 1

Raw data from LoD determination experiments with Au plates

| | Experimental Setup | | | | | | Experimental Results | | | |
|---|---|---|---|---|---|---|---|---|---|---|
| Chip Size | IgG Conc. (pM) | IgG volume | Total IgG coated | Average IgG distance (nm) | Beads Conc. (pM) | Total Beads added | Estimated Total Beads Captured | Capture Rate (Capture beads/ Total beads) | Capture Rate (Capture beads/ Total IgG) | Captured beads average distance (nm) |
| 3.5 mm × 3.5 mm | 6.7E+03 | 10 ul | 4.0E+10 | 17 | 5.0E+04 | 1.1E+10 | 815360 | 0.0074% | 0.0020% | 3876 |
| | 6.7E+02 | 10 ul | 4.0E+09 | 55 | 5.0E+04 | 1.1E+10 | 445138 | 0.0040% | 0.0111% | 5246 |
| | 6.7E+01 | 10 ul | 4.0E+08 | 175 | 5.0E+04 | 1.1E+10 | 307796 | 0.0028% | 0.0767% | 6309 |
| | 6.7E+00 | 10 ul | 4.0E+07 | 552 | 5.0E+04 | 1.1E+10 | 218213 | 0.0020% | 0.5437% | 7493 |
| | 6.7E−01 | 10 ul | 4.0E+06 | 1747 | 5.0E+04 | 1.1E+10 | 216036 | 0.0020% | 5% | 7530 |
| | 6.7E−02 | 10 ul | 4.0E+05 | 5525 | 5.0E+04 | 1.1E+10 | 193822 | 0.0018% | 48% | 7950 |
| | 6.7E−03 | 10 ul | 4.0E+04 | 17471 | 5.0E+04 | 1.1E+10 | 160284 | 0.0014% | N.A | 8742 |
| | 6.7E−04 | 10 ul | 4.0E+03 | 55248 | 5.0E+04 | 1.1E+10 | 141120 | 0.0013% | N.A | 9317 |
| | 6.7E−05 | 10 ul | 4.0E+02 | 174709 | 5.0E+04 | 1.1E+10 | 148960 | 0.0013% | N.A | 9068 |
| | 6.7E−06 | 10 ul | 4.0E+01 | 552479 | 5.0E+04 | 1.1E+10 | 133716 | 0.0012% | N.A | 9571 |
| | Background | 10 ul | 0.0E+00 | 0 | 5.0E+04 | 1.1E+10 | 90596 | 0.0008% | N.A | 11628 |

Figure 10:
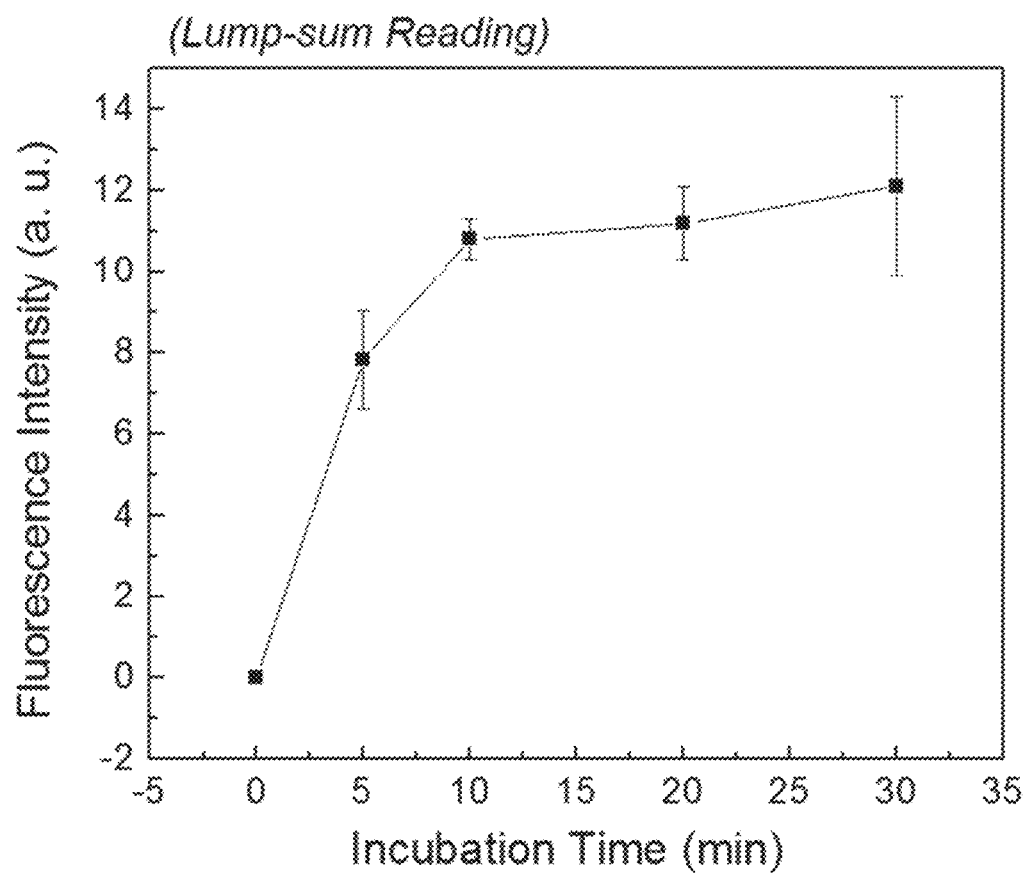
FIG. 10 shows the relationship between measured fluorescence intensity and incubation time in assays using glass plate and 1 μm beads.

FIG. 10 shows the relationship between measured fluorescence intensity and incubation time in assays using glass plate and 1 μm beads. Here, glass plates coated with 1 ug/mL (67 nM) of IgG were tested in assays with a series of different incubation time. Fluorescent signal was detected using a "lump-sum" method. As shown in the plot, the fluorescent signal significantly increased as incubation time was increased from 0 min to 10 min, but it remained relatively stable when incubation time exceeded 10 min. This data suggests that the saturation time for these assays using glass plate, under the experimental condition, is between 5 min and 10 min. Error bars are the standard deviation, calculated from the measurements at five different sample areas for each concentration.

Figure 11:
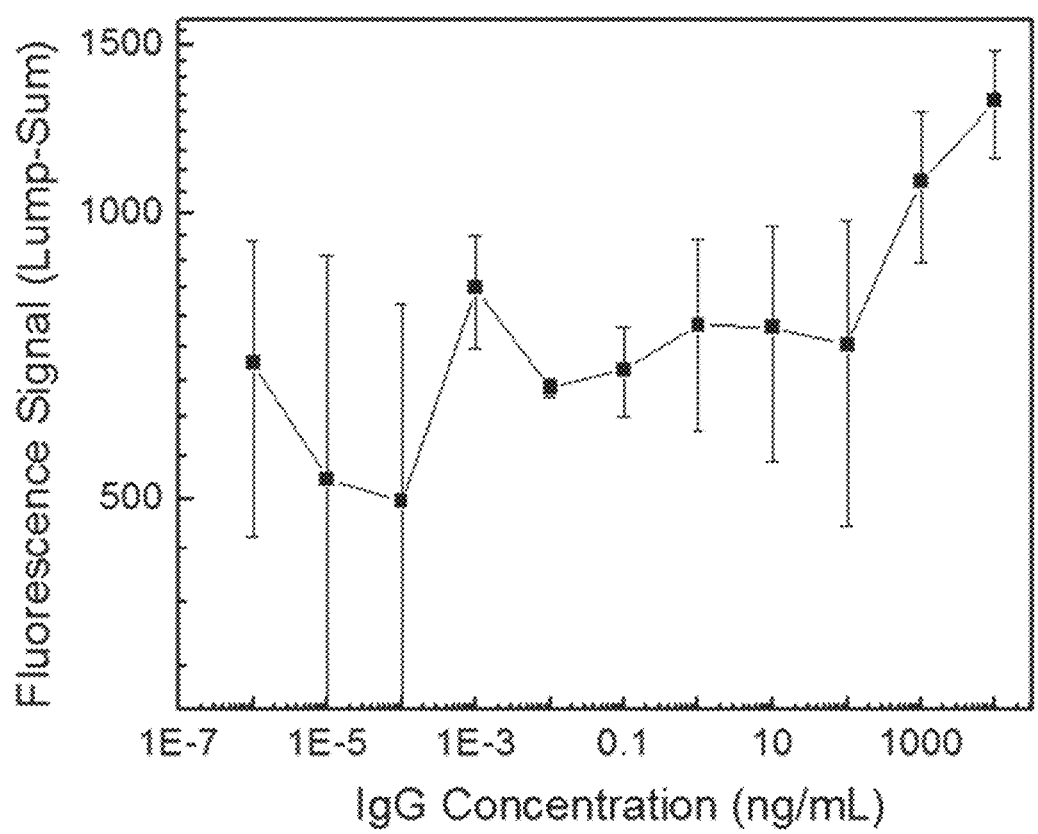
FIG. 11 shows the relationship between measured fluorescence intensity and IgG concentration, as well as the limit of detection (LoD) in assays using glass plate and 1 μm beads with 10-min incubation time.

FIG. 11 shows the relationship between measured fluorescence intensity and IgG concentration, as well as the limit of detection (LoD) in assays using glass plate and 1 μm beads with 10-min incubation time. Here, glass plates coated with different concentration of IgG were tested under the same condition, and the fluorescent signal was detected using the "lump-sum" method. As shown in the plot, there was a trend that the fluorescent signal increased as a function of the concentration of IgG used to coat the plate. The signal fluctuated around a low level in the low IgG concentration range, but it increased significantly when the IgG concentration was beyond 100 ng/mL. Based on these data, it is therefore determined that under the experimental condition, LoD of IgG is around 100 ng/mL (667 pM) for the assay. LoD was determined as above. Error bars are the standard deviation, calculated from the measurements at five different sample areas for each concentration.

Examples of Present Invention

A1. A device for analyzing a liquid sample, comprising:
a first plate, a second plate, and a nanoparticle label, wherein:
i. the first plate and second plate are movable relative to each other into different configurations,
ii. each plate respectively comprises an inner surface that has a sample contact area for contacting a liquid sample that contains a target analyte,
iii. one or both of the plates comprise, in a respective sample contact area, one or a plurality of binding sites that have a predetermined area and are coated with a binding agent, and
iv. the nanoparticle label comprises two interconnected parts: a nanoparticle and a detection agent;
wherein one of the configurations is a closed configuration, in which: the two plates are configured to confine at least part of the sample into a thin layer between their inner surfaces, which has a thickness of 250 μm or less and substantially less than the average linear dimension of the predetermined area of the binding site; and the nanoparticle label is in the thin layer; and
wherein the detection agent and the binding agent are configured to bind to each other either directly or indirectly, and the binding between the detection agent and the binding agent is configured to change a detectable signal related to the nanoparticle label.

B1. A device for analyzing a liquid sample, comprising:
a first plate, a second plate, spacers, and a nanoparticle label, wherein:
i. the first plate and second plate are movable relative to each other into different configurations,
ii. each plate respectively comprises, on its respective inner surface, a sample contact area for contacting a liquid sample that contains a target analyte,
iii. one or both of the plates comprise, in a respective sample contact area, one or a plurality of binding sites that have a predetermined area and are coated with a binding agent,
iv. one or both of the plates comprise the spacers that are fixed with the respective inner surface, wherein the spacers have a predetermined substantially uniform height and a predetermined constant inter-spacer distance, and at least one of the spacers is inside the sample contact area, and
v. the nanoparticle label comprises two interconnected parts: a nanoparticle and a detection agent;
wherein the detection agent and the binding agent are configured to bind to each other either directly or indirectly, and the binding between the detection agent and the binding agent is configured to change a detectable signal related to the nanoparticle label;
wherein in the direct binding, the detection agent is configured to directly bind to the binding agent, and either the detection agent or the binding agent is configured to bind to the target analyte, which competitively inhibits the binding between the detection agent and the binding agent;

wherein in the indirect binding, the detection agent and the binding agent are configured to bind to the target analyte at different locations thereof, forming the indirect binding through the mediation of the target analyte;

wherein in the open configuration, the two plates are partially or entirely separated apart and the spacing between the plates is not regulated by the spacers;

wherein in the closed configuration, which is configured after sample deposition in the open configuration, the thickness of a relevant volume of the deposited sample is reduced, compared to that in the open configuration of the plates, into a layer of substantially uniform thickness that is confined by the inner surfaces of the plates and in touch with the binding site; the uniform thickness of the layer is regulated by the plates and the spacers, and is 250 µm or less and substantially less than the average linear dimension of the predetermined area of the binding site; and the nanoparticle label is in the layer of uniform thickness; and wherein the relevant volume is a portion or an entire volume of the sample.

C1. A method of analyzing a liquid sample using nanoparticle label, comprising the steps of:

(a) providing a first plate, a second plate, and a spacing mechanism, wherein:
  i. the first plate and second plate are movable relative to each other into different configurations;
  ii. each plate respectively comprises, on its respective inner surface, a sample contact area for contacting a liquid sample;
  iii. one or both of the plates comprise, in a respective sample contact area, one or a plurality of binding sites that have a predetermined area and is coated with a binding agent; and
  iv. the spacing mechanism is configured to regulate the spacing between the first plate and the second plate in the closed configuration;

(b) adding a nanoparticle label to a liquid sample to form a label solution,
  wherein the nanoparticle label comprises two interconnected parts: a nanoparticle and a detection agent,
  wherein the detection agent and the binding agent are configured to bind to each other either directly or indirectly, and the binding between the detection agent and the binding agent is configured to change a detectable signal related to the nanoparticle label;
    wherein in the direct binding, the detection agent is configured to directly bind to the binding agent, and either the detection agent or the binding agent is configured to bind to the target analyte, which competitively inhibits the binding between the detection agent and the binding agent, and
    wherein in the indirect binding, the detection agent and the binding agent are configured to bind to the target analyte at different locations thereof, forming the indirect binding through the mediation of the target analyte;

(c) depositing the label solution on the inner surface of at least one of the two plates when the two plates are configured in an open configuration, in which: the two plates are partially or entirely separated apart and the spacing between the plates is not regulated by the spacing mechanism; and (d) compressing a relevant volume of the deposited label solution by bringing the two plates into a closed configuration, in which: the thickness of the relevant volume of the deposited label solution is reduced, compared to that in the open configuration of the plates, into a thin layer that is confined by the inner surfaces of the plates and in touch with the binding site; the reduced thickness of the layer is regulated by the plates and the spacing mechanism, and is 250 µm or less and substantially less than the average linear dimension of the predetermined area of the binding site; and the nanoparticle label is in the thin layer, wherein the relevant volume is a portion or an entire volume of the label solution; and wherein reducing the thickness of the relevant volume of the label solution reduces the time for the binding between the binding agent and the nanoparticle label to reach equilibrium.

D1. A method of analyzing a liquid sample using nanoparticle label, comprising the steps of:

(e) providing a first plate, a second plate, and spacers, wherein:
  v. the first plate and second plate are movable relative to each other into different configurations,
  vi. each plate respectively comprises, on its respective inner surface, a sample contact area for contacting a liquid sample that contains a target analyte,
  vii. one or both of the plates comprise, in a respective sample contact area, one or a plurality of binding sites that have a predetermined area and is coated with a binding agent, and
  viii. one or both of the plates comprise the spacers that are fixed with the respective inner surface, wherein the spacers have a predetermined substantially uniform height and a predetermined constant interspacer distance, and at least one of the spacers is inside the sample contact area;

(f) adding a nanoparticle label to the sample to form a label solution,
  wherein the nanoparticle label comprises two interconnected parts: a nanoparticle and a detection agent, and
  wherein the detection agent and the binding agent are configured to bind to each other either directly or indirectly, and the binding between the detection agent and the binding agent is configured to change a detectable signal related to the nanoparticle label;
    wherein in the direct binding, the detection agent is configured to directly bind to the binding agent, and either the detection agent or the binding agent is configured to bind to the target analyte, which competitively inhibits the binding between the detection agent and the binding agent, and
    wherein in the indirect binding, the detection agent and the binding agent are configured to bind to the target analyte at different locations thereof, forming the indirect binding through the mediation of the target analyte;

(g) depositing the label solution on the inner surface of at least one of the two plates when the two plates are configured in an open configuration, in which: the two plates are partially or entirely separated apart and the spacing between the plates is not regulated by the spacers; and (h) compressing a relevant volume of the deposited label solution by bringing the two plates into a closed configuration, in which: the thickness of the relevant volume of the deposited label solution is reduced, compared to that in the open configuration of the plates, into a layer of substantially uniform thickness that is confined by the inner surfaces of the plates and in touch with the binding site; the uniform thickness of the layer is regulated by the plates and the spacers, and is 250 µm or less and substantially less than the average linear dimension of the predetermined area of the binding site; and the nanoparticle labels is in the layer of uniform thickness, wherein the relevant volume is a portion or an entire volume of the label solution; and wherein reducing the thickness of the relevant volume of the label solution reduces the time for the binding between the binding agent and the nanoparticle label to reach equilibrium.

A2. The device of embodiment A1, wherein the nanoparticle label is attached on the inner surface of one of the plates, and configured to be released and diffuse in the sample upon contacting the sample.

A3. The device of any one of embodiment A1 or A2, wherein in the direct binding, the detection agent is configured to directly bind to the binding agent, and either the detection agent or the binding agent is configured to bind to the target analyte, which competitively inhibits the binding between the detection agent and the binding agent.

A4. The device of any one of prior embodiments, wherein in the indirect binding, the detection agent and the binding agent are configured to bind to the target analyte at different locations thereof, forming the indirect binding through the mediation of the target analyte.

A5. The device of any one of prior embodiments, wherein the nanoparticle label-related signal comprises:
i. luminescence selected from photoluminescence, electroluminescence, and electrochemiluminescence;
ii. light absorption, reflection, transmission, diffraction, scattering, or diffusion;
iii. surface Raman scattering;
iv. electrical impedance selected from resistance, capacitance, and inductance;
v. magnetic relaxivity; or
vi. any combination of i-v.

A6. The device of any one of prior embodiments, further comprising a spacing mechanism that regulates the spacing between the two plates in the closed configuration.

A7. The device of any one of prior embodiments, wherein one of the configurations is an open configuration, in which: the two plates are partially or completely separated apart, and the spacing between the plates is not regulated by the spacing mechanism, allowing the sample to be deposited on one or both of the plates.

A8. The device of any one of prior embodiments, wherein the spacing mechanism comprises a plurality of spacers and in the closed configuration the spacers are positioned between the inner surfaces of the two plates.

A9. The device of embodiment A8, wherein the spacers have a maximum height of 250 µm or less.

A10. The device of embodiment A8, wherein the spacers have a predetermined substantially uniform height that is 250 µm or less.

A11. The device of any one of embodiments A8-A10, wherein the spacers have a predetermined constant inter-spacer distance.

A12. The device of any one of embodiments A8-A11, wherein the spacers are fixed with the respective inner surface of one or both of the plates.

A13. The device of any one of embodiments A8-A12, wherein at least one of the spacers is inside the sample contact area.

A14. The device of any one of embodiments A8-A13, wherein the thin layer has a substantially uniform thickness that is about the uniform height of the spacers.

C2. The method of embodiment C1, wherein the compressing in step (d) comprises:
bringing the two plates together; and
conformable pressing, either in parallel or sequentially, an area of at least one of the plates to press the plates together to the closed configuration, wherein the conformable pressing generates a substantially uniform pressure on the plates over the relevant volume of the label solution, and the pressing spreads the relevant volume of the label solution laterally between the sample contact surfaces of the plates.

C3. The method of any one of embodiment C1 or C2, wherein the compressing of step (d) is performed by human hand.

C4. The method of any one of embodiment C1 or C2, wherein the compressing of step (d) is provided by a pressured liquid, a pressed gas, or a conformal material.

C5. The method of any one of any prior method embodiments, wherein the nanoparticle label is attached on the inner surface of one of the plates, and configured to be released and diffuse in the sample upon contacting the sample.

C6. The method of embodiment C5, wherein the having step (b) comprises depositing the liquid sample on the inner surface of the plate that has the nanoparticle label attached on and having the nanoparticle label released into the sample to form the label solution.

C7. The method of any one of prior method embodiments, further comprising:
(e) after step (d) and while the plates are in the closed configuration, assessing the binding between the nanoparticle and the binding agent in a part or entirety of the thin layer, through analyzing the nanoparticle label-related signal, after incubating for a time that is about equal to or longer than the time that it takes for the nanoparticle label to diffuse across the thickness of the thin layer.

C8. The method of embodiment C7, wherein the nanoparticle label-related signal comprises:
i. luminescence selected from photoluminescence, electroluminescence, and electrochemiluminescence;
ii. light absorption, reflection, transmission, diffraction, scattering, or diffusion;
iii. surface Raman scattering;
iv. electrical impedance selected from resistance, capacitance, and inductance;
v. magnetic relaxivity; or
vi. any combination of i-v.

C9. The method of any one of prior method embodiments, wherein the spacing mechanism comprises a plurality of spacers and the spacers are positioned between the inner surfaces of the two plates in the closed configuration.

C10. The method of embodiment C9, wherein the spacers have a maximum height of 250 μm or less.

C11. The method of embodiment C9, wherein the spacers have a predetermined substantially uniform height that is 250 μm or less.

C12. The method of any one of embodiments C9-C11, wherein the spacers have a predetermined constant inter-spacer distance.

C13. The method of any one of embodiments C9-C12, wherein the spacers are fixed with the inner surface of one or both of the plates.

C14. The method of any one of embodiments C9-C13, wherein at least one of the spacers is inside the sample contact area.

C15. The method of any one of embodiments C9-C14, wherein the thin layer has a substantially uniform thickness that is about the uniform height of the spacers.

C16. The method of any one of prior method embodiments, further comprising one or more washing steps.

C17. The method of any one of prior method embodiments, wherein the liquid sample is made from a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

C18. The method of any one of prior method embodiments, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

C19. The method of any one of prior method embodiments, wherein the sample is an environmental gaseous sample from a source selected from the group consisting of: the air, underwater heat vents, industrial exhaust, vehicular exhaust, and any combination thereof.

C20. The method of any one of prior method embodiments, wherein the sample is a foodstuff sample selected from the group consisting of: raw ingredients, cooked food, plant and animal sources of food, pre-processed food, and partially or fully processed food, and any combination thereof.

D2. The method of embodiment D1, wherein the compressing in step (d) comprises:
bringing the two plates together; and
conformable pressing, either in parallel or sequentially, an area of at least one of the plates to press the plates together to the closed configuration, wherein the conformable pressing generates a substantially uniform pressure on the plates over the relevant volume of the label solution, and the pressing spreads the relevant volume of the label solution laterally between the sample contact surfaces of the plates.

D3. The method of any one of embodiment D1 or D2, further comprising:
(i) after step (d) and while the plates are in the closed configuration, assessing the binding between the nanoparticle and the binding agent in a part or entirety of the layer of uniform thickness, through analyzing the nanoparticle label-related signal, after incubating for a time that is about equal to or longer than the time that it takes for the nanoparticle label to diffuse across the thickness of the uniform thickness layer.

D4. The method of embodiment D3, further comprising a step after step (d) and before step (e): after the plates are in the closed configuration, removing the conformable pressing force, wherein the thickness of the layer of uniform thickness after removal of the conformable pressing force: (i) is substantially the same as of the layer of uniform thickness before removing the conformable pressing force and (ii) deviates from the spacer height by less than 10%.

D5. The method of any one of embodiments D1-D4, wherein during the deposition of step (c), the amount of the label solution deposited on the plate is unknown.

E1. The device or method of any one of prior embodiments, wherein the time for the binding between the binding agent and the nanoparticle label to reach equilibrium is about equal to or less than 60 seconds.

E2. The device or method of any one of prior embodiments, wherein the ratio of the linear dimension of the binding site to the uniform thickness is larger than 5.

E3. The device or method of any one of prior embodiments, wherein the binding site is defined by a patch of dried reagent.

E4. The device or method of any one of prior embodiments, wherein the binding site is between a pair of electrodes.

E5. The device or method of any one of prior embodiments, wherein one or both plate sample contact surfaces comprise one or a plurality of amplification sites that are each capable of amplifying the nanoparticle label-related signal when the nanoparticle label is within 500 nm from an amplification site.

E6. The device or method of any one of prior embodiments, wherein the detection agent and the binding agent are molecules selected from the group consisting of: protein, peptide, peptidomimetics, streptavidin, biotin, oligonucleotide, oligonucleotide mimetics, any other affinity ligand and any combination thereof.

E7. The device or method of any one of prior embodiments, wherein the nanoparticle has a broadest dimension in the range of 1 nm to 5 μm.

E8. The device or method of any one of prior embodiments, the nanoparticle has a broadest dimension in the range of 1 nm to 200 nm.

E9. The device or method of any one of prior embodiments, wherein the nanoparticle is selected from the group consisting of: carbon nanotubes, fullerenes, dendrimers, quantum dots, noble metal nanoparticles, fluorophore-doped nanoparticles, rare earth-doped nanoparticles, superparamagnetic nanoparticles, and any combination thereof.

E10. The device or method of any one of prior embodiments, wherein the plates have a thickness of less than 200 μm.

E11. The device or method of any one of prior embodiments, wherein the plates have a thickness of less than 100 μm.

E12. The device or method of any one of prior embodiments, wherein each of the plates has an area of less than 5 cm$^2$.

E13. The device or method of any one of prior embodiments, wherein each of the plates has an area of less than 2 cm$^2$.

E14. The device or method of any one of prior embodiments, wherein at least one of the plates is partially or entirely transparent.

E15. The device or method of any one of prior embodiments, wherein at least one of the plates is made from a flexible polymer.

E16. The device or method of any one of prior embodiments, wherein at least one of the plates is a flexible plate, and the thickness of the flexible plate times the Young's modulus of the flexible plate is in the range of 60 to 75 GPa-μm.

E17. The device or method of any one of prior embodiments, wherein the uniform height of the pillars is in the range of 0.5 to 100 μm.

E18. The device or method of any one of prior embodiments, wherein the uniform height is in the range of 0.5 to 20 μm.

E19. The device or method of any one of prior embodiments, wherein the constant inter-spacer distance of the pillars is in the range of 7 to 50 μm.

E20. The device or method of any one of prior embodiments, wherein the constant inter-spacer distance of the pillars is in the range of 5 to 200 μm.

E21. The device or method of any one of prior embodiments, wherein the spacers are pillars with a cross sectional shape selected from round, polygonal, circular, square, rectangular, oval, elliptical, or any combination of the same.

E22. The device or method of any one of prior embodiments, wherein the spacers have a pillar shape and a substantially flat top surface, wherein, for each spacer, the ratio of the lateral dimension of the spacer to its height is at least 1.

E23. The device or method of any one of prior embodiments, wherein each spacer has the ratio of the lateral dimension of the spacer to its height is at least 1.

E24. The device or method of any one of prior embodiments, wherein the minimum lateral dimension of spacer is less than or substantially equal to the minimum dimension of a target analyte in the sample.

E25. The device or method of any one of prior embodiments, wherein the spacers have a pillar shape, and the sidewall corners of the spacers have a round shape with a radius of curvature at least 1 μm.

E26. The device or method of any one of prior embodiments, wherein the spacers have a density of at least 100/mm$^2$.

E27. The device or method of any one of prior embodiments, wherein the spacers have a density of at least 1000/mm$^2$.

E28. The device or method of any one of prior embodiments, wherein the spacers have a filling factor of at least 1%, wherein the filling factor is the ratio of the spacer area in contact with the layer of uniform thickness to the total plate area in contact with the layer of uniform thickness.

E29. The device or method of any one of prior embodiments, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

E30. The device or method of any one of prior embodiments, wherein
at least one of the plates is flexible, and
for the flexible plate, the fourth power of the inter-spacer-distance (ISD) divided by the thickness of the flexible plate (h) and the Young's modulus (E) of the flexible plate, $ISD^4/(hE)$, is equal to or less than 106 um$^3$/GPa.

E31. The device or method of any one of prior embodiments, wherein the spacers are fixed on a plate by directly embossing the plate or injection molding of the plate.

E32. The device or method of any one of prior embodiments, wherein the materials of the plate and the spacers are independently selected from polystyrene, PMMG, PC, COC, COP, or another plastic.

C. Cell Lysing and Selective (006)

In biological and chemical assays, it is sometimes necessary to target specific cell types in a sample. For example, in some assays it would be desirable to selectively lyse certain cell types but leave the other cell types un-lysed, so that one or more intracellular components of the lysed cells are analyzed; in other assays, it would be desirable to selectively lyse certain cell types but leave the other cell types un-lysed, so that certain properties, e.g. cell numbers, of the un-lysed cells can be analyzed. The devices and methods to selectively lyse specific cell types, especially with regard to high uniformity in lysing, need to be developed.

The present invention provides a solution to the problem of selectively lysing specific cell types in a sample. In some embodiments, cells are lysed by mechanical stress using two parallel plates. With spacing mechanisms such as but not limited to spacers fixed on one or both of the plates, the plates are compressed to produce a gap between the plates. With the present invention, the gaps between the plates are substantially uniform (e.g. small variation in gap size) over a substantial area, leading to highly selective and uniform lysing results. There is no existing device or method that can achieve such results. In traditional cell lysing devices, the lysing is not uniform, in a large part due to the lack of uniformity of gap size. The non-uniformity of gap size in traditional mechanical lysing devices is caused by one or any combinations of the following factors: (a) using unfixed beads as spacers, (b) using rigid plate(s), and (c) applying non-uniform pressing force.

One aspect of the present invention provides uniformity of gap size between two plates, hence leading to uniform lysing of specific cell types over a significant area.

Another aspect of the present invention is to selectively lyse one type of cells in a liquid sample, while other types of cells in the sample are left un-lysed.

Another aspect of the present invention is to lyse one or more types of cells in a liquid solution at a select area of one plate, while the same cell type is un-lysed in other areas of the plate.

DETAILED DESCRIPTION OF EXEMPLARY EMBODIMENTS

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

QMAX Device, Selective Lysing, and Location-Specific Selective Lysing

Figure 12:
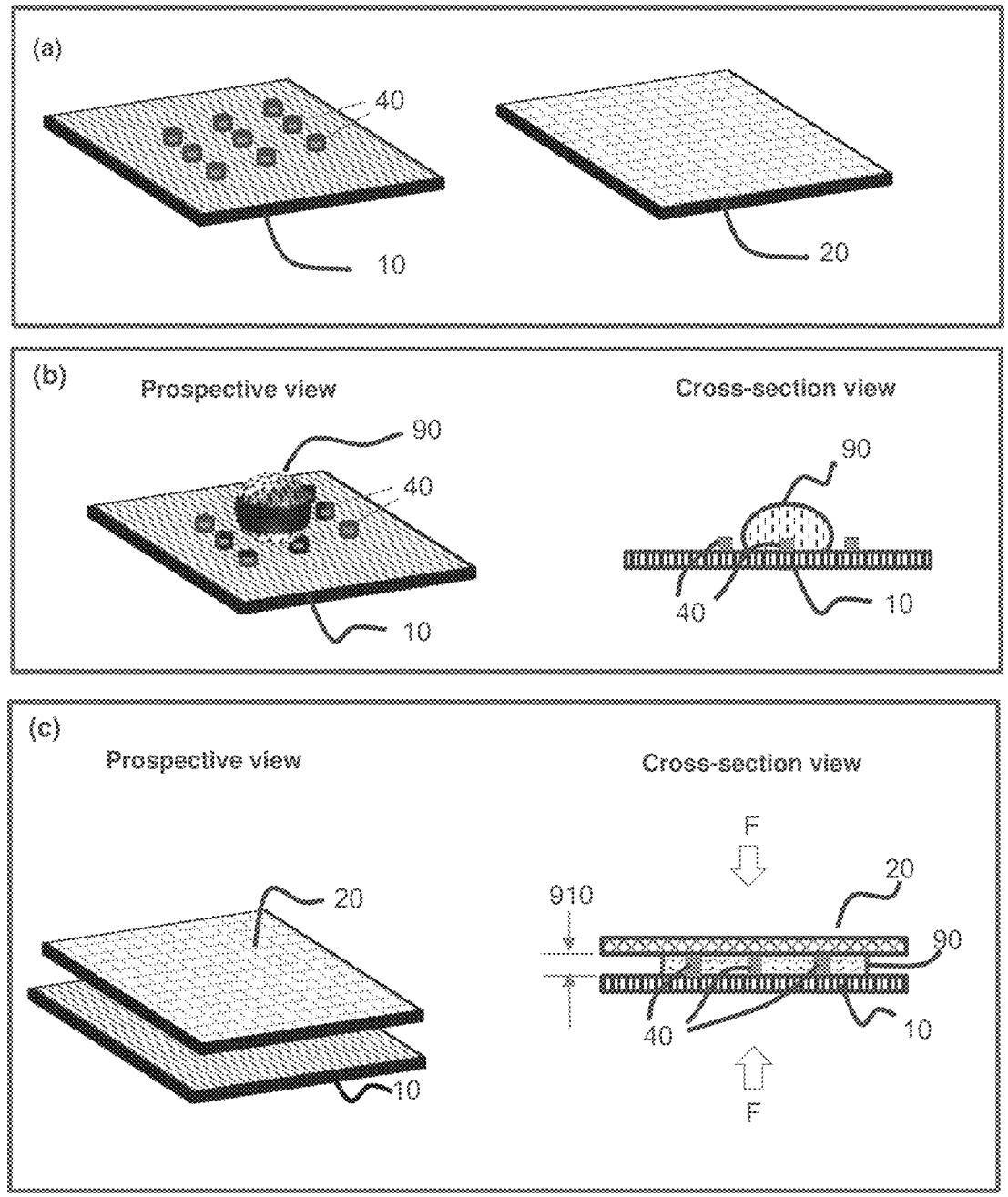
FIG. 12 illustrates an embodiment of a QMAX (Q: quantification; M: magnifying; A: adding reagents; X: acceleration; also known as compressed regulated open flow (CROF)) device. Panel (A) shows a prospective view of a first plate, a second plate and spacers; panel (B) shows prospective and sectional views of depositing a sample on one of the plates; panel (C) shows using the first plate and the second plate to compress the sample into a layer of uniform thickness, which is regulated by the height of the spacers.

FIG. 12 shows an embodiment of a QMAX (Q: quantification; M: magnifying; A: adding reagents; X: acceleration; also known as compressed regulated open flow (CROF)) device, which comprises a first plate 10 and a second plate 20. In particular, panel (A) shows the perspective view of a first plate 10 and a second plate 20 wherein spacers 40 are fixed to the first plate 10. It should be noted, however, that in some embodiments the spacers 40 are also fixed on the second plate 20 or on both the first plate 10 and the second plate 20. Panel (B) shows the perspective view and a sectional view of depositing a sample 90 on the first plate 10 at an open configuration. It should be noted, however, that in some embodiments the sample 90 is deposited on the second plate 20, or on both the first plate 10 and the second plate 20. In some embodiments, each plate comprises a sample contact area for contacting the sample. In some embodiments, the sample contact area occupies part or the entirety of the inner surface of the respective plate. In some embodiments, the inner surface is also termed sample surface. In some embodiments, at least a portion of the spacers 40 are located in the sample contact area. Panel (C) illustrates (i) using the first plate 10 and second plate 20 to spread the sample 90 (the sample flow between the inner surfaces of the plates) and reduce the sample thickness, and (ii) using the spacers 40 and the plate 10 and 20 to regulate the sample thickness at the closed configuration of the QMAX device. In some embodiments, the inner surface of each plate has one or a plurality of binding sites and or storage sites (not shown). In some embodiments, the spacers 40 are permanently fixed on one or both of the plates 10 and 20. Herein the term "permanently fixed" means that the spacers are attached to a plate and the attachment is maintained during one or more uses of the plate.

In some embodiments, the device in the present invention includes but is not limited to the QMAX device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the disclosures of which are hereby incorporated in their entireties by reference for all purposes. In some embodiments, the QMAX device is termed a QMAX card when the plates are connected, e.g. by a hinge.

Examples of Selective Lysing Using the QMAX Device

Figure 13:
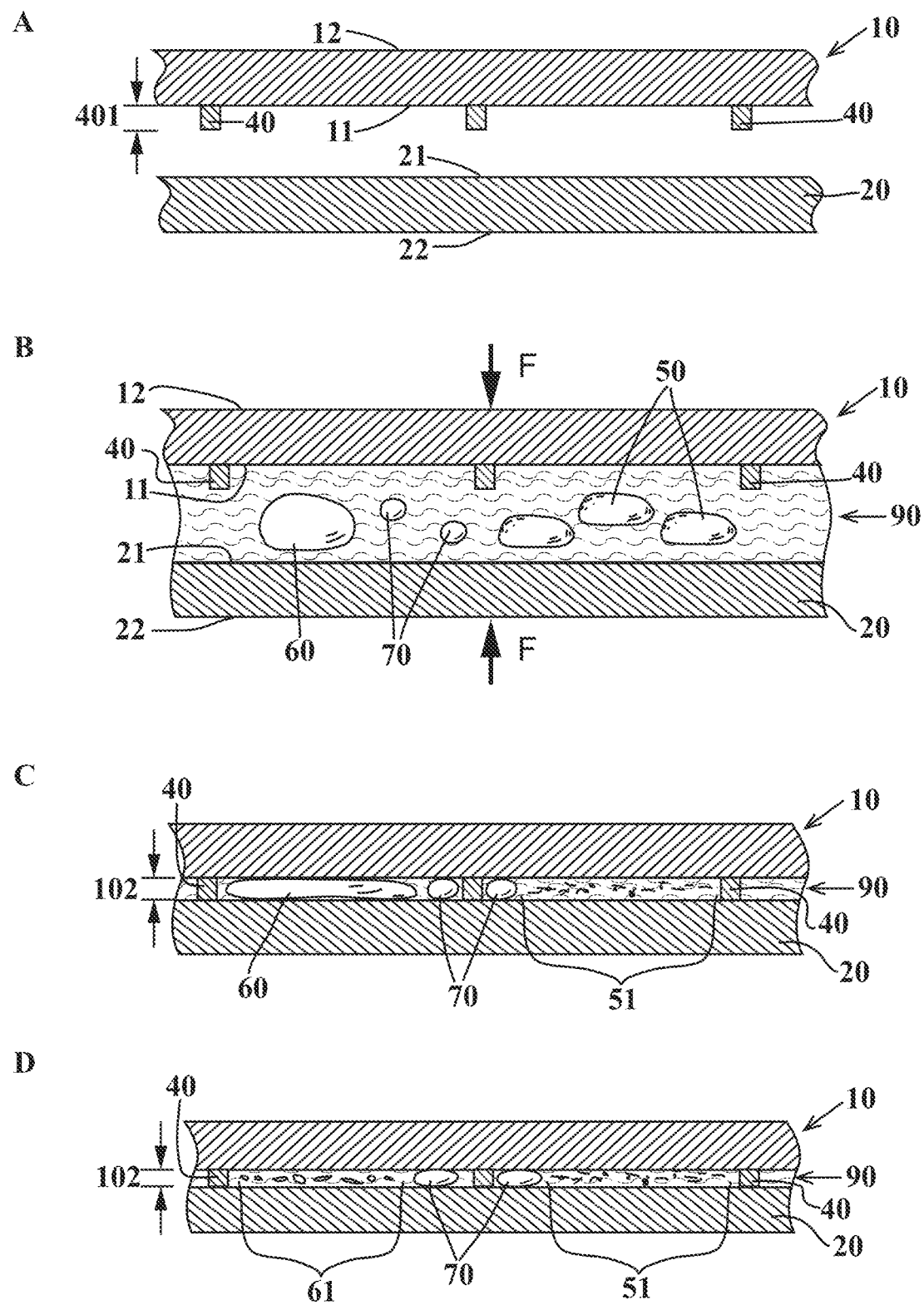
FIG. 13 illustrates sectional views of exemplary embodiments of the present invention. Panel (A) illustrates part of a QMAX device before any sample is added; panel (B) illustrates the QMAX device after a liquid sample has been added but before the plates have been fully compressed; panel (C) illustrates the device after the compressing has been completed and certain cell types have been lysed; panel (D) illustrates the device with a different spacer height compared to panel (C) after the compressing has been completed and certain cell types have been lysed.
Figure 14:
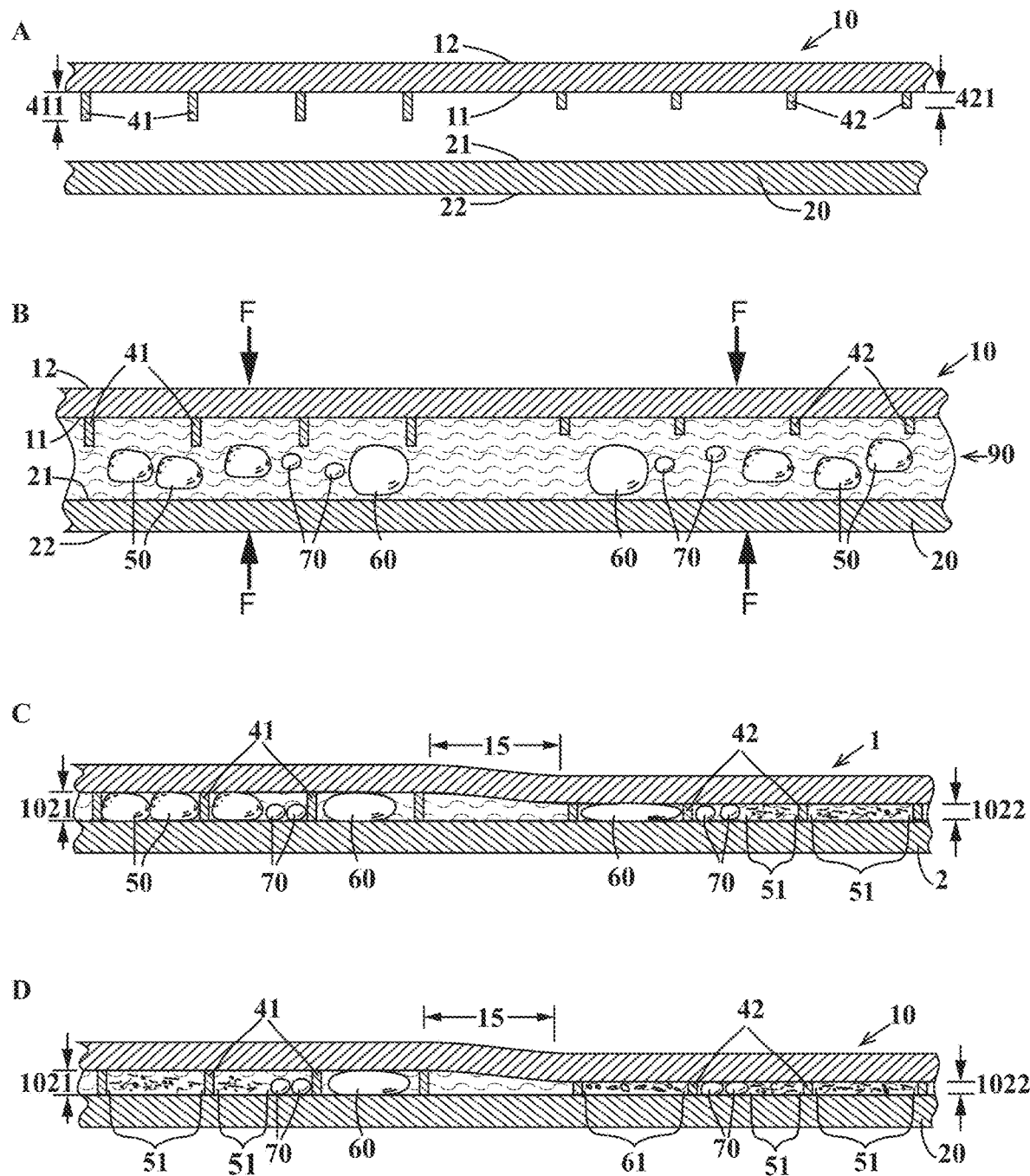
FIG. 14 illustrates sectional views of other exemplary embodiments of the present invention, where spacers at different locations have different heights; panel (A) illustrates a device having two sets of spacers with different heights before any sample is added; panel (B) illustrates the device after a liquid sample has been added but before the plates have been fully compressed; panel (C) illustrates the device after the compressing has been completed and certain cells types have been lysed in one location but not the other; panel (D) illustrates the device with different spacer heights compared to panel (C), after the compressing has been completed, and different cell types have been lysed in different locations.

FIGS. 13-14 illustrate some exemplary embodiments of the QMAX device, which is used for selective lysing one or more components in a sample that comprises multiple components. The features as stated for the QMAX device as shown in FIG. 12 and described thereof, are also applicable to the embodiments shown in FIGS. 13-14 and described thereof. In addition, it should be noted that the QMAX device serves as an example, not a limiting factor, for the features shown in FIGS. 13-14 and described thereof. Besides the QMAX device, such features, especially the features related to selective lysing, are also applicable to other devices, instruments and structures.

FIG. 13 shows sectional and partial views of exemplary embodiments of the present invention. As shown in panel (A) of FIG. 13, the device comprises a first plate 10 and a second plate 20, wherein the first plate 10 comprises a first plate inner surface 11 and a first plate outer surface 12, and the second plate 20 comprises a second plate inner surface 21 and a second plate outer surface 22. The device further comprises spacers 40 that have a uniform height 401. In panel (A), the spacers 40 are fixed on the first plate 10; however, it should be noted that in some embodiments the spacers 40 are fixed on the second plate 20, or on both the first plate 10 and the second plate 20.

In some embodiments, the plates 10 and 20 are moveable relative to each other into different configurations. One of the configurations is an open configuration, in which the two plates 10 and 20 are partially or entirely separated apart and the spacing between the plates 10 and 20 is not regulated by the spacers 40. Referring to panel (B) of FIG. 12 and also panel (A) of FIG. 13, in the open configuration, a sample 90 is deposited on one or both of the plates. Another of the configurations is a closed configuration. Referring to panel (C) of FIG. 12 and also panel (C) of FIG. 2, in the closed configuration: at least part of the sample 90 is compressed by the two plates 10 and 20 into a layer of uniform thickness, and the layer is confined by the inner surfaces 11 and 21 of the two plates 10 and 20 and is regulated by the spacers 40. Although FIG. 12 shows the plates 10 and 20 to be not connected, it should be noted that in some embodiments the device of the present invention further comprises connecting structures, such as but not limited to hinges and joints, which are used to connect the first plate 10 and the second plate 20 and allow the plates to switch between the open configuration and the closed configuration.

As shown in panel (B) of FIG. 13, the device of the present invention comprises a first plate 10 and a second plate 20, wherein the first plate 10 comprises a first plate inner surface 11 and a first plate outer surface 12, and the second plate 20 comprises a second plate inner surface 21 and a second plate outer surface 22. Referring to panel (B) of FIG. 12, in some embodiments, in the open configuration, a liquid sample 90 is added to one of the plates or both of the plates. Further referring to panel (C) of FIG. 12 and panel (B) of FIG. 13, the two plates 10 and 20 are compressed so that the sample 90 is confined by the first plate 10 and second plate 20. Panel (B) of FIG. 13 shows that the two plates are being compressed, but before the plates have been fully switched to a closed configuration. In panel (B) of FIG. 13, the first plate inner surface 11 and the second plate inner surface 21 are facing each other, a compressing force F is being applied to the plates, the sample 90 is spreading and flowing on the plates, but the spacing between the plates 10 and 20 and the thickness of the sample 90 are not regulated by the height of the spacers 40.

As shown in panel (B) of FIG. 13, the sample 90 comprises multiple components. For illustrative purposes, the sample 90 shown in panel (B) of FIG. 13 comprises at least a first component 50, a second component 60, and a third component 70. In some embodiments, the first component 50, the second component 60, and the third component 70 are cells and each component represents a different cell type. Besides the cell components, the sample 90 also comprises a liquid component.

In some embodiments, it would be possible to conformable press, either in parallel or sequentially, the QMAX device into a closed configuration. Conformable pressing is a method that makes the pressure applied over an area to be substantially constant regardless of the shape variation of the outer surfaces of the plates; In particular, parallel conformable pressing applies the pressures on the intended area at the same time, and sequential conformable pressing applies the pressure on a part of the intended area and gradually move to other area. In some embodiments, conformable pressing is applied by human hand, air blow, liquid pressure, or other forces.

Panel (C) of FIG. 13 illustrates the device of the present invention after the compressing has been completed and certain cell types have been lysed. As shown in panel (C), the device is in a closed configuration. In the closed configuration, the spacing 102 between the two plates 10 and 20 are regulated by the spacers 40; in some embodiments, the spacing 102 is uniform and is substantially the same as the uniform height of the spacers 40. The closed configuration is a configuration after deposition of the sample 90 in the open configuration; in the closed configuration, at least part of the sample 90 is compressed by the two plates 10 and 20 into a layer of uniform thickness, and the layer is confined by inner surfaces 11 and 21 of the two plates 10 and 20 and is regulated by the spacers 40.

In some embodiments, the spacers 40 have a uniform height and the layer of sample 90 in the closed configuration has a uniform thickness that is substantially the same as the uniform height of the spacers 40. Herein, the term "substantially the same" refers to a difference that is less than 20%, 15%, 10%, 9%, 8%, 7%, 6%, 5%, 4%, 3%, 2%, 1%, 0.5%, or 0.1%, or in a range between any of the two values. In some embodiments, the spacer height, the spacing between the plates (gap size), and/or the sample thickness is equal to or less than 3 nm, 10 nm, 50 nm, 100 nm, 200 nm, 500 nm, 800 nm, 1000 nm, 1.2 µm, 1.4 µm, 1.5 µm, 1.6 µm, 1.8 µm, 2 µm, 3 µm, 5 µm, 10 µm, 20 µm, 30 µm, 50 µm, 100 µm, 150 µm, 200 µm, 300 µm, 500 µm, 800 µm, 1 mm, 2 mm, 4 mm, or in a range between any two of the values. In certain embodiments, the spacer height is less than 0.2 µm, 0.3 µm, 0.4 µm, 0.5 µm, 0.6 µm, 0.7 µm, 0.8 µm, 0.9 µm, 1 µm, 1.1 µm, 1.2 µm, 1.3 µm, 1.4 µm, 1.5 µm, 1.6 µm, 1.7 µm, 1.8 µm, 1.9 µm, 2 µm, 2.2 µm, 2.5 µm, 3 µm or 3.5 µm, or in a range between any two of the values. In some embodiments, the thickness variation of the layer of highly uniform thickness over the lateral area of the relevant volume is equal to or less than 40%, 30%, 20%, 15%, 10%, 7%, 5%, 3%, or 1%, or in a range between any of the two values, wherein the thickness variation is relative to the average thickness of the lateral area.

In some embodiments, the uniformity of the sample layer and/or the lysing results is also affected the distance between the spacers. In some embodiments, the spacers 40 are fixed to one or both of the plates. Using fixed spacers precisely control the inter-spacer distance. In certain embodiments, the spacers have a constant inter-spacer distance. In some embodiments, the distance between neighboring spacers (i.e. the inter-spacer distance) is equal to or less than 1 µm, 5 µm, 7 µm, 10 µm, 20 µm, 30 µm, 40 µm, 50 µm, 60 µm, 70 µm, 80 µm, 90 µm, 100 µm, 200 µm, 300 µm, 400 µm, 500 µm, 1 mm, 2 mm, 3 mm, 5 mm, 7 mm, 10 mm, or in any range between the values. In certain embodiments, the inter-spacer distance is in a range of 7-20 µm, 20-50 µm, 50-100 µm, 100-150 µm, 150-200 µm, or 200-500 µm.

As shown in panel (C) of FIG. 13, in some embodiments, the first component 50 has been lysed due to the compressing of the two plates 10 and 20. The cells of the first component 50 have become lysed debris 51 and no longer maintain a complete cell membrane with observable cell contours. With such lysing, the intracellular organelles and molecules in the cells of the first component 50 are disbursed in the sample 90 and exposed. In certain embodiments, the intracellular organelles and molecules of the first component become available for assaying. In some embodiments, as shown in panel (C) of FIG. 13, the second component 60 is un-lysed, but the cells of the second component 60 have been compressed and stretched due to the mechanical force exerted, at least in part, by the first plate 10 and the second plate 20. In some embodiments, as shown in panel (C) of FIG. 13, the third component 70 is un-lysed. In certain embodiments, the cells of the third component 70 are largely intact. In certain embodiments, with the lysing of the first component 50, it is advantageous to perform assays related to cell surface molecules of the second component 60 and/or the third component 70; it is also advantageous to perform assays related to un-lysed-cell properties, (e.g. cell number or expression of membrane bound molecules) second component 60 and/or the third component 70.

In certain embodiments, different cell types have different maximum and minimum natural dimensions. Herein the term "natural dimension" of a cell type refers to the average measurable size (in length) of a specific cell type that include either non-cultured cells in their natural in vivo conditions or cultured cells when they are suspended in a solution that mimics a state of physiological homeostasis. Depending on the shape and structure of different cell types, each cell type has a plurality of measurable dimensions. For example, mature human red blood cells (RBCs) in their natural state have a biconcave disc shape, with an average diameter of around 6-8 µm and average disc thickness of around 2 µm. The maximum natural dimension of the RBCs refers to the average diameter of the disc; the minimum natural dimension of the RBCs refers to the average disc thickness of the disc.

In the embodiments of the present invention, the maximum and/or minimum natural dimension of the cell components in the sample is less than 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 µm, 1.1 µm, 1.2 µm, 1.3 µm, 1.4 µm, 1.5 µm, 1.6 µm, 1.7 µm, 1.8 µm, 1.9 µm, 2 µm, 2.1 µm, 2.2 µm, 2.3 µm, 2.4 µm, 2.5 µm, 2.6 µm, 2.7 µm, 2.8 µm, 2.9 µm, 3 µm, 4 µm, 5 µm, 6 µm, 7 µm, 8 µm, 9 µm, 10 µm, 11 µm, 12 µm, 13 µm, 14 µm, 15 µm, 20 µm, 25 µm, 30 µm, 35 µm, 40 µm, 45 µm, 50 µm, 55 µm, 60 µm, 65 µm, 70 µm, 75 µm, 90 µm, 95 µm, 100 µm, 110 µm, 120 µm, 130 µm, 140 µm, 150 µm, 160 µm, 170 µm, 180 µm, 190 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, or 1 mm, or in a range between any of the two values. The maximum and/or minimum natural dimensions of the cell components affect the specific gap size at which a specific cell component can be lysed. In the embodiment shown in FIG. 13, panel (B), the second component 60 has the largest maximum and minimum natural dimension compared to the first component 50 and the third component 70; the third component 70 has the smallest maximum and minimum natural dimension compared to the first component 50 and the second component 60. The specific spacing 102, which is determined by the uniform height of the spacers 40 and is the same as the thickness of the layer of sample 90, can be specifically designed to lyse certain cell components based on the natural dimensions of the cells, as well as other factors that affect the lysing results. In some embodiments, to lyse a specific cell type, the gap size, or the thickness of the uniform layer, is significantly smaller than the minimum natural dimension of the cells. Herein, the term "significantly smaller" refers to less than 90%, 80%, 70%, 60%, 50%, 40%, 30% or 20% of the minimum natural dimension, or in a range between any two of the values.

The natural dimensions of each cell type are factors in determining whether the cell type is susceptible to lysing by mechanical forces. Other factors such as but not limited to cell flexibility, cell membrane permeability, sample salt concentrations also plays a role. For example, as shown in panel (C) of FIG. 13, although the second component 60 has a larger maximum and minimum dimensions compared to the first component, under the same conditions the first component 50 is lysed but the second component 60 is not lysed. In addition, features unrelated to the cells, such as but not limited to gap size, plate roughness, inter-spacer distance, and spacer density also affects how likely the cells are lysed. All other things equal, when the cells are trapped in a gap between two plates, whether the cells would be lysed depends on the gap size.

In some embodiments, the selectiveness of the lysing for specific cell type(s) depends on the gap size and the uniformity of the gap size; the more uniform the gap size, the more consistent is the lysing results. Herein, the cell components that are selected to be lysed are referred to as "target lysing component;" the cell components that are selected to be un-lysed are referred to as "non-target lysing component." A uniform and consistent lysing result refers to: a substantial fraction of the target lysing component is lysed in the gap, while a substantial fraction of the non-target lysing component un-lysed. In some embodiments, the gap size (or the thickness of the sample layer) is regulated by the spacers 40. Therefore, in certain embodiments, the height of the spacers 40 is selected such that in the closed configuration, a substantial fraction of the target-lysing component of the sample in the layer of uniform thickness is lysed, and a substantial fraction of the non-target lysing component in the layer of uniform thickness is not lysed. Herein, the term "substantial fraction" refers to a percentage equal to or more than 50%, 51%, 55%, 60%, 65%, 70%, 75%, 80%, 85%, 90%, 95%, 99% or 100%, or in a range between any of the two percentage values.

Panel (D) of FIG. 13 illustrates the device with a different spacer height compared to panel (C) after the compressing has been completed and certain cell types have been lysed. As shown in panel (D), the device is in a closed configuration. In the closed configuration, the spacing 102 between the two plates 10 and 20 are regulated by the spacers 40; in some embodiments, the spacing 102 is uniform and is substantially the same as the uniform height of the spacers 40. In addition, the layer of uniform thickness is also substantially the same as the spacing 102.

As shown in panel (D) of FIG. 13, since the layer of uniform thickness is smaller than the thickness in panel (C), the second component 60, which is un-lysed in the embodiment of panel (C), is lysed in the embodiment of panel (D) and has become lysed debris 61. The first component 50 is also lysed and has become lysed debris 51. The cells of the first component 50 and the second component 60 no longer maintain a complete cell membrane with observable cell contours. With the lysing of the first component 50 and the second component 60, the intracellular organelles and molecules in these cells are disbursed in the sample 90 and exposed. In certain embodiments, the intracellular organelles and molecules of the first component 50 and the second component 60 become available for assaying. In some embodiments, as shown in panel (D) of FIG. 13, the third component 70 is un-lysed. In certain embodiments, with the lysing of the first component 50 and the second component 60, it is advantageous to perform assays related to cell surface molecules of the third component 70; it is also advantageous to perform assays related to un-lysed-cell properties (e.g. cell number or expression of membrane bound molecules) of the third component 70.

In some embodiments, the target-lysing component is red blood cell, the non-target-lysing component is platelet, and the spacer height is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values.

In some embodiments, the target-lysing component is red blood cell, the non-target-lysing component is white blood cell, and the spacer height is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values.

In some embodiments, the target-lysing component is white blood cell, the non-target-lysing component is platelet, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

In some embodiments, the target-lysing component is red blood cell, the non-target-lysing component includes white blood cell and platelets, and the spacer height is equal to or less than 2 um, 1.9 um, 1.8 um, 1.7 um, 1.6 um, 1.5 um, 1.4 um, 1.3 um, 1.2 um, 1.1 um, or 1.0 urn, or in a range between any of the two values.

In some embodiments, the target-lysing component includes red blood cell and white blood cell, the non-target-lysing component is platelet, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

In some embodiments, on one or both the sample contact areas, the respective plate further comprises a layer of a reagent. In certain embodiments, the reagent facilitates: (a) the lysing of the targeted lysing component, and/or (b) the unlysing of non-targeted lysing components.

FIG. 14 shows other exemplary embodiments of the present invention, where spacers at different locations have different heights. It should be noted that certain descriptions regarding the embodiments shown in FIGS. 12 and 13 also apply to the embodiments of FIG. 14 as long as these descriptions do not contradict the specific discussion about the embodiments of FIG. 14. For example, while panel (A) of FIG. 14 shows that spacers 41 and 42 are attached to the first plate inner surface 11 of the first plate 10, it is clear from the descriptions regarding the embodiments in FIGS. 12-13 that such spacers are fixed to the second plate 20, or to both the first plate 10 and second plate 20.

Panel (A) of FIG. 14 illustrates a device that comprises a first plate 10 and a second plate 20, wherein the first plate 10 has a first plate inner surface 11 and first plate outer surface 12, the second plate 20 has a second plate inner surface 21 and second plate outer surface 22. As shown in panel (A) of FIG. 14, there are two sets of spacers: the first set of spacers 41 have a first uniform height 411; the second set of spacers 42 have a second uniform height 421; the first set and the second set of spacers 41 and 42 are positioned at different locations on the first plate 10. In some embodiments, the first set of spacer 41 are located in a first sample contact area and the second set of spacers 42 are located in a second sample receiving area. In certain embodiments, the first uniform height 411 is substantially different from the second uniform height 421. Herein, the term "substantially different" refers to a difference of at least 5%, 10%, 15%, 20%, 25%, 30%, 35%, 40%, 45%, 50%, 55%, 60%, 65%, 70%, 75%, 80%, 85%, 90% or 95%, or a difference in a range between any of the two values.

Panel (B) of FIG. 14 show the device of the present invention after a sample 90 has been added; the plates 10 and 20 are being compressed by force F, but before the plates have been fully switched to a closed configuration; the sample 90 is spreading and flowing on the plates, but the spacing between the plates 10 and 20 and the thickness of the sample 90 are not regulated by the height of the spacers 40. As shown in panel (B) of FIG. 14, the device of the present invention comprises a first plate 10 and a second plate 20, wherein the first plate 10 comprises a first plate inner surface 11 and a first plate outer surface 12, and the second plate 20 comprises a second plate inner surface 21 and a second plate outer surface 22. In some embodiments, in the open configuration (e.g. as shown in panel (B) of FIG. 12), a liquid sample 90 is added to one of the plates or both of the plates. Further referring to panel (C) of FIG. 12 and panel (B) of FIG. 14, the two plates 10 and 20 are compressed so that the sample 90 is confined by the first plate 10 and second plate 20.

As shown in panel (B) of FIG. 14, the sample 90 comprises multiple components. For illustrative purposes, the sample 90 shown in panel (B) of FIG. 14 comprises at least a first component 50, a second component 60, and a third component 70. In some embodiments, the first component 50, the second component 60, and the third component 70 are cells and each component represents a different cell type. Besides the cell components, the sample 90 also comprises a liquid component. In certain embodiments, the second component 60 has the largest maximum and minimum natural dimension compared to the first component 50 and the third component 70; the third component 70 has the smallest maximum and minimum natural dimension compared to the first component 50 and the second component 60.

The spacer heights 411 and 421 are designed to selective lyse specific cell types on different locations of the plates. In some embodiments, each of the spacers heights 411 and 421 is less than or equal to about 3 nm, 10 nm, 50 nm, 100 nm, 200 nm, 500 nm, 800 nm, 1000 nm, 1.2 µm, 1.4 µm, 1.5 µm, 1.6 µm, 1.8 µm, 2 µm, 3 µm, 5 µm, 10 µm, 20 µm, 30 µm, 50 µm, 100 µm, 150 µm, 200 µm, 300 µm, 500 µm, 800 µm, 1 mm, 2 mm, 4 mm, or in a range between any two of the values. In certain embodiments, each of the spacer heights 411 and 421 is around 0.2 µm, 0.5 µm, 0.8 µm, 1 µm, 1.2 µm, 1.5 µm, 1.8 µm, 2 µm, 2.5 µm, 3 µm or 3.5 µm. In some specific embodiments, the first spacer height 411 is equal to or more than about 1.5 µm and the second spacer height 421 is equal to or less than about 0.5 µm. In some specific embodiments, the first spacer height 411 is equal to or more than about 2 µm and the second spacer height 421 is equal to or less than about 1 µm. In some specific embodiments, the first spacer height 411 is equal to or more than about 0.5 µm and the second spacer height 421 is equal to or less than about 0.2 µm.

Panel (C) of FIG. 14 illustrates the device of the present invention after the compressing has been completed and certain cell types have been lysed in specific locations. As shown in panel (C), the device is in a closed configuration. In the closed configuration, the sample 90 is compressed by the two plates 10 and 20 into a layer that has at least two thicknesses at two different locations. The first thickness 1021, which is substantially the same as the spacer height 411 (see panel (A) of FIG. 14) is regulated by the first set of spacers 41; the second thickness 1022, which is substantially the same as the spacer height 421 (see panel (A) of FIG. 14, is regulated by the second set of spacers 42. The first thickness 1021 is highly uniform and the second thickness 1022 is also highly uniform; in some embodiments, these two thicknesses are substantially different from each other.

As shown in panel (C) of FIG. 14, the layer of sample 90 is a continuous layer. However, in some embodiments, the layer is not continuous and the sample is separated into different areas on the plates. As shown in panel (C) of FIG. 14, the first plate 10 is flexible and it is bent at section 15 to accommodate different spacers heights 1021 and 1022 in different locations of the first plate 10 and second plate 20. It should be noted that in a QMAC device, either or both of the plates are flexible.

As shown in panel (C) of FIG. 14, in some embodiments, the first component 50, the second component 60, and the third component 70 are all un-lysed in the first thickness 1021, which is regulated by the first set of spacers 41; at another location of the QMAX device, while the second component 60 and the third component 70 are un-lysed, the first component 50 is lysed in the second thickness 1022, which is regulated by the second set of spacers 42. In the second thickness 1022, the cells of the first component 50 have become lysed debris 51 and no longer maintain a complete cell membrane with observable cell contours. With such lysing, the intracellular organelles and molecules in the cells of the first component 50 are disbursed in the sample 90 and exposed. In certain embodiments, the intracellular organelles and molecules of the first component become available for assaying.

In some embodiments, the selectiveness of the lysing for specific cell type(s) depends on the gap size and the uniformity of the gap size; the more uniform the gap size, the more consistent is the lysing results. Herein, the cell components that are selected to be lysed at a specific location are referred to as "target lysing component;" the cell components that are selected to be un-lysed at the specific location are referred to as "non-target lysing component." In some embodiments, the gap size (or the thickness of the sample layer) is regulated by the spacers 40. Therefore, in certain embodiments, the height of the spacers is configured such that in the closed configuration, (a) the spacers have a substantially same spacer height in in the first sample contact area and a different substantially same spacer height in in the second sample contact area, and (b) in the first sample contact area: a substantial fraction of the target-lysing component of the sample in a layer of uniform thickness is lysed, and a substantial fraction of the non-target lysing component in a layer of uniform thickness is not lysed, while in the second sample contact area: neither the target nor the non-target lysing component is lysed. Herein, the term "substantial fraction" refers to a percentage equal to or more than 30%, 35%, 40%, 45%, 50%, 55%, 60%, 65%, 70%, 75%, 80%, 85%, 90%, 95%, 99% or 100%, or in a range between any of the two percentage values.

The QMAX device as shown in FIG. 14 allows selectively lysing of specific cell types on different locations of the plates 10 and 20. Specific assays are designed to measure specific organelles/molecules/properties at different locations of the plates 10 and 20, allowing for a comprehensive and efficient analysis of the sample using the same device. For example, in some embodiments and as show in panel (C) of FIG. 14, in the first thickness 1021 all three components are un-lysed, allowing an analysis of properties related to all the cells (e.g. total cell number) or to specific cell types (e.g. staining of properties of a cell surface molecule on the cells of the first component 50). In some embodiments as shown in panel (C) of FIG. 14, the first component is lysed by the second component 60 and the third component 70 are un-lysed in the second thickness 1022; it would be possible to analyze, for example, the intracellular organelles and molecules of the cells of the first component, while also monitoring the cell numbers of the second component 60 and third component 70. In addition, the lysing of the first component 50 also facilitates measuring the properties of the second component 60 and/or the third component 70.

Panel (D) of FIG. 14 shows the QMAX device with different spacer heights compared to panel (C), after the compressing has been completed, and different cell types have been lysed in different locations. As shown in panel (D) of FIG. 14, in some embodiments, while the second component 60 and the third component 70 are un-lysed, the first component 50 is lysed in the first thickness 1021, which is regulated by the first set of spacers 41; at another location of the QMAX device, the first component 50 and the second component 60 are lysed, but the third component 70 is un-lysed in the second thickness 1022, which is regulated by the second set of spacers 42. At the locations where the cell components 50 and/or 60 are lysed, these cells have become lysed debris 51 and/or 61 and no longer maintain a complete cell membrane with observable cell contours. With such lysing, the intracellular organelles and molecules in the cells of the lysed component are disbursed in the sample 90 and exposed. In certain embodiments, the intracellular organelles and molecules of the first component become available for assaying at a specific location of the QMAX device. In addition, in certain embodiment, the lysing of some components facilitates the measure of properties (e.g. cell number or expression of membrane bound molecule s) related to the un-lysed cells.

It should be noted that in some embodiments, the QMAX device comprises more than two sets of spaces fixed to more than two locations, while each set of spacers or each group of more than one set of spacers have different heights. For example, the QMAX device has three groups of spacers, each group including three sets having the sample height. Each set of spacers are positioned at different locations on the plates. The QMAC device is then used to selectively lyse different components in sample. Therefore, in certain embodiments, each group of spacers has different components lysed and/or un-lysed in the closed configuration. At the location of each set of spacers, the same or different assays are performed.

Properties of the QMAX Device

The descriptions of this section relate to the plates and the spacers of the QMAX device. The elements of these descriptions can also be combined with the features as shown in FIGS. 12-14 and described thereof.

Open Configuration.

In some embodiments, in the open configuration, the two plates (i.e. the first plate and the second plate) are separated from each other. In certain embodiments, the two plates have one edge connected together during all operations of the plates (including the open and closed configuration), the two plates open and close similar to a book. In some embodiments, the two plates have rectangle (or square) shape and have two sides of the rectangles connected together (e.g. with a hinge or similar connector) during all operations of the plates.

In some embodiments, the open configuration is a configuration that the plates are far away from each other, so that the sample is deposited onto one plate of the pair without any hindrance of the other plate. In some embodiments, when two sides of the plates are connected, the open configuration is a configuration that the plates form a wide angle (e.g. in the range of 60 to 180, 90 to 180, 120 to 180, or 150 to 180 degrees) so that the sample is deposited onto one plate of the pair without any hindrance of the other plate.

In some embodiments, the open configuration comprises a configuration that the plates are far way, so that the sample is directly deposited onto one plate, as if the other plate does not exist.

In some embodiments, the open configuration is a configuration that the pair of the plates are spaced apart by a distance at least 10 nm, at least 100 nm, at least 1000 nm, at least 0.01 cm, at least 0.1 cm, at least 0.5 cm, at least 1 cm, at least 2 cm, or at least 5 cm, or a range of any two of the values.

In some embodiments, the open configuration is a configuration that the pair of plates are oriented in different orientations. In some embodiments, the open configuration comprises a configuration that defines an access gap between the pair of plates that is configured to permit sample addition.

In some embodiments, the open configuration comprises a configuration, wherein each plate has a sample contact surface and wherein at least one of the contact surfaces of the plates is exposed when the plates are in the open configuration.

Closed Configuration and Sample Thickness Regulation.

In some embodiments, a closed configuration of the two plates is the configuration that a spacing (i.e. the distance) between the inner surfaces of the two plates is regulated by the spacers between the two plates. In some embodiments, the closed configuration is not related to whether the sample has been added to the plates. In some embodiments, the spacing between the inner surfaces of the two plates is substantially uniform and similar to the uniform height of the spacers.

Since the inner surfaces (also termed "sample surface") of the plates are in contact with the sample during the compression step of a CROF process after the sample has been added, in some embodiments at the closed configuration, the sample thickness is regulated by the spacers.

During the process of bringing the plates from an open configuration to a closed configuration, the plates are facing each other (at least a part of the plates are facing each other) and a force is used to bring the two plates together. If a sample has been deposited, when the two plates are brought from an open configuration to a closed configuration, the inner surfaces of the two plates compress the sample deposited on the plate(s) to reduce the sample thickness (while the sample has an open flow laterally between the plates), and the thickness of a relevant volume of the sample is determined by the spacers, the plates, and the method being used and by the sample mechanical/fluidic property. The thickness at a closed configuration can be predetermined for a given sample and given spacers, plates and plate pressing method.

The term "regulation of the spacing between the inner surfaces of the plates by the spacers" or "the regulation of the sample thickness by the plates and the spacer", or a thickness of the sample is regulated by the spacers and the plates" means that the spacing between the plates and/or the thickness of the sample in a CROF process is determined by given plates, spacers, sample, and pressing method.

In some embodiments, the regulated spacing between the inner surfaces and/or regulated sample thickness at the closed configuration is the same as the height of a spacer or the uniform height of the spacers; in this case, at the closed configuration, the spacers directly contact both plates (wherein one plate is the one that the spacer is fixed on, and the other plate is the plate that is brought to contact with the spacer).

In certain embodiments, the regulated spacing between the inner surfaces and/or regulated sample thickness at the closed configuration is larger than the height of a spacer; in this case, at the closed configuration, the spacers directly contacts only the plate that has the spacers fixed or attached on its surface, and indirectly contact the other plate (i.e. indirect contact). The term "indirect contact" with a plate means that the spacer and the plate is separated by a thin layer of air (when no sample has been deposited) or a thin sample layer (when a sample has been deposited), which is termed "residual layer" and its thickness is termed "the residue thickness". For given spacers and plates, a given plate pressing method, and a given sample, the residual thickness can be predetermined (predetermined means prior to reach the closed configuration), leading to a predetermination of the sample thickness at the closed configuration. This is because the residue layer thickness is the same for the given conditions (the sample, spacers, plates, and pressing force) and can be pre-calibrated and/or calculated. The regulated spacing or the regulated sample thickness is approximately equal to the spacer height plus the residue thickness.

In many embodiments, the spacers have a pillar shape and the size and shape of the pillars are pre-characterized (i.e. pre-determined) before their use. And the pre-determined parameters are used to for later assaying, such as determination of the sample volume (or relevant volume) and others.

In some embodiments, the regulating of the spacing between the inner surfaces and/or the sample thickness includes applying a closing (compression) force to the plates to maintain the spacing between the plates.

In some embodiments, the regulating of the spacing between the inner surfaces and/or the sample thickness includes establishing the spacing between the plates with the spacers, a closing force applied to the plates, and physical properties of the sample, and optionally wherein the physical properties of the sample include at least one of viscosity and compressibility.

In some embodiments, it would be possible to conformable press, either in parallel or sequentially, the QMAX device into a closed configuration. Conformable pressing is a method that makes the pressure applied over an area to be substantially constant regardless of the shape variation of the outer surfaces of the plates; In particular, parallel conformable pressing applies the pressures on the intended area at the same time, and sequential conformable pressing applies the pressure on a part of the intended area and gradually move to other area. Conformable pressing is applied by human hand, air blow, liquid pressure, or other forces.

Plates.

In the present invention, generally, the plates of CROF are made of any material that (i) is capable of being used to regulate, together with the spacers, part of all of the spacing between the plates and/or the thickness of a partial or entire volume of the sample, and (ii) has no significant adverse effects to a sample, an assay, or a goal that the plates intend to accomplish. However, in certain embodiments, particular materials (hence their properties) are used for the plate to achieve certain objectives.

In some embodiments, the two plates have the same or different parameters for each of the following parameters: plate material, plate thickness, plate shape, plate area, plate flexibility, plate surface property, and plate optical transparency.

Plate Materials.

In some embodiments, the plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1. The inorganic materials for any one of the plates include, but not limited to, glass, quartz, oxides, silicon-dioxide, silicon-nitride, hafnium oxide (HfO), aluminum oxide (A10), semiconductors: (silicon, GaAs, GaN, etc.), metals (e.g. gold, silver, cooper, aluminum, Ti, Ni, etc.), ceramics, or any combinations of thereof.

Mat-2 The organic materials for any one of the plates include, but not limited to, polymers (e.g. plastics) or amorphous organic materials. The polymer materials for the plates include, not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly (ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In some embodiments, the plates are each independently made of at least one of glass, plastic, ceramic, and metal. In some embodiments, each plate independently includes at least one of glass, plastic, ceramic, and metal.

In some embodiments, one plate is different from the other plate in lateral area, thickness, shape, materials, or surface treatment. In some embodiments, one plate is the same as the other plate in lateral area, thickness, shape, materials, or surface treatment.

The materials for the plates are rigid, flexible or any flexibility between the two. The rigidity (i.e. stiff) or flexibility is relative to a give pressing forces used in bringing the plates into the closed configuration.

In some embodiments, a selection of rigid or flexible plate is determined from the requirements of controlling a uniformity of the sample thickness at the closed configuration.

In some embodiments, at least one of the two plates are transparent (to a light). In some embodiments at least a part or several parts of one plate or both plates are transparent. In some embodiments, the plates are non-transparent.

Plate Thickness.

In some embodiments, the average thickness for at least one of the plates is 2 nm or less, 10 nm or less, 100 nm or less, 200 nm or less, 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, or in a range between any two of the values.

In some embodiments, the average thickness for at least one of the plates is at most 3 mm (millimeter), at most 5 mm, at most 10 mm, at most 20 mm, at most 50 mm, at most 100 mm, at most 500 mm, or in a range between any two of the values.

In some embodiments, the average thickness for at least one of the plates is in the range of 1 to 1000 µm, 10 to 900 µm, 20 to 800 µm, 25 to 700 µm, 25 to 800 µm, 25 to 600 µm, 25 to 500 µm, 25 to 400 µm, 25 to 300 µm, 25 to 200 µm, 30 to 200 µm, 35 to 200 µm, 40 to 200 µm, 45 to 200 µm, or 50 to 200 µm. In some embodiments, the average thickness for at least one of the plates is in the range of 50 to 75 µm, 75 to 100 µm, 100 to 125 µm, 125 to 150 µm, 150 to 175 µm, or 175 to 200 µm. In some embodiments, the average thickness for at least one of the plates is about 50 µm, about 75 µm, about 100 µm, about 125 µm, about 150 µm, about 175 µm, or about 200 µm.

In some embodiments, the thickness of a plate is not uniform across the plate. Using a different plate thickness at different location can be used to control the plate bending, folding, sample thickness regulation, and others.

Plate Shape and Area.

Generally, the plates can have any shapes, as long as the shape allows a compress open flow of the sample and the regulation of the sample thickness. However, in certain embodiments, a particular shape is advantageous. In certain embodiments, the shape of the plate is round, elliptical, rectangles, triangles, polygons, ring-shaped, or any superpositions of these shapes.

In some embodiments, the two plates can have the same size and/or shape, or different size and/or shape. The area of the plates depends on the specific application. In some embodiments, the area of the plate is at most 1 $mm^2$ (square millimeter), at most 10 $mm^2$, at most 100 $mm^2$, at most 1 $cm^2$ (centimeter square), at most 2 $cm^2$, at most 5 $cm^2$, at most 10 $cm^2$, at most 100 $cm^2$, at most 500 $cm^2$, at most 1000 $cm^2$, at most 5000 $cm^2$, at most 10,000 $cm^2$, or over 10,000 $cm^2$, or any range between any of the two values.

In certain embodiments, at least one of the plate is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or in a range between any two of the values. The length can be as long it needed. The belt can be rolled into a roll.

Plate Surface Flatness.

In many embodiments, an inner surface of the plates is flat or significantly flat, planar. In certain embodiments, the two inner surfaces of the plates are, at the closed configuration, parallel with each other. Flat inner surfaces facilitate a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

The flatness of the plate surface is relative to the final sample thickness (the final thickness is the thickness at the closed configuration), and is often characterized by the term of "relative surface flatness," which is the ratio of the plate surface flatness variation to the final sample thickness.

In some embodiments, the relative surface flatness is less than 0.01%, 0.1%, less than 0.5%, less than 1%, less than 2%, less than 5%, less than 10%, less than 20%, less than 30%, less than 50%, less than 70%, less than 80%, less than 100%, or in a range between any two of these values.

Plate Surface Parallelness.

In some embodiments, the two surfaces of the plate are significantly parallel with each other in the closed configuration. Here "significantly parallel" means that an angle formed but extensions of the two plates is less than 0.1, 0.2, 0.5, 1, 2, 3, 4, 5, 10, or 15 degrees. In certain embodiments, the two surfaces of the plate are not parallel with each other.

Plate Flexibility.

In some embodiments, a plate is flexible under the compressing of a CROF process. In some embodiments, both plates are flexible under the compressing of a CROF process. In some embodiments, a plate is rigid and another plate is flexible under the compressing of a CROF process. In some embodiments, both plates are rigid. In some embodiments, both plates are flexible but have different flexibility.

Plate Optical Transparency.

In some embodiments, a plate is optically transparent. In some embodiments, both plates are optically transparent. In some embodiments, a plate is optically transparent and another plate is opaque. In some embodiments, both plates are opaque. In some embodiments, both plates are optically transparent but have different transparency. The optical transparency of a plate refers to a part or the entire area of the plate.

Plate Surface Wetting Properties.

In some embodiments, a plate has an inner surface that wets (i.e. contact angle is less 90 degree) the sample, the transfer liquid, or both. In some embodiments, both plates have an inner surface that wets the sample, the transfer liquid, or both; either with the same or different wettability. In some embodiments, a plate has an inner surface that wets the sample, the transfer liquid, or both; and another plate has an inner surface that does not (i.e. the contact angle equal to or larger than 90 degree). The wetting of a plate inner surface refers to a part or the entire area of the plate.

In some embodiments, the inner surface of the plate has other nano or microstructures to control a lateral flow of a sample during a CROF process. The nano or microstructures include, but not limited to, channels, pumps, and others. Nano and microstructures are also used to control the wetting properties of an inner surface.

Spacers' Function.

In the present invention, the spacers are configured to have one or any combinations of the following functions and properties: the spacers are configured to (1) control, together with the plates, the spacing between the plates and/or the thickness of the sample for a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, and/or (7) do any combination of the above.

Spacer Architectures and Shapes.

To achieve desired sample thickness reduction and control, in certain embodiments, the spacers are fixed on its respective plate. In general, the spacers can have any shape, as long as the spacers are capable of regulating the spacing between the plates and the sample thickness during a CROF process, but certain shapes are preferred to achieve certain functions, such as better uniformity, less overshoot in pressing, etc.

The spacer(s) is a single spacer or a plurality of spacers. (e.g. an array). Some embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (i.e. the sample flows around and pass the spacer. For example, a post as the spacer.), and the enclosed spacer is the spacer that stop the sample flow (i.e. the sample cannot flow beyond the spacer. For example, a ring shape spacer and the sample is inside the ring.). Both types of spacers use their height to regulate the spacing between the plates and/or the final sample thickness at a closed configuration.

In some embodiments, the spacers are open-spacers only. In some embodiments, the spacers are enclosed-spacers only. In some embodiments, the spacers are a combination of open-spacers and enclosed-spacers.

The term "pillar spacer" means that the spacer has a pillar shape and the pillar shape refers to an object that has height and a lateral shape that allow a sample to flow around it during a compressed open flow.

In some embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In some embodiments, the spacers are and/or include posts, columns, beads, spheres, and/or other suitable geometries. The lateral shape and dimension (i.e., transverse to the respective plate surface) of the spacers can be anything, except, in some embodiments, the following restrictions: (i) the spacer geometry will not cause a significant error in measuring the sample thickness and volume; or (ii) the spacer geometry would not prevent the out-flowing of the sample between the plates (i.e. it is not in enclosed form). But in some embodiments, they require some spacers to be closed spacers to restrict the sample flow.

In some embodiments, the shapes of the spacers have rounded corners. For example, a rectangle shaped spacer has one, several or all corners rounded (like a circle rather than a 90-degree angle). A round corner often makes a fabrication of the spacer easier, and in some cases less damaging to a biological material.

The sidewall of the pillars can be straight, curved, sloped, or different shaped in different section of the sidewall. In some embodiments, the spacers are pillars of various lateral shapes, sidewalls, and pillar-height to pillar lateral area ratio.

In a preferred embodiment, the spacers have shapes of pillars for allowing open flow.

Spacers' Materials.

In the present invention, the spacers are generally made of any material that is capable of being used to regulate, together with the two plates, the thickness of a relevant volume of the sample. In some embodiments, the materials for the spacers are different from that for the plates. In some embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mixture thereof.

The inorganic materials for the spacers include, but are not limited to, glass, quartz, oxides, silicon-dioxide, silicon-nitride, hafnium oxide (HfO), aluminum oxide (A10), semiconductors: (silicon, GaAs, GaN, etc.), metals (e.g. gold, silver, cooper, aluminum, Ti, Ni, etc.), ceramics, or any combinations thereof.

The organic materials for the spacers include, but are not limited to, polymers (e.g. plastics) or amorphous organic materials. The polymer materials for the plates include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations thereof.

In one embodiment, the spacers are made in the same material as a plate used in the QMAX device.

Spacer's Mechanical Strength and Flexibility.

In some embodiments, the mechanical strength of the spacers is strong enough, so that during the compression and at the closed configuration of the plates, the height of the spacers is the same or significantly the same as that when the plates are in an open configuration. In some embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

Spacer Inside Sample.

To achieve desired sample thickness reduction and control, particularly to achieve a good sample thickness uniformity, in certain embodiments, the spacers are placed inside the sample, or the relevant volume of the sample. In some embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" is determined by a sample thickness uniformity or a required sample flow property during a CROF.

Spacer Height.

In some embodiments, all spacers have the same pre-determined height. In some embodiments, spacers have different pre-determined heights. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or in a range between any two of the values.

The spacer height, the spacing between the plates, and/or sample thickness is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment.

In some embodiments, the spacer height is controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

In some embodiments, the spacer height, the spacing between the plates, and/or sample thickness is: (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

For example, the red blood cell has a disk shape with a minim dimension of 2 µm (disk thickness) and a maximum dimension of 11 µm (a disk diameter). In an embodiment of the present invention, the spacers are selected to make the inner surface spacing of the plates in a relevant area to be 2 µm (equal to the minimum dimension) in one embodiment, 2.2 µm in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 µm and any number between the two values, an undiluted whole blood sample is confined in the spacing; on average, each red blood cell (RBC) does not overlap with others, allowing an accurate counting of the red blood cells visually. (Too many overlaps between the RBC's can cause serious errors in counting).

In some embodiments, the spacer height, the spacing between the plates, and/or sample thickness is: (i) equal to or smaller than the minimum dimension of an analyte, or (ii) equal to or slightly smaller than the maximum dimension of an analyte. The "slightly smaller" means that it is about 1% to 5% smaller and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

In the present invention, in some embodiments, the plates and the spacers are used to regulate not only the thickness of a sample, but also the orientation and/or surface density of the analytes/entity in the sample when the plates are at the closed configuration. When the plates are at a closed configuration, a thinner thickness of the sample results in less analytes/entity per surface area (i.e. less surface concentration).

Spacer Lateral Dimension.

For an open-spacer, the lateral dimensions can be characterized by its lateral dimension (sometimes called width) in the x and y—two orthogonal directions. The lateral dimension of a spacer in each direction is the same or different. In some embodiments, the lateral dimension for each direction (x or y) is 1 nm or less, 3 nm or less, 5 nm or less, 7 nm or less, 10 nm or less, 20 nm or less, 30 nm or less, 40 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, or 500 µm or less, or in a range between any two of the values.

In some embodiments, the ratio of the lateral dimensions of x to y direction is 1, 1.5, 2, 5, 10, 100, 500, 1000, 10,000, or a range between any two of the value. In some embodiments, a different ratio is used to regulate the sample flow direction; the larger the ratio, the flow is along one direction (larger size direction).

In some embodiments, different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height of the spacers are substantially the same. In some embodiments, all spacers have the same shape and dimensions. In some embodiments, the spacers have different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

In certain embodiments, the aspect ratio of the height to the average lateral dimension of the pillar spacer is 100,000, 10,000, 1,000, 100, 10, 1, 0.1, 0.01, 0.001, 0.0001, 0, 00001, or in a range between any two of the values.

Inter-Spacer Distance.

The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers is arranged as lattices of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

In some embodiments, the distance between neighboring spacers (i.e. the inter-spacer distance) is 1 µm or less, 5 µm or less, 7 µm or less, 10 µm or less, 20 µm or less, 30 µm or less, 40 µm or less, 50 µm or less, 60 µm or less, 70 µm or less, 80 µm or less, 90 µm or less, 100 µm or less, 200 µm or less, 300 µm or less, 400 µm or less, or in a range between any two of the values.

In certain embodiments, the inter-spacer distance is at 400 µm or less, 500 µm or less, 1 mm or less, 2 mm or less, 3 mm or less, 5 mm or less, 7 mm or less, 10 mm or less, or in any range between the values. In certain embodiments, the inter-spacer distance is a 10 mm or less, 20 mm or less, 30 mm or less, 50 mm or less, 70 mm or less, 100 mm or less, or in any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or in any range between the values; or in certain embodiments, at most 80%, 100%, 200%, 400%, or in a range between any two of the values.

Clearly, for maintaining a given sample thickness variation between two neighboring spacers, when a more flexible plate is used, a closer inter-spacer distance is needed.

In a preferred embodiment, the spacer is a periodic square array, wherein the spacer is a pillar that has a height of 2 to 4 µm, an average lateral dimension of from 1 to 20 µm, and inter-spacer spacing of 1 µm to 100 µm.

In a preferred embodiment, the spacer is a periodic square array, wherein the spacer is a pillar that has a height of 2 to 4 µm, an average lateral dimension of from 1 to 20 µm, and inter-spacer spacing of 100 µm to 250 µm.

In a preferred embodiment, the spacer is a periodic square array, wherein the spacer is a pillar that has a height of 4 to 50 µm, an average lateral dimension of from 1 to 20 µm, and inter-spacer spacing of 1 µm to 100 µm.

In a preferred embodiment, the spacer is a periodic square array, wherein the spacer is a pillar that has a height of 4 to 50 µm, an average lateral dimension of from 1 to 20 µm, and inter-spacer spacing of 100 µm to 250 µm.

The period of spacer array is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment, 100 µm to 175 µm in a separate preferred embodiment, and 175 µm to 300 µm in a separate preferred embodiment.

Spacer Density.

The spacers are arranged on the respective plates at a surface density of greater than one per $\mu m^2$, greater than one per 10 $\mu m^2$, greater than one per 100 $\mu m^2$, greater than one per 500 $\mu m^2$, greater than one per 1000 $\mu m^2$, greater than one per 5000 $\mu m^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or in a range between any two of the values. In some embodiments, the spacers have a density of at least $1/mm^2$, at least $10/mm^2$, at least $50/mm^2$, at least $100/mm^2$, at least $1,000/mm^2$, or at least $10,000/mm^2$.

Spacer area filling factor is defined as the ratio of spacer area to the total area or the ratio of spacer period to the width. In some embodiments, the filling factor is at least 1%, 2%, 3%, 4%, 5%, 6%, 7%, 8%, 9%, 10%, 20%, or in the range between any of the two values. In certain embodiments, the filling factor is at least 2.3%.

Ratio of Spacer Volume to Sample Volume.

In many embodiments, the ratio of the spacer volume (i.e. the volume of the spacer) to sample volume (i.e. the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (i.e. flow speed, flow direction, etc.).

In some embodiments, the spacers are configured to not take significant surface area (volume) in a given sample area (volume).

In certain embodiments, the ratio of the spacer volume r) to sample volume, and/or the ratio of the volume of the spacers that are inside of the relevant volume of the sample to the relevant volume of the sample is less than 100%, at most 99%, at most 90%, at most 70%, at most 50%, at most 30%, at most 10%, at most 5%, at most 3% at most 1%, at most 0.1%, at most 0.01%, at most 0.001%, or in a range between any of the values.

Spacers Fixed to Plates.

The inter spacer distance and the orientation of the spacers, which play a key role in the present invention, are preferably maintained during the process of bringing the plates from an open configuration to the closed configuration, and/or are preferably predetermined before the process from an open configuration to a closed configuration.

In some embodiments of the present invention, the spacers are fixed on one of the plates before bringing the plates to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (i.e. the spacer moves away from its original position on the plate surface).

In some embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In some embodiments, a spacer is fixed to a plate monolithically.

In some embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (i.e. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In some embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In some embodiments, at least a distance between two spacers is predetermined ("predetermined inter-spacer distance" means that the distance is known when a user uses the plates.).

In some embodiments of all methods and devices described herein, there are additional spacers besides to the fixed spacers.

Sample.

In the present invention of the methods and devices that use a CROF process, the sample is deposited by one of several methods or a combination of the methods. In one embodiment of the deposition, the sample is deposited on only one plate. In certain embodiments, the sample is deposited on both plates (i.e. the first and the second plate).

The sample is deposited when the plates are at an open configuration. In some embodiments, the deposition of the sample can be a single drop or multiple drops. The multiple drops can be at one location or multiple locations of either one plate or both plates. The droplets can be well separated from each other, connected, or a combination of thereof.

In some embodiments, a sample comprises more than one materials, and the materials are deposited together or separately. In certain embodiments, the materials are deposited separately either in parallel or sequence.

The deposition of the sample to the plates (i.e. the first plate and the second plate) can be performed using a device or directly from test subject to the plates. In some embodiments, a sample is deposited using a device. The device includes, but is not limited to, pipettes, needle, stick, swab, tube, jet, liquid dispenser, tips, stick, inkjets, printers, spraying devices, etc. In certain embodiments, a sample is deposited by a direct contacting between the sample at the sample source and a QMAX plate without using any devices (i.e. bring the sample and the plate together to make a contact between the two). This is termed "direct sample deposition".

Examples of a direct sample deposition of a sample to a plate(s) are (a) a direct contact of between pricked finger (or other body parts) and a plate, (b) spitting saliva onto the plate(s), (c) taking a tear in human eyes by a direct contact between the tear and the plate(s), (d) a direct contact between the sweat and the plate(s), and (e) a direct breathing onto the plate(s) to deposit a breath, etc. Such direct deposition method can be used for both human and animals.

In some embodiments, both a direct and indirect (through a device) sample deposition are used.

In present invention, the volume of the sample that is deposited on the plate or the plates ("sample volume") is at most 0.001 µL (pico liter), at most 0.01 µL, at most 0.1 µL, at most 1 µL, at most 10 µL, at most 100 µL, at most 1 nL (nano liter), at most 10 nL, at most 100 nL, at most 1 uL (micro liter), at most 10 uL, at most 100 uL, at most 1 mL (milliliter), at most 10 mL, or in a range of any two of these values.

In some embodiments, the depositing of a sample comprises the steps of (a) putting a sample on one or both of the plates, and (b) spreading the sample using a means other than the second plate compression in a CROF process. The means of spreading the sample include using another device (e.g. stick, blade), air blow, liquid pressure, or others.

Sample Deformation.

During a CROF process, in some embodiments, the samples behave approximately like an incompressible liquid (which refers to a liquid that maintains a constant volume under a shape deformation), therefore a change in the sample thickness would lead to the change in the sample area. In some embodiments, the samples behave like a compressible liquid, yet their lateral area still expand when their thickness is reduced during a CROF process. In certain embodiments, the sample are liquid, gel, or soft-solids, as long as that, during a CROF process, their lateral area expands when their thickness is reduced.

In the of the present invention disclosed, "facing the first plate and the second plate" is a process that manipulates the position and orientation of the first plate or the second plate or both, so that the sample is between the inner surfaces of the first plate and the second plate. In some embodiments, the action of "facing the first plate and the second plate" is performed by human hands, human hands with certain devices, or automatic devices without human hands.

In some embodiments, the thickness is at most 1 mm, at most 100 µm, at most 20 µm, at most 10 µm, or at most 2 µm. In some embodiments, the thickness is at least 0.1 µm. In some embodiments, further comprising measuring the thickness.

In some embodiments, a variation of the thickness of the relevant volume of the sample is at most 300%, at most 100%, at most 30%, at most 10%, at most 3%, at most 1%, at most 0.3%, or at most 0.1% of an effective diameter of the relevant area In some embodiments, the thickness is at least partially determined by the predetermined height.

Final Sample Thickness.

The final sample thickness at the closed configuration of the plates is a significant factor in reducing the saturation incubation time. The final sample thickness after the sample thickness reduction/deformation, depending upon the properties of entity and samples as well as the applications, as discussed with respect to the regulated spacing of the plates.

In some embodiments, The final sample thickness is less than about 0.5 µm (micrometer), less than about 1 µm, less than about 1.5 µm, less than about 2 µm, less than about 4 µm, less than about 6 µm, less than about 8 µm, less than about 10 µm, less than about 12 µm, less than about 14 µm, less than about 16 µm, less than about 18 µm, less than about 20 µm, less than about 25 µm, less than about 30 µm, less than about 35 µm, less than about 40 µm, less than about 45 µm, less than about 50 µm, less than about 55 µm, less than about 60 µm, less than about 70 µm, less than about 80 µm, less than about 90 µm, less than about 100 µm, less than about 110 µm, less than about 120 µm, less than about 140 µm, less than about 160 µm, less than about 180 µm, less than about 200 µm, less than about 250 µm, less than about 300 µm, less than about 350 µm, less than about 400 µm, less than about 450 µm, less than about 500 µm, less than about 550 µm, less than about 600 µm, less than about 650 µm, less than about 700 µm, less than about 800 µm, less than about 900 µm, less than about 1000 µm (1 mm), less than about 1.5 mm, less than about 2 mm, less than about 2.5 mm, less than about 3 mm, less than about 3.5 mm, less than about 4 mm, less than about 5 mm, less than about 6 mm, less than about 7 mm, less than about 8 mm, less than about 9 mm, less than about 10 mm, or in a range between any two of the values.

In certain embodiments, the final sample thickness at the closed configuration is substantially the same as the uniform height of the spacers and is less than 0.5 µm (micron), less than 1 µm, less than 5 µm, less than 10 µm, less than 20 µm, less than 30 µm, less than 50 µm, less than 100 µm, less than 200 µm, less than 300 µm, less than 500 µm, less than 800 µm, less than 200 µm, less than 1 mm (millimeter), less than 2 mm (millimeter), less than 4 mm (millimeter), less than 8 mm (millimeter), or in a range between any two of the values.

In the present invention, it was observed that a larger plate holding force (i.e. the force that holds the two plates together) can be achieved by using a smaller plate spacing (for a given sample area), or a larger sample area (for a given plate-spacing), or both.

In some embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

Final Sample Thickness and Uniformity.

In some embodiments, the sample in the closed configuration is significantly flat, which is determined relative to the final sample thickness, and has, depending upon on embodiments and applications, a ratio to the sample thickness of less than 0.1%, less than 0.5%, less than 1%, less than 2%, less than 5%, or less than 10%, or in a range between any two of these values.

In some embodiments, flatness relative to the sample thickness is less than 0.1%, less than 0.5%, less than 1%, less than 2%, less than 5%, less than 10%, less than 20%, less than 50%, or less than 100%, or a range between any two of these values.

In some embodiments, significantly flat means that the surface flatness variation itself (measured from an average thickness) is less than 0.1%, less than 0.5%, less than 1%, less than 2%, less than 5%, or less than 10%, or a range between any two of these values. Generally, flatness relative to the plate thickness is less than 0.1%, less than 0.5%, less than 1%, less than 2%, less than 5%, less than 10%, less than 20%, less than 50%, or less than 100%, or a range between any two of these values.

Selective Lysing Examples and Results

This section provides certain embodiment of the selective lysing devices and methods. These embodiments only demonstrate, but do not in any way limit, the present invention. As used herein, the term "X-plate" refers to a flexible plate to which the spacers are fixed; the term "substrate" refers to a plate that does not include fixed spacers. In some embodiments, the X-plate is viewed as the first plate 10 as shown in FIGS. 13-14 and the substrate is viewed as the second plate 20 as shown in FIGS. 13-14.

Figure 15:
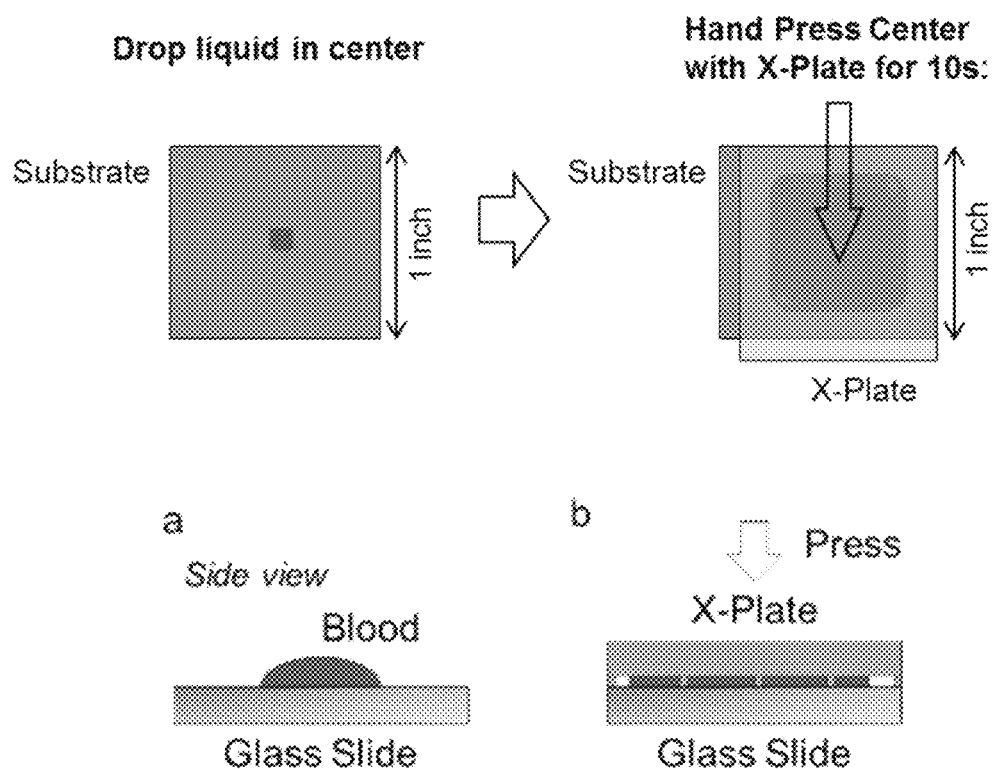
FIG. 15 illustrates a top view and cross-section view of (i) dropping a small volume sample on a glass substrate, (ii) the sample area expanded at the closed configuration of CROF.

FIG. 15 illustrates a top view and cross-section view of (i) dropping a small volume sample on a glass substrate, (ii) the sample area expanded at the closed configuration of the QMAX device. As illustrate in FIG. 15, first, a small volume (a few µl or less) of sample was deposited on either the substrate or the X-plate, which forms form a small paddle(s). Second the plates were brought together with overlaps of the sample surface of the plate. Third, hand is used to press the plates into a closed configuration, where the sample become a thin film with an area much larger than the original paddle. Fourth, the hand(s) was related. And fifth, various measurements were performed at the closed configuration.

In particular, blood (either fresh blood without anti-coagulant reagents or store blood with anti-coagulant reagents) were dropped at a volume of 0.8 uL (for 2 µm spacing X-device), 0.4 uL (for 1 µm spacing X-device), 0.2 uL (for 500 nm and 200 nm spacing X-device) on center of a glass substrate; b) the center of X-Plate (1" by 1") on top of the blood was pressed by hand for 10 s.

In some experiments, fresh blood was first stained in Acridine orange dye for 1 min in a tube. (1:1 ratio, AO dye is 100 ug/mL in PBS). After the stained blood was dropped onto the glass substrate, an X-Plate was pressed onto the blood by hand. Acridine orange (AO) is a stable dye that has a natural affinity for nucleic acids. When binding to DNA, AO intercalates with DNA as a monomer and yields intense green fluorescence under blue excitation. (470 nm excitation, 525 nm green emission for WBC). When binding to RNA and proteins it forms an electrostatic complex in a polymeric form that yields red fluorescence under blue excitation. (470 nm excitation, 685 nm red emission for WBC, PLTs). RBCs do not have nucleic acids, thus were not stained. WBCs have nuclei with both DNA and RNA, thus were strongly stained. Platelets (PLTs) have low amount of RNA, thus only weakly stained.

The samples in the QMAX devices were observed by commercial DSLR camera (Nikon®) with two filters, one light source and a magnification/focus lens set. In bright field mode, a broadband white light Xe lamp source without any filters was used. In fluorescence mode, the excitation source was a Xenon lamp with a 470±20 nm excitation filter (Thorlabs®), and the emission filter is a 500 nm long pass filter (Thorlabs®). The results are summarized in Table 1.

TABLE 1

Setup of QMAX device on blood cell lyse test

| | | X-Plate parameters | | | | | Liquid Volume | Liquid diameter before press | Liquid diameter after press |
|---|---|---|---|---|---|---|---|---|---|
| | Substrate | Material | Thickness | Pillar Size width | Pillar Distance | Pillar height | | | |
| 1 | Glass 1 mm thick | PMMA | 175 um | 30 × 40 um | 80 um | 2 µm | 0.8 uL | 2 mm | 2.3 cm |
| 2 | | PMMA | 175 um | 30 × 40 um | 80 um | 1 µm | 0.4 uL | 1.5 mm | 2.3 cm |
| 3 | | Fused Silica | 500 um | 85 × 85 nm | 115 nm | 500 nm | 0.2 uL | 1.3 mm | 2.3 cm |
| 4 | | Fused Silica | 500 um | 85 × 85 nm | 115 nm | 200 nm | 0.2 uL | 1.3 mm | 3.6 cm |

Figure 16:
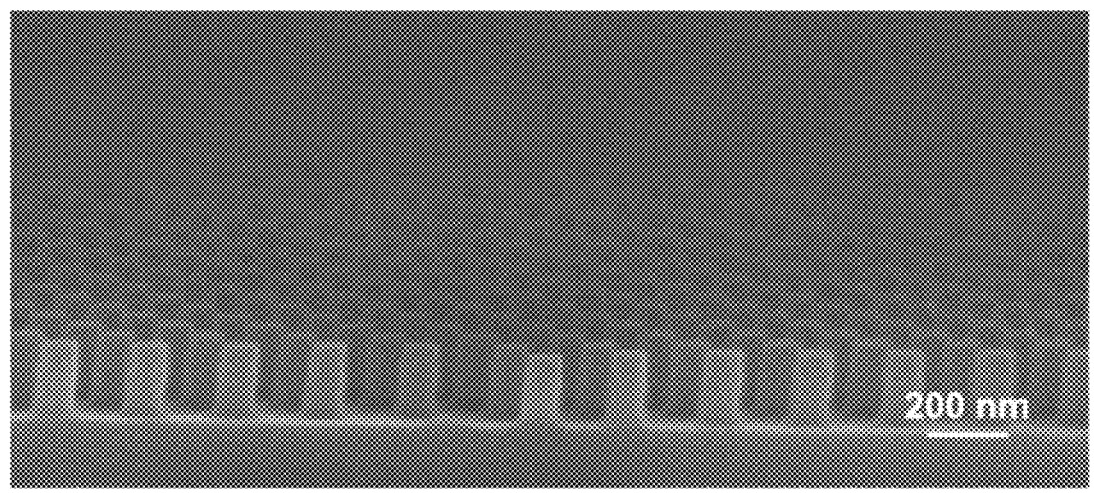
FIG. 16 shows a scanning electron micrograph (SEM) photo of a nano-array X-plate.

For sample 3 and 4, the test utilized fabricated X-Plate with pillar array of 85 nm pillar diameter, 200 nm periods, 500 nm and 200 nm pillar height using fused silica material. FIG. 16 shows a scanning electron micrograph (SEM) photo of a nano-array X-plate with 85 nm pillar diameter, 200 nm period, and 200 nm pillar height.

Figure 17:
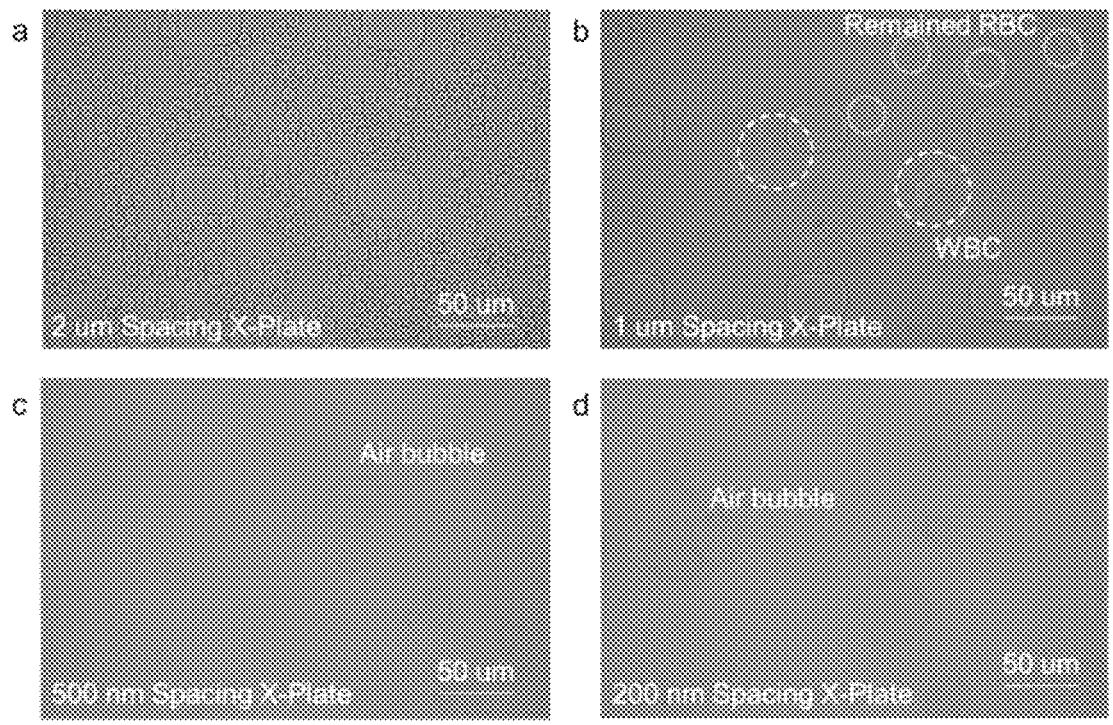
FIG. 17 shows bright field photos of blood cells in 2 um, 1 um, 500 nm and 200 nm spacing size QMAX devices.

FIG. 17 shows bright field photos of blood cells in 2 um, 1 um, 500 nm and 200 nm spacing size QMAX devices. In FIG. 17, bright figures photos show: a) with 2 um spacing size X-Plate, RBCs and WBCs in blood are not lysed and arranged in a single layer. b) With 1 um spacing size X-Plate, most (99%) of the RBCs are lysed, but WBCs are not lysed. c,d) With 500 nm and 200 nm spacing size X-Plates, both RBCs and WBCs are lysed. Only air bubble can be observed in bright field observation mode.

Figure 18:
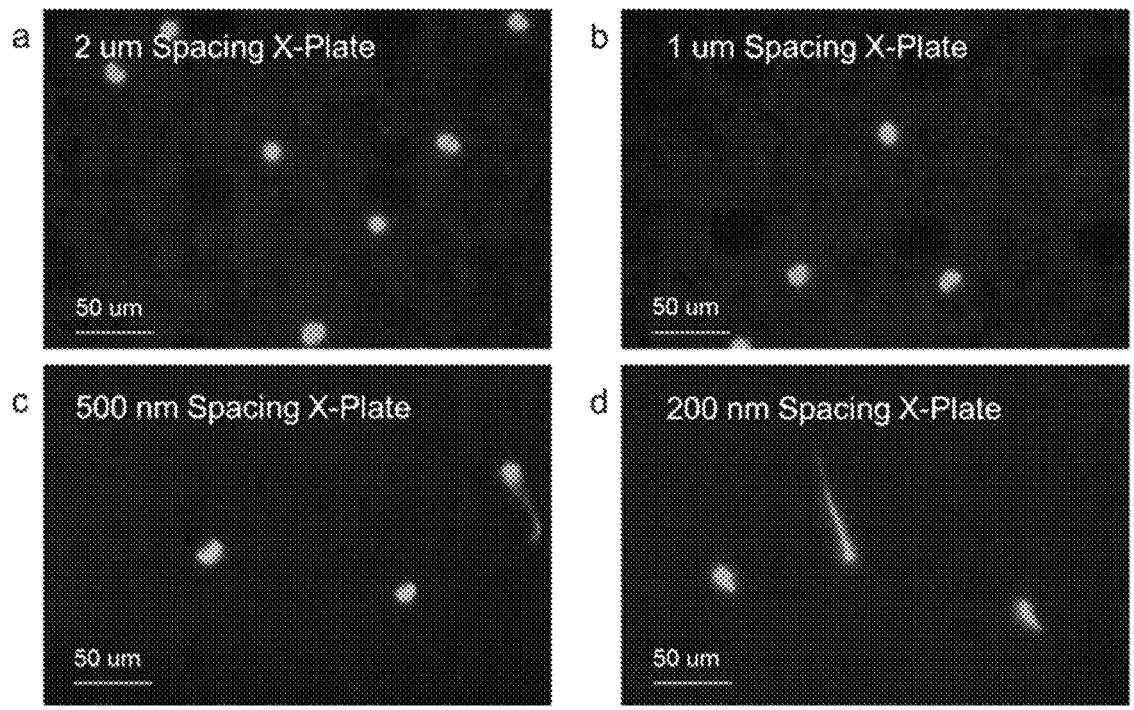
FIG. 18 shows fluorescence photos of blood cells in 2 um, 1 um, 500 nm and 200 nm spacing size QMAX devices.

FIG. 18 shows fluorescence photos of blood cells in 2 um, 1 um, 500 nm and 200 nm spacing size QMAX devices. As shown in FIG. 18, in fluorescence mode, only WBCs or DNA/RNA strands in WBC can be observed. a,b) With 2 um and 1 um spacing size X-Plate, WBCs in blood are not lysed and can be clearly observed with round shape. c,d) With 500 nm and 200 nm spacing size X-Plates, WBCs are lysed. The DNAs/RNAs strands (green lines from the cell) are extracted from the cells.

Figure 19:
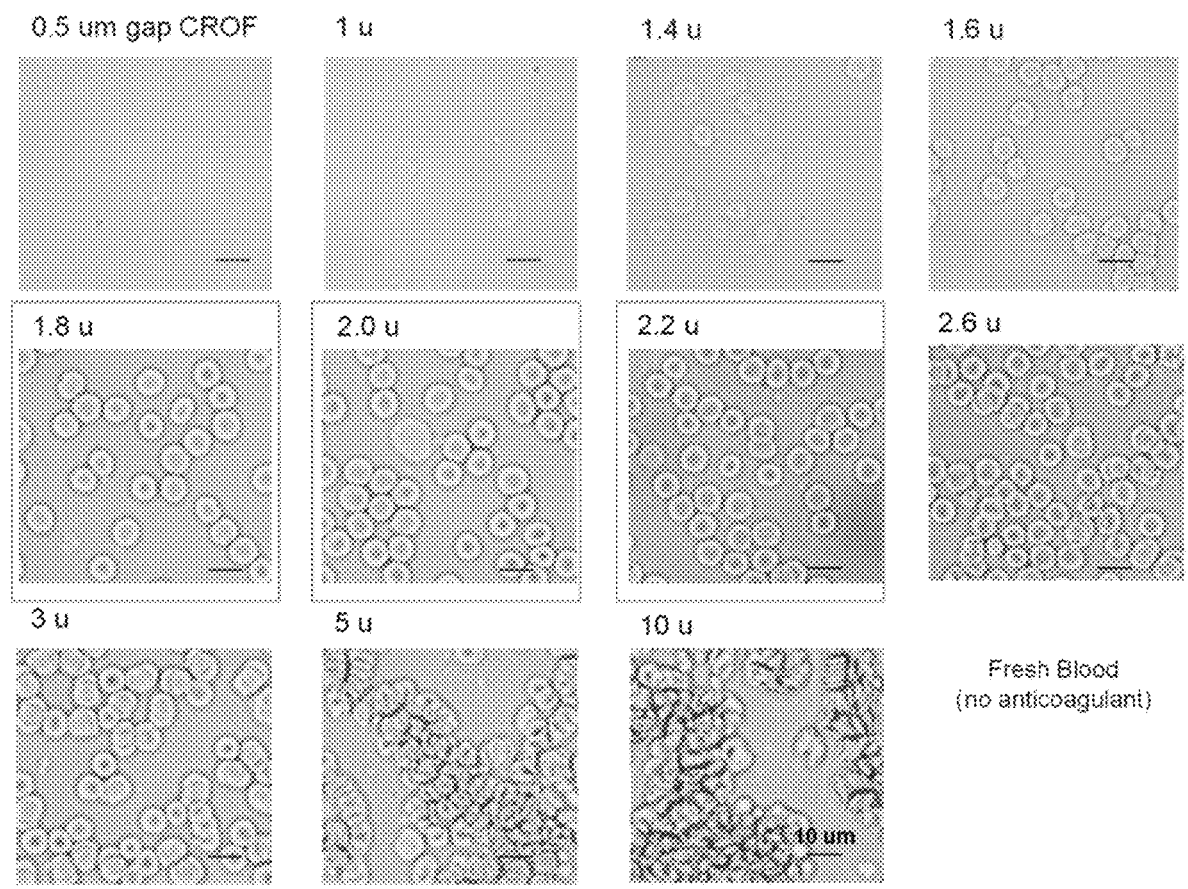
FIG. 19 shows bright field photos of fresh undiluted whole blood without anti-coagulant in QMAX devices with different pillar heights.

FIG. 19 shows bright field photos of fresh undiluted whole blood without anti-coagulant in QMAX devices with different pillar heights. The blood was added to the QMAX devices in the open configuration directly from a pricked finger. The X-Plate had a micro pillar array on this surface made of PMMA; the microarray has pillar size of 30 µm×40 um, with 80 µm inter-spacer distance (ISD) with heights between 0.5 µm to 10 µm. The other plate is made of glass.

The results for selective lysing at different spacer heights were summarized in Table 2.

TABLE 2

Lysing performance summary with different QMAX setup

| | QMAX card | | | | |
|---|---|---|---|---|---|
| | Substrate | X-Plate pillar | Lysing Performance | | |
| No. | type | height | RBCs | WBCs | PLTs |
| 1 | Flat Substrate (with surface roughness less than 100 nm)[3] | 0.2 µm (nano-array)[1] | Lyse >99% | Lyse | Lyse |
| 2 | | 0.5 µm (nano-array) *1 | Lyse >99% | Lyse | Lyse |

TABLE 2-continued

Lysing performance summary with different QMAX setup

| | QMAX card | | | | |
|---|---|---|---|---|---|
| | Substrate | X-Plate pillar | Lysing Performance | | |
| No. | type | height | RBCs | WBCs | PLTs |
| 3 | | 0.5 µm *2 | Lyse 95% | No Lyse | No Lyse |
| 4 | | 1.0 µm *2 | Lyse 80% | No Lyse | No Lyse |
| 5 | | 2.0 µm *2 | No Lyse | No Lyse | No Lyse |
| 6 | | 3.0 µm *2 | No Lyse | No Lyse | No Lyse |
| 7 | Rough Substrate (with surface roughness 2 um) | 0.5 µm *2 | Lyse 80% | No Lyse | No Lyse |
| 8 | | 1.0 µm *2 | Lyse 30% | No Lyse | No Lyse |

In Table 2, *1: Nano-array X-Plate: 85 nm pillar size (circle, diameter), 115 nm ISD, 200 nm pitch, on 500 um thick fused silica material; *2: X-Plate: 30×40 µm pillar size (rectangle), 80 µm ISD, on 175 um thick PMMA (Acrylics) material; and *3: Flat or Rough Substrate are 1 mm thick polystyrene (PS) material.

For the confinement gap of 0.5 µm, almost all the RBCs were lysed, while WBC and PLT remained. For the confinement gap of 1 µm, most (80%) of the RBCs were lysed, WBCs and PLTs remained un-lysed. For the confinement gap between 1 um to 1.8 µm, some of the RBCs were lysed, some remained. The thicker the gap, the more RBCs remained and WBCs and PLTs were un-lysed. For the confinement gap of 2 µm, each RBC was separated from others, had no observable overlap, and had a well-defined boundary surrounded each cell and a shadowed center (due to a thinner center thickness). Furthermore, the WBCs and platelets were also separated from other cells. For the 2.2 µm gap, some RBCs started to overlap with another RBCs, but there were no observable platelets overlap. For the 2.6 µm and 3 µm gap, there were more RBCs overlap, triple RBCs overlap started and the platelets overlapped with RBCs, and the overlapping increased with the gap. For the 5 µm and 10 µm gaps, massive numbers of cells overlap (e.g. coagulated), rouleaux of RBCs are visible, and many RBCs cells had a narrow elliptical shape, which is due to the rotation of the RBCs relative to the imaging plane.

FIG. 9 of U.S. Provisional Patent Application No. 62/456, 528, which is incorporated herein by reference in its entirety, shows bright field photos of stored undiluted whole blood with anti-coagulant in QMAX devices with different pillar heights. The X-Plate had a micro pillar array on this surface made of PMMA; the microarray has lateral pillar size of 30 μm×40 um, with 80 μm inter-spacer distance (ISD) with heights between 0.5 μm to 10 μm. The other plate is made of glass.

Overall the results were similar to the results with fresh blood, except: (1) For the confinement gap between 0.5 μm to 1.8 μm, RBCs seemed to be more fragile, indicating that with the same gap size, more RBCs were lysed; (2) For the confinement gap between 2 μm to 10 μm, with the anticoagulant, although the RBCs did not coagulate together, they could rotate and overlap for forming a large gap.

FIG. 10 of U.S. Provisional Patent Application No. 62/456,528, which is incorporated herein by reference in its entirety, shows bright field and phase contrast photos (at 20× magnification) of fresh blood sample in a QMAX device with 0.5 μm pillar height. In the QMAX device, the pillars had a lateral size of 10 μm×20 um, with 80 μm inter-spacing distance (ISD) with heights of 0.5 μm. The other plate is made of glass. For the confinement gap of 0.5 μm, almost all (95%-99%) the RBCs were lysed, and the WBCs and PLTs remained. WBCs were pressed into a size larger than typical free standing.

FIG. 11 of U.S. Provisional Patent Application No. 62/456,528, which is incorporated herein by reference in its entirety, shows a bright field photo (at 4× magnification) of fresh blood sample in a QMAX device with 0.5 μm pillar height. For the confinement gap of 0.5 μm, almost all (95%-99%) the RBCs were lysed, and the WBCs and PLTs remained. WBCs were pressed into a size larger than typical free standing.

FIG. 12 of U.S. Provisional Patent Application No. 62/456,528, which is incorporated herein by reference in its entirety, shows bright field and phase contrast photos (at 20× magnification) of fresh blood sample in a QMAX device with 1.0 μm pillar height. The X-Plate had a micro pillar array on this surface made of PMMA; the pillars had a lateral pillar size of 30 μm×40 um, with 80 μm inter-spacer distance (ISD) with height of 1.0 μm. The other plate is made of glass. For the confinement gap of 1.0 μm, most (80-95%) of the RBCs were lysed, remaining 5-20% RBCs, WBCs and PLTs were un-lysed.

FIG. 13 of U.S. Provisional Patent Application No. 62/456,528, which is incorporated herein by reference in its entirety, shows bright field photos of fresh blood samples in QMAX devices with 1.0 and 0.5 μm pillar heights on flat plastic substrate. FIG. 14 of U.S. Provisional Patent Application No. 62/456,528, which is incorporated herein by reference in its entirety, shows bright field photos of fresh blood samples in QMAX devices with 2.0, 1.0 and 0.5 μm pillar heights on rough plastic substrate.

FIG. 15 of U.S. Provisional Patent Application No. 62/456,528, which is incorporated herein by reference in its entirety, shows bright field photos for platelet (PLT) and white blood cell (WBC) counting on QMAX devices with 0.5 μm gap. In the QMAX device herein used, the X-Plate had a micro pillar array on this surface made of PMMA. The pillars had a lateral size of 10 μm×20 um, with 80 μm inter-spacing distance (ISD) with height of 0.5 um. The other plate was made of glass. Freshly finger-pricked blood was immediately and directly deposited from the finger to the QMAX device for testing.

The counting was performed in 9 areas (3×3 array with a period of 8 mm, thus effective area of 16 mm×16 mm) on the QMAX device. Each area has a counting field of view of 1650 μm×1100 μm for WBC count, and 330 μm×220 μm for PLT count. For comparison, commercial manual hemocytometer was used to count the same fresh blood. First, an EDTA coated tube was used to collect more than 10 uL fresh blood. Then 5 uL of the blood was diluted 100× in RBC lysing buffer to lyse the RBCs. 10 uL of the lysed blood was loaded in commercial manual hemocytometer (Sigma-Aldrich, Z359629) and manual counted PLT and WBC. The results are shown in Table 3.

TABLE 3

PLT, WBC counting with 0.5 μm gap vs. manual counting

|  | CROF (0.5 um) | Manual |
|---|---|---|
| PLT count ($10^3$/uL) | 324 | 300 |
| WBC count ($10^3$/uL) | 5.9* | 6.5 |

From above results, PLT and WBC count result with 0.5 um QMAX card is similar (within 10% difference) to that in manual counting. (a) PLTs were not lysed in 0.5 um QMAX card, and were countable; (b) most of the WBCs were not lysed in 0.5 um QMAX card, and were countable. In summary, 0.5 um QMAX card can be used to count PLTs and WBCs.

A summary of the selective lysing results is provided in Table 4.

TABLE 4

Selective lysing for blood sample.

| Lysed | Unlysed | Plate gap range (μm) |
|---|---|---|
| RBC | Platelet | 0.2-2 |
| RBC | WBC | 1-2 |
| WBC | Platelet | 0.2-1 |
| RBC | WBC + Platelets | 1-2 |
| RBC + WBC | Platelet | 0.2-1 |

As shown in Table 4, when the target-lysing component is RBC and the non-target lysing component is platelet, the plate gap (spacer height) is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values.

As shown in Table 4, when the target-lysing component is RBC and the non-target-lysing component is WBC, the plate gap (spacer height) is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values.

As shown in Table 4, when the target-lysing component is white blood cell and the non-target-lysing component is platelet, the plate gap (spacer height) is equal to or less than 1.0 um, 0.9 um, 0.8 um, 0.7 um, 0.6 um, 0.5 um, 0.4 um, 0.3 um, or 0.2 um, or in a range between any of the two values.

As shown in Table 4, when the target-lysing component is RBC and the non-target-lysing component includes WBC and platelets, the plate gap (spacer height) is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values.

As shown in Table 4, when the target-lysing component includes RBC and WBC and the non-target-lysing component is platelet, the plate gap (spacer height) is equal to or less than 1.0 um, 0.9 um, 0.8 um, 0.7 um, 0.6 um, 0.5 um, 0.4 um, 0.3 um, or 0.2 um, or in a range between any of the two values.

In some embodiments, the QMAX device (termed QMAX card when the two plates are connected, e.g. by a hinge) of the present invention includes, but not limited to, the embodiments described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016; all of these disclosures are hereby incorporated by reference for their entireties and for all purposes.

The devices and methods herein disclosed have various types of biological/chemical sampling, sensing, assays and applications, which include, but not limited to, those described in PCT Application (designating U.S.) No. PCT/US2016/045437, which was filed on Aug. 10, 2016, and PCT/US16/51794, which was filed on Sep. 14, 2016, are hereby incorporated by reference by its entirety.

The devices and methods herein disclosed is used for samples such as but not limited to diagnostic sample, clinical sample, environmental sample and foodstuff sample. The types of sample include but are not limited to the samples listed, described and summarized in PCT Application (designating U.S.) No. PCT/US2016/045437, which was filed on Aug. 10, 2016, and is hereby incorporated by reference by its entirety.

The devices and methods herein disclosed are used for the detection, purification and/or quantification of analytes such as but not limited to biomarkers. Examples of the biomarks include but not be limited to what is listed, described and summarized in PCT Application (designating U.S.) No. PCT/US2016/045437, which was filed on Aug. 10, 2016, and is hereby incorporated by reference by its entirety.

The devices and methods herein disclosed are used with the facilitation and enhancement of mobile communication devices and systems, which include devices and systems listed, described and summarized in PCT Application (designating U.S.) No. PCT/US2016/045437, which was filed on Aug. 10, 2016, and is hereby incorporated by reference by its entirety.

First Group of Other Examples of Present Invention

Further examples of inventive subject matter according to the present disclosure are described in the following enumerated paragraphs.

A0. A device for lysing a component in a liquid sample, comprising:
a first plate, a second plate, and spacers, wherein
i. the plates are movable relative to each other into different configurations, including an open configuration and a closed configuration;
ii. each of the plates has, on its respective sample surface, a sample contact area for contacting a sample, wherein the sample comprises at least a target lysing component;
iii. one or both of the plates comprise the spacers, and the spacers are fixed to the respective plates;
iv. the spacers have a spacing between two neighboring spacers that is two times of the size of the target lysing component or larger, and
wherein in the open configuration, the two plates are partially or entirely separated apart, the spacing between the plates is not regulated by the spacers, and the sample is deposited on one or both of the plates;
wherein in the closed configuration, which is configured after deposition of the sample in the open configuration: at least a part of the sample is compressed by the two plates into a layer of highly uniform thickness, and the uniform thickness is confined by the sample contact surfaces of the plates and is regulated by the plates and the spacers; and
wherein the spacers have a predetermined height configured to lyse, in the closed configuration, a substantial fraction of the target-lysing component of the sample in the layer of highly uniform thickness.

A1. A device for selectively lysing a component in a liquid sample, comprising:
a first plate, a second plate, and spacers, wherein
i. the plates are movable relative to each other into different configurations, including an open configuration and a closed configuration;
ii. each of the plates has, on its respective sample surface, a sample contact area for contacting a sample, wherein the sample comprises at least a target lysing component and at least a non-target lysing component,
iii. one or both of the plates comprise the spacers, and the spacers are fixed to the respective sample contact area, and
iv. the height of the spacers is selected such that in the closed configuration, a substantial fraction of the target-lysing component of the sample in a relevant volume of the sample is lysed, and a substantial fraction of the non-target lysing component in the relevant volume of the sample is not lysed;
wherein in an open configuration, the two plates are partially or entirely separated apart, the spacing between the plates is not regulated by the spacers, and the sample is deposited on one or both of the plates;
wherein in the closed configuration, which is configured after deposition of the sample in the open configuration: the relevant volume of the sample is compressed by the two plates into a layer of highly uniform thickness, and the uniform thickness of the layer is confined by the sample contact surfaces of the plates and is regulated by the plates and the spacers; and
wherein the relevant volume of the sample is a partial or entire volume of the sample.

A2. The device of any prior embodiments, wherein the substantial fraction is at least 51%, 60%, 70%, 80%, 90%, 95% or 99% of a component in the relevant volume of the sample.

A3. The device of any prior embodiments, wherein the thickness variation of the layer of highly uniform thickness over the lateral area of the relevant volume is equal to or less than 40%, 30%, 20%, 15%, 10%, 7%, 5%, 3%, or 1%, or in a range between any of the two values, wherein the thickness variation is relative to the average thickness of the lateral area.

A4. The device of any prior embodiments, wherein the area of the highly uniform layer is equal to or larger than 0.1 mm$^2$, 0.5 mm$^2$, 1 mm$^2$, 3 mm$^2$, 5 mm$^2$, 10

$mm^2$, 20 $mm^2$, 50 $mm^2$, 70 $mm^2$, 100 $mm^2$, 200 $mm^2$, 500 $mm^2$, 800 $mm^2$, 1000 $mm^2$, 2000 $mm^2$, 5000 $mm^2$, 10000 $mm^2$, 20000 $mm^2$, 50000 $mm^2$, or 100000 $mm^2$; or in a range between any of the two values.

A5. The device of any prior embodiments, wherein the liquid sample is whole blood.

A6. The device of any prior embodiments, wherein the target-lysing component is red blood cell, and the spacer height is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values.

A7. The device of any prior embodiments, wherein the target-lysing component is white blood cell, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

A8. The device of any prior embodiments, wherein the target-lysing component is red blood cell, the non-target-lysing component is platelet, and the spacer height is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values.

A9. The device of any prior embodiments, wherein the target-lysing component is red blood cell, the non-target-lysing component is white blood cell, and the spacer height is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values.

A10. The device of any prior embodiments, wherein the target-lysing component is white blood cell, the non-target-lysing component is platelet, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

A11. The device of any prior embodiments, wherein the target-lysing component is red blood cell, the non-target-lysing component includes white blood cell and platelets, and the spacer height is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values.

A12. The device of any prior embodiments, wherein the target-lysing component includes red blood cell and white blood cell, the non-target-lysing component is platelet, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

A13. The device of any prior embodiments, wherein on one or both the sample contact areas, the respective plate further comprises a layer of a reagent.

A14. The device of embodiment A13, wherein the reagent facilitates: (a) the lysing of the targeted lysing component, and/or (b) the unlysing of non-targeted lysing components.

B0. A method for lysing a component in a liquid sample, comprising:
(a) obtaining a sample, which comprises at least a target lysing component;
(b) obtaining a first and second plates that are movable relative to each other into different configurations, including an open configuration and a closed configuration, wherein:
  i. each plate, on its respective surface, has a sample contact area,
  ii. one or both of the plates comprise spacers that are fixed with a respective sample contact surface,
    wherein the spacers have a predetermined substantially uniform height, and at least one of the spacers is inside the sample contact area;
(c) depositing the sample on one or both of the plates when the plates are in an open configuration,
  wherein in the open configuration the two plates are partially or entirely separated apart and the spacing between the plates is not regulated by the spacers; and
(d), after (c), bringing the two plates together and pressing the plates into a closed configuration,
  wherein in the closed configuration: a relevant volume of the sample is compressed by the two plates into a layer of highly uniform thickness, the uniform thickness of the layer is confined by the sample surfaces of the two plates and is regulated by the spacers and the plates,
  wherein the height of the spacers is selected such that in the closed configuration, a substantial fraction of the target-lysing component of the sample in the relevant volume of the sample is lysed; and
  the relevant volume of the sample is a partial or entire volume of the sample.

B1. A method for selectively lysing a component in a liquid sample, comprising:
(a) obtaining a sample, which comprises at least a non-target lysing component and at least a target lysing component;
(b) obtaining a first and second plates that are movable relative to each other into different configurations, including an open configuration and a closed configuration, wherein:
  i. each plate, on its respective surface, has a sample contact area,
  ii. one or both of the plates comprise spacers that are fixed with a respective sample contact surface,
    wherein the spacers have a predetermined substantially uniform height, and at least one of the spacers is inside the sample contact area;
(c) depositing the sample on one or both of the plates when the plates are in an open configuration,
  wherein in the open configuration the two plates are partially or entirely separated apart and the spacing between the plates is not regulated by the spacers; and
(d), after (c), bringing the two plates together and pressing the plates into a closed configuration,
  wherein in the closed configuration: a relevant volume of the sample is compressed by the two plates into a layer of highly uniform thickness, the uniform thickness of the layer is confined by the sample surfaces of the two plates and is regulated by the spacers and the plates,
  wherein the height of the spacers is selected such that in the closed configuration, a substantial fraction of the target-lysing component of the sample in the relevant volume of the sample is lysed, and a substantial fraction of the non-target lysing component in the relevant volume of the sample is not lysed; and the relevant volume of the sample is a partial or entire volume of the sample.

B2. The method of any prior B embodiments, wherein the substantial fraction is at least 51%, 60%, 70%, 80%, 90%, 95% or 99% of a component in the relevant volume of the sample.

B3. The method of any prior B embodiments, wherein the thickness variation of the layer of highly uniform thickness over the lateral area of the relevant volume is equal to or less than 40%, 30%, 20%, 15%, 10%, 7%, 5%, 3%, or 1%, or in a range between any of the two values, wherein the thickness variation is relative to the average thickness of the lateral area.

B4. The method of any prior B embodiments, wherein the area of the highly uniform layer is equal to or larger than 0.1 mm$^2$, 0.5 mm$^2$, 1 mm$^2$, 3 mm$^2$, 5 mm$^2$, 10 mm$^2$, 20 mm$^2$, 50 mm$^2$, 70 mm$^2$, 100 mm$^2$, 200 mm$^2$, 500 mm$^2$, 800 mm$^2$, 1000 mm$^2$, 2000 mm$^2$, 5000 mm$^2$, 10000 mm$^2$, 20000 mm$^2$, 50000 mm$^2$, or 100000 mm$^2$; or in a range between any of the two values.

B5. The method of any prior B embodiments, wherein the liquid sample is whole blood.

B6. The method of any prior B embodiments, wherein the target-lysing component is red blood cell, and the spacer height is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values.

B7. The method of any prior B embodiments, wherein the target-lysing component is white blood cell, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

B8. The method of any prior B embodiments, wherein the target-lysing component is red blood cell, the non-target-lysing component is platelet, and the spacer height is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values.

B9. The method of any prior B embodiments, wherein the target-lysing component is red blood cell, the non-target-lysing component is white blood cell, and the spacer height is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values.

B10. The method of any prior B embodiments, wherein the target-lysing component is white blood cell, the non-target-lysing component is platelet, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

B11. The method of any prior B embodiments, wherein the target-lysing component is red blood cell, the non-target-lysing component includes white blood cell and platelets, and the spacer height is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values.

B12. The method of any prior B embodiments, wherein the target-lysing component includes red blood cell and white blood cell, the non-target-lysing component is platelet, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

B13. The method of any prior B embodiments, wherein on one or both the sample contact areas, the respective plate further comprises a layer of a reagent.

B14. The method of embodiment B13, wherein the reagent facilitates: (a) the lysing of the targeted lysing component, and/or (b) the unlysing of non-targeted lysing components.

C0. A device for lysing a component in a liquid sample, comprising:

a first plate, a second plate, and spacers, wherein i. the plates are movable relative to each other into different configurations, including an open configuration and a closed configuration;

ii. the first plate has, on its respective sample surface, a first sample contact area at one location and a second sample contact area at another location, wherein the sample contact areas are for contacting a sample, wherein the sample comprises at least a target lysing component, iii. one or both of the plates comprise the spacers, and the spacers are fixed to the respective plate, and iv. the height of the spacers is configured such that in the closed configuration, (a) the spacers have a substantially same spacer height in in the first sample contact area and a different substantially same spacer height in in the second sample contact area, and (b) in the first sample contact area: a substantial fraction of the target-lysing component of the sample in a first relevant volume of the sample is lysed, while in the second sample contact area: the target lysing component is not lysed in a second relevant volume of the sample;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: the first relevant volume of the sample is compressed by the two plates, is on the first sample contact area and has a first highly uniform thickness, and the first relevant volume of the sample is compressed by the two plates, is on the first sample contact area and has a first highly uniform thickness, wherein the first and second uniform thicknesses are confined by sample surfaces of the two plates and are regulated by the spacers, and wherein the first and second relevant volumes of the sample are parts of the sample.

C1. A device for selectively lysing a component in a liquid sample, comprising:

a first plate, a second plate, and spacers, wherein i. the plates are movable relative to each other into different configurations, including an open configuration and a closed configuration;

ii. the first plate has, on its respective sample surface, a first sample contact area at one location and a second sample contact area at another location, wherein the sample contact areas are for contacting a sample, wherein the sample comprises at least a target lysing component and at least a non-target lysing component, iii. one or both of the plates comprise the spacers, and the spacers are fixed to the respective plate, and iv. the height of the spacers is configured such that in the closed configuration, (a) the spacers have a substantially same spacer height in in the first sample contact area and a different substantially same spacer height in in the second sample contact area, and (b) in the first sample contact area: a substantial fraction of the target-lysing component of the sample in a first relevant volume of the sample is lysed, and a substantial fraction of the non-target lysing component in the first relevant volume of the sample is not lysed, while in the second sample contact area: neither the target nor the non-target lysing component is lysed in a second relevant volume of the sample;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: the first relevant volume of the sample is compressed by the two plates, is on the first sample contact area and has a first highly uniform thickness, and the first relevant volume of the sample is compressed by the two plates, is on the first sample contact area and has a first highly uniform thickness, wherein the first and second uniform thicknesses are confined by sample surfaces of the two plates and are regulated by the spacers, and wherein the first and second relevant volumes of the sample are parts of the sample.

C2. The device of any prior C embodiments, wherein the substantial fraction is at least 51%, 60%, 70%, 80%, 90%, 95% or 99% of a component in the first relevant volume of the sample.

C3. The device of any prior C embodiments, wherein the thickness variation of the first layer of highly uniform thickness over the lateral area of the first relevant volume is equal to or less than 40%, 30%, 20%, 15%, 10%, 7%, 5%, 3%, or 1%, or in a range between any of the two values, wherein the thickness variation is relative to the average thickness of the lateral area.

C4. The device of any prior C embodiments, wherein the area of the first sample contact area or the second sample contact area is equal to or larger than 0.1 mm$^2$, 0.5 mm$^2$, 1 mm$^2$, 3 mm$^2$, 5 mm$^2$, 10 mm$^2$, 20 mm$^2$, 50 mm$^2$, 70 mm$^2$, 100 mm$^2$, 200 mm$^2$, 500 mm$^2$, 800 mm$^2$, 1000 mm$^2$, 2000 mm$^2$, 5000 mm$^2$, 10000 mm$^2$, 20000 mm$^2$, 50000 mm$^2$, or 100000 mm$^2$; or in a range between any of the two values.

C5. The device of any prior C embodiments, wherein the liquid sample is whole blood.

C6. The device of any prior embodiments, wherein the target-lysing component is red blood cell, and the spacer height is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values.

C7. The device of any prior C embodiments, wherein the target-lysing component is white blood cell, and the spacer height is equal to or less than 1.0 um, 0.9 um, 0.8 um, 0.7 um, 0.6 um, 0.5 um, 0.4 um, 0.3 um, or 0.2 um, or in a range between any of the two values.

C8. The device of any prior C embodiments, wherein the target-lysing component is red blood cell, the non-target-lysing component is platelet, and the spacer height in the first sample contact area is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values, and the spacer height in the second sample contact area is more than 2 um.

C9. The device of any prior C embodiments, wherein the target-lysing component is red blood cell, the non-target-lysing component is white blood cell, and the spacer height in the first sample contact area is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values, and the spacer height in the second sample contact area is more than 2 um.

C10. The device of any prior C embodiments, wherein the target-lysing component is white blood cell, the non-target-lysing component is platelet, and the spacer height in the first sample contact area is equal to or less than 1.0 um, 0.9 um, 0.8 um, 0.7 um, 0.6 um, 0.5 um, 0.4 um, 0.3 um, or 0.2 um, or in a range between any of the two values, and the spacer height in the second sample contact area is more than 1 um.

C11. The device of any prior C embodiments, wherein the target-lysing component is red blood cell, the non-target-lysing component includes white blood cell and platelets, and the spacer height in the first sample contact area is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values, and the spacer height in the second sample contact area is more than 2 um.

C12. The device of any prior C embodiments, wherein the target-lysing component includes red blood cell and white blood cell, the non-target-lysing component is platelet, and the spacer height in the first sample contact area is equal to or less than 1.0 um, 0.9 um, 0.8 um, 0.7 um, 0.6 um, 0.5 um, 0.4 um, 0.3 um, or 0.2 um, or in a range between any of the two values, and the spacer height in the second sample contact area is more than 1 um.

C13. The device of any prior C embodiments, wherein on one or both the sample contact areas, the respective plate further comprises a layer of a reagent.

C14. The device of embodiment C13, wherein the reagent facilitates: (a) the lysing of the targeted lysing component, and/or (b) the unlysing of non-targeted lysing components.

D0. A method of lysing a component in sample, comprising:
(a) obtaining a sample, which comprises at least a target lysing component;
(b) obtaining a first and second plates that are movable relative to each other into different configurations, wherein:
   i. the first plate has, on its respective sample surface, a first sample contact area at one location and a second sample contact area at another location,
   ii. one or both of the plates comprise spacers, and the spacers are fixed to the respective plate;
(c) depositing the sample on one or both of the plates when the plates are in an open configuration, wherein in the open configuration the two plates are partially or entirely separated apart; and (d), after (c), bringing the two plates together and pressing the plates into a closed configuration, wherein in the closed configuration: at least part of the sample is compressed by the two plates into a layer that has a first uniform thickness at the first sample contact area and a second uniform thickness at the second sample contact area, wherein the first uniform thickness is regulated by a first set of spacers and the second uniform thickness is regulated by a second set of spacers, wherein the first uniform thickness is different from the second uniform thickness; and wherein the height of the spacers is configured such that in the closed configuration:

i. the spacers has a substantially same spacer height in in the first sample contact area and a different substantially same spacer height in in the second sample contact area, and ii. in the first sample contact area: a substantial fraction of the target-lysing component of the sample in the layer of uniform thickness is lysed, while in the second sample contact area: the target lysing component is not lysed.

D1. A method of selectively lysing a component in sample, comprising:

(a) obtaining a sample, which comprises at least a non-target lysing component and at least a target lysing component;

(b) obtaining a first and second plates that are movable relative to each other into different configurations, wherein:

i. the first plate has, on its respective sample surface, a first sample contact area at one location and a second sample contact area at another location, ii. one or both of the plates comprise spacers, and the spacers are fixed to the respective plate;

(c) depositing the sample on one or both of the plates when the plates are in an open configuration, wherein in the open configuration the two plates are partially or entirely separated apart; and (d), after (c), bringing the two plates together and pressing the plates into a closed configuration, wherein in the closed configuration: at least part of the sample is compressed by the two plates into a layer that has a first uniform thickness at the first sample contact area and a second uniform thickness at the second sample contact area, wherein the first uniform thickness is regulated by a first set of spacers and the second uniform thickness is regulated by a second set of spacers, wherein the first uniform thickness is different from the second uniform thickness; and wherein the height of the spacers is configured such that in the closed configuration, i. the spacers has a substantially same spacer height in in the first sample contact area and a different substantially same spacer height in in the second sample contact area, and ii. in the first sample contact area: a substantial fraction of the target-lysing component of the sample in the layer of uniform thickness is lysed, and a substantial fraction of the non-target lysing component in the layer of uniform thickness is not lysed, while in the second sample contact area: neither the target nor the non-target lysing component is lysed.

D2. The method of any prior D embodiments, wherein the substantial fraction is at least 51%, 60%, 70%, 80%, 90%, 95% or 99% of a component in the first relevant volume of the sample.

D3. The method of any prior D embodiments, wherein the thickness variation of the first layer of highly uniform thickness over the lateral area of the first relevant volume is equal to or less than 40%, 30%, 20%, 15%, 10%, 7%, 5%, 3%, or 1%, or in a range between any of the two values, wherein the thickness variation is relative to the average thickness of the lateral area.

D4. The method of any prior D embodiments, wherein the area of the first sample contact area or the second sample contact area is equal to or larger than 0.1 mm$^2$, 0.5 mm$^2$, 1 mm$^2$, 3 mm$^2$, 5 mm$^2$, 10 mm$^2$, 20 mm$^2$, 50 mm$^2$, 70 mm$^2$, 100 mm$^2$, 200 mm$^2$, 500 mm$^2$, 800 mm$^2$, 1000 mm$^2$, 2000 mm$^2$, 5000 mm$^2$, 10000 mm$^2$, 20000 mm$^2$, 50000 mm$^2$, or 100000 mm$^2$; or in a range between any of the two values.

D5. The method of any prior D embodiments, wherein the liquid sample is whole blood.

D7. The method of any prior D embodiments, wherein the target-lysing component is red blood cell, and the spacer height in the first sample contact area is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values, and the spacer height in the second sample contact area is more than 2 um.

D7. The method of any prior D embodiments, wherein the target-lysing component is white blood cell, and the spacer height in the first sample contact area is equal to or less than 1.0 um, 0.9 um, 0.8 um, 0.7 um, 0.6 um, 0.5 um, 0.4 um, 0.3 um, or 0.2 um, or in a range between any of the two values, and the spacer height in the second sample contact area is more than 1 um.

D8. The method of any prior D embodiments, wherein the target-lysing component is red blood cell, the non-target-lysing component is platelet, and the spacer height in the first sample contact area is equal to or less than 2 um, 1.9 um, 1.8 um, 1.7 um, 1.6 um, 1.5 um, 1.4 um, 1.3 um, 1.2 um, 1.1 um, 1.0 um, 0.9 um, 0.8 um, 0.7 um, 0.6 um, 0.5 um, 0.4 um, 0.3 um, or 0.2 um, or in a range between any of the two values, and the spacer height in the second sample contact area is more than 2 um.

D9. The method of any prior D embodiments, wherein the target-lysing component is red blood cell, the non-target-lysing component is white blood cell, and the spacer height in the first sample contact area is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values, and the spacer height in the second sample contact area is more than 2 um.

D10. The method of any prior D embodiments, wherein the target-lysing component is white blood cell, the non-target-lysing component is platelet, and the spacer height in the first sample contact area is equal to or less than 1.0 um, 0.9 um, 0.8 um, 0.7 um, 0.6 um, 0.5 um, 0.4 um, 0.3 um, or 0.2 um, or in a range between any of the two values, and the spacer height in the second sample contact area is more than 1 um.

D11. The method of any prior D embodiments, wherein the target-lysing component is red blood cell, the non-target-lysing component includes white blood cell and platelets, and the spacer height in the first sample contact area is equal to or less than 2 um, 1.9 um, 1.8 um, 1.7 um, 1.6 um, 1.5 um, 1.4 um, 1.3 um, 1.2 um, 1.1 um, or 1.0 um, or in a range between any of the two values, and the spacer height in the second sample contact area is more than 2 um.

D12. The method of any prior D embodiments, wherein the target-lysing component includes red blood cell and white blood cell, the non-target-lysing component is platelet, and the spacer height in the first sample contact area is equal to or less than 1.0 um, 0.9 um, 0.8 um, 0.7 um, 0.6 um, 0.5 um, 0.4 um, 0.3 um, or 0.2 um, or in a range between any of the two values, and the spacer height in the second sample contact area is more than 1 um.

D13. The method of any prior D embodiments, wherein on one or both the sample contact areas, the respective plate further comprises a layer of a reagent.

D14. The method of embodiment D13, wherein the reagent facilitates: (a) the lysing of the targeted lysing component, and/or (b) the unlysing of non-targeted lysing components.

E1. The device or method of any prior embodiments, wherein the spacers have:
  i. a shape of pillar with substantially uniform cross-section and a flat top surface;
  ii. a ratio of the width to the height equal or larger than one;
  iii. a filling factor of equal to 1% or larger; and
  iv. a product of the filling factor and the Young's modulus of the spacer is 2 MPa or larger,
  wherein the filling factor is the ratio of the spacer contact area to the total plate area.

E2. The device or method of any prior embodiments, wherein an average value of the uniform thickness of the layer is substantially the same as the uniform height of the spacer with a variation of less than 10%.

E3. The device or method of any prior embodiments, wherein the sample further comprises a second target lysing component.

E4. The device or method of any prior embodiments, wherein in the closed configuration at least 90% of the target lysing component is lysed and at least 90% of the non-target lysing component is lysed.

E5. The device or method of any prior embodiments, wherein in the closed configuration at least 99% of the target lysing component is lysed and at least 99% of the non-target lysing component is lysed.

E6. The device or method of any prior embodiments, wherein in the closed configuration at least 90% of the all target lysing components lysed and at least 90% of the non-target lysing component is lysed.

E7. The device or method of any prior embodiments, wherein the variation of the layer of uniform thickness is less than 30 nm.

E8. The device or method of any prior embodiments, wherein the layer of uniform thickness sample has a thickness uniformity of up to +/−5%.

E8. The device or method of any prior embodiments, wherein the spacers are pillars with a cross-sectional shape selected from round, polygonal, circular, square, rectangular, oval, elliptical, or any combination of the same.

E9. The device or method of any prior embodiments, wherein analyzing the non-target component comprises counting the number of the non-lysing-target analyte and calculating the concentration of the non-target component.

E10. The device or method of any prior embodiments, wherein the spacers have:
  i. a shape of pillar with substantially uniform cross-section and a flat top surface;
  ii. a ratio of the width to the height equal or larger than one;
  iii. a predetermined constant inter-spacer distance that is in the range of 10 □m to 200 □m;
  iv. a filling factor of equal to 1% or larger; and
  v. a product of the filling factor and the Young's modulus of the spacer is 2 MPa or larger. wherein the filling factor is the ratio of the spacer contact area to a total plate area.

E10. The device or method of any prior embodiments, wherein pressing the plates into the closed configuration is conducted either in parallel or sequentially, the parallel pressing applies an external force on an intended area at the same time, and the sequential pressing applies an external force on a part of an intended area and gradually move to other area.

E11. The device or method of any prior embodiments, wherein the blood sample is stained before being analyzed.

E12. The device or method of any prior embodiments, wherein the blood sample is stained with acridine orange (AO).

E13. The device or method of any prior embodiments, wherein a staining reagent is coated on at least one sample contact area, and the blood sample is stained with the staining reagent.

E14. The device or method of any prior embodiments, wherein the blood sample is analyzed by:
  i. illuminating at least part of the blood sample in the layer of uniform thickness;
  ii. obtaining one or more images of the cells using a CCD or CMOS sensor;
  iii. identifying the platelets in the image using a computer; and
  iv. counting a number of platelets in an area of the image.

E15. The device or method of any prior embodiments, wherein the layer of uniform thickness sample has a thickness uniformity of up to +/−5%.

D. Blood Coagulation Assay (036)

In biological and chemical assays (e.g. diagnostic testing), often it needs to measure the volume, change the shape, and/or detect analytes of a sample or a part of the sample, quickly and simply. The current invention provides devices and methods for achieving these goals.

Among other things, the present invention can be used to measure blood coagulation. Coagulation (also known as clotting) is the process by which blood changes from a liquid to a gel, forming a blood clot. It potentially results in hemostasis, the cessation of blood loss from a damaged vessel, followed by repair. A blood clot consists of a plug of platelets enmeshed in a network of insoluble fibrin molecules. The mechanism of coagulation involves activation, adhesion, and aggregation of platelets along with deposition and maturation of fibrin. Disorders of coagulation are disease states which can result in bleeding (hemorrhage or bruising) or obstructive clotting (thrombosis). Essential factors for blood coagulation include: the proteolytic enzyme thrombin, calcium ions ($Ca^{2+}$) and other protein clotting factors.

Early identification of coagulopathy has important clinical implications for managing patients who are critically ill, severely injured, or on anticoagulation therapy. Rapid and accurate assessments are essential to ensure that patients prone to blood clots—as well as those who have difficulty clotting—receive appropriate care to their conditions. Traditional tests (prothrombin time (PT) and activated partial thromboplastin time (aPTT) test) need to be conducted in a professional testing facility and require up to 10 mL blood. Consequently, a simple and portable assay that is fast, easy to use, and/or inexpensive is desirable.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. No. 62/456,065, filed on Feb. 7, 2017 and U.S. Provisional Application No. 62/456,287, which was filed on Feb. 8, 2017, and U.S. Provisional Application No. 62/456,504, which was filed on Feb. 8, 2017, all of which is incorporated herein in their entirety for all purposes.
Examples of QMAX Electrical Measurement of Blood Permittivity for Blood Coagulation Test FIG. 23 shows an embodiment of a QMAX (Q: quantification; M: magnifying; A: adding reagents; X: acceleration; also known as compressed regulated open flow (CROF)) device, which comprises a first plate (In some embodiments marked as "substrate") 10, a second plate (In some embodiments marked as "X-plate") 20, and spacer (marked as "pillars") 40.

Panel (A) of FIG. 23 shows a sectional view of the plates in an open configuration, in which the plates 10 and 20 are partially or entirely separated apart, allowing a sample (e.g. blood sample) 90 to be deposited on either one or both of the plates. As shown in panel (A), in some embodiments, the sample is blood. In certain embodiments, the sample comprises blood serum. In certain embodiments, the sample comprises whole blood. In certain embodiments, the sample is a blood sample comprising added $Ca^{2+}$. In certain embodiments, the sample is a blood sample comprising citrate salt or acid for anti-coagulation purposes. In some embodiments, the sample comprises added anticoagulant corn trypsin inhibitor (CTI). In certain embodiments, the sample further comprises added anticoagulant penicillins. In some embodiments, the sample comprises added Activator cephalin. In some embodiments, the sample further comprises added Activator Tissue Factors (ATF).

Coagulation can also be affected by temperature. In some embodiments, temperature can be 0° C., 10° C., 20° C., 50° C., 100° C., or a range between any two of the values; and a preferred value of 37° C. that mimics body temperature. A unit of temperature controller can be added to maintain desired temperature.

In some embodiments, the surface of the first plate 10 facing the second plate 20 is defined as the inner surface; the surfaces of the second plate 20 that faces the first plate 10 is also defined as the inner surface of the second plate 20. As shown in panel (A) of FIG. 23, the first plate 10 can comprises spacers 40 that are fixed on the inner surface of the first plate 10. It should be noted, however, that in some embodiments that spacers 40 are fixed on the inner surface of the second plate 20 and in other embodiments on the inner surfaces of both the second plate 20 and the first plate 10.

As shown in panel (A), each of the plates 10 and 20 can respectively comprises one or more electrodes positioned at the inner surfaces of the plates. In some embodiments, the electrodes are attached to the inner surfaces of the plates 10 and 20. As shown in panel (A), electrode 80 is attached to the inner surface of the first plate 10, and electrode 85 is attached to the inner surface of the second plate 20. In some embodiments, there is only one electrode for one plate. In some embodiments, there are a plurality of electrodes for one plate. The electrodes are made from conductive materials. In some embodiments, the electrodes are made from metal such as but not limited to: aluminum, silver and copper and alloys and mixtures thereof.

The plates 10 and 20 are moveable relative to each other into different configuration. One of the configurations is an open configuration, in which the two plates are partially or entirely separated apart and the spacing between the plates are not regulated by the spacers 40. Panel (A) of FIG. 23 shows the plates in the open configuration, in which a sample 90, such as but not limited to blood, can be added to first plate 10, the second plate 20, or both of the plates 10 and 20. In some embodiments, the inner surface of a respective plate comprises a sample contact area, which occupies a part of the entirety of the inner surface. In certain embodiments, the spacers 40 are positioned within the sample contact area. In some embodiments, the spacers 40 are not fixed to any one of the plates, but are mixed in the sample 90. In some embodiments, the sample 90 is blood.

Another of the configurations between the plates 10 and 20 is a closed configuration. Panel (B) of FIG. 23 shows the sectional view of the plates at the closed configuration, in which the inner surfaces of the plates 10 and 20 are pressed against each other, at least part of the sample 90 is pressed into a layer of highly uniform thickness. In some embodiments, the layer of uniform thickness is confined by the inner surfaces of the two plates and the thickness is regulated by the height of the spacers 40. In some embodiments, the uniform thickness of the sample 90 is the same as the spacing between the plates 10 and 20; in certain embodiments the thickness of the sample 90 and the spacing between the plates are the same as the height of the spacers 40. When the plates are in the closed configuration, the electrodes 80 and 85 are in contact with at least part of the sample 90. In certain embodiments, the electrodes 80 and 85 are in contact with the part of sample 90 that is pressed into a layer of highly uniform thickness.

In some embodiments, the spacer has a height of 1 μm, 10 μm, 100 μm, 1 mm, 1 cm, or a range between any two of the values; and a preferred range of 10 μm to 100 μm that is physiologically relevant which provides a more realistic geometrical representation of the human microvessels.

As shown in panel (B) of FIG. 23, in some embodiments the device of the present invention further comprises a power source 100, such as but not limited to an electricity source that provides alternative current (AC) or direct current (DC). In some embodiments, the power source 100 is operably connected to electrodes 80 and 85, which are in contact with the layer of the sample 90 that is pressed into a layer of highly uniform thickness. In some embodiments, the device of the present invention further comprises a measuring unit, which can be used to measure the electric signals of the sample 90. In some embodiments, the electric signals include current, potential, conductivity, and/or capacitance. In some embodiments, AC has a frequency of 100 Hz, 1 kHz, 10 kHz, 100 kHz, 1 MHz, 10 MHz, 100 MHz, 1000 MHz, or a range between any two of the values; and a preferred range of 1 kHz to 10 kHz, 10 kHz to 100 kHz, or 100 kHz to 1 MHz.

wherein the capacitance, proportional to the permittivity of the sample, between measuring electrodes are measured and recorded after loading the sample in the device at time of 10 s, 30 s, 60 s, 2 min, 3 min, 5 min, 8 min, 10 min, 15 min, 20 min, 30 min or a range between any two of the values;

wherein the electrodes are metal, selected from gold, copper, silver, aluminum, or a mixture thereof, or an alloy made of any metals thereof, wherein the electrodes are conductive metallic oxide or metallic compound, selected from indium tin oxide (ITO), zinc oxide (ZnO), titanium oxide (TiOx), molybdenum dioxide (MoO2), lithium fluoride (LiF) or a combination thereof, wherein the electrodes are conductive small molecule and conductive polymer, selected from poly(3,4-ethylenedioxythiophene) poly(styrenesulfonate) (PEDOT:PSS), fullerene derivatives (as C60), aluminum tris (8-hydroxyquinoline)(Alq3), or a combination thereof, wherein the electrodes are metal, selected from gold, copper, silver, aluminum, or a mixture thereof, or an alloy made of any metals thereof, wherein the electrodes are conductive metallic oxide or metallic compound, selected from indium tin oxide (ITO), zinc oxide (ZnO), titanium oxide (TiOx), molybdenum dioxide (MoO2), lithium fluoride (LiF) or a combination thereof, wherein the electrodes are conductive small molecule and conductive polymer, selected from poly(3,4-ethylenedioxythiophene) poly(styrenesulfonate) (PEDOT:PSS), fullerene derivatives (as C60), aluminum tris (8-hydroxyquinoline)(Alq3), or a combination thereof, The device of paragraph A1, wherein at least one of the electrodes connects to the anode of electrical source, one of the electrodes connects to the cathode of electrical source, these two electrodes are measuring electrodes.

A device of paragraph A1, wherein all measuring electrodes on first plate or all measuring electrodes on second plate;

A device of paragraph A1, wherein both first and second plate have measuring electrodes;

A device of paragraph A1, wherein all electrodes are outside, non-contact to the first and second plates;

A device of paragraph A1, wherein the width of electrodes is 2 times larger than the height and the gap between two measuring electrodes, wherein the width of electrodes is 5 times larger than the height and the gap between two measuring electrodes, wherein the width of electrodes is 10 times larger than the height and the gap between two measuring electrodes, wherein the width of electrodes is 100 times larger than the height and the gap between two measuring electrodes, wherein the width of electrodes is 1000 times larger than the height and the gap between two measuring electrodes, A device of paragraph A1, wherein the height of electrodes is 1 nm, 10 nm, 50 nm, 100 nm, 500 nm, 1 um, 10 um, 50 um, 100 um, 500 um, 1 mm, 5 mm, 10 mm, or a range between any two of the values;

A device of paragraph A1, wherein the width of electrodes is 1 nm, 10 nm, 50 nm, 100 nm, 500 nm, 1 um, 10 um, 50 um, 100 um, 500 um, 1 mm, 5 mm, 10 mm, 50 mm, 100 mm, or a range between any two of the values;

A device of paragraph A1, wherein the gap between two electrodes is 1 nm, 10 nm, 50 nm, 100 nm, 500 nm, 1 um, 10 um, 50 um, 100 um, 500 um, 1 mm, 5 mm, 10 mm, 50 mm, 100 mm, or a range between any two of the values.

The Process of Using the QMAX Device to Electrical Measure Permittivity

The QMAX devices for electrical measurement can be used for various purposes. For example, in some embodiments, the device is used to measure sample permittivity. In certain embodiments, when the sample is blood, the permittivity values can be converted into parameters related to blood coagulation.

Figure 24:
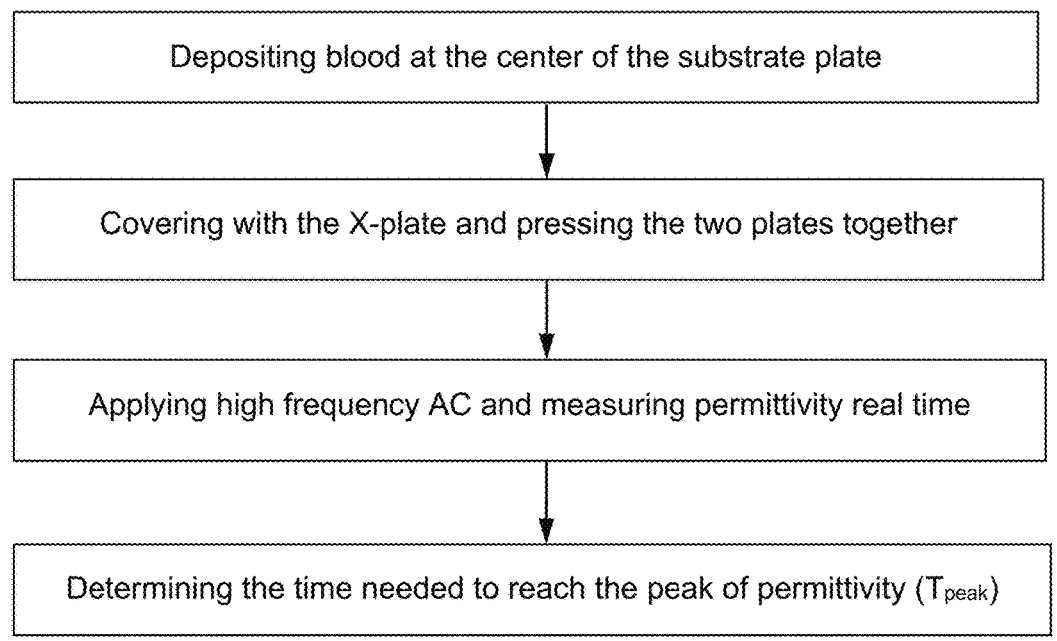
FIG. 24 is a flow chart showing the basic steps in an exemplary process to measure sample permittivity using a QMAX electrical measurement device.

FIG. 24 provides an exemplary flow chart for the process of measuring of permittivity of a blood sample. It should be noted, however, the device of the present invention can be used in various assays, including but not limited to measuring the permittivity, and thus coagulation characteristics of blood. As shown in FIG. 24, in some embodiments, the process includes: (1) depositing blood at the center of the substrate plate; (2) covering with the X-plate and pressing the two plate together; (3) applying high frequency AC and measuring permittivity real time; and (4) determining the time needed to reach the peak of permittivity ($T_{peak}$).

In some embodiments, the method of analyzing permittivity of a liquid sample can comprise:

(a) obtaining the liquid sample;

(b) obtaining a device, which comprises a first plate, a second plate, and spacers fixed on one or both of the plates; wherein: (i) the plates are movable relative to each other into different configurations, including an open configuration and a closed configuration; (ii) each plate respectively comprises an inner surface that has a sample contact area for contacting a sample, and (iii) the spacers have a predetermined substantially uniform height, and (iv) each plate respectively comprises one or a plurality of electrodes;

(c) depositing the sample on one or both of the plates when the plates are in an open configuration, wherein in the open configuration the two plates are partially or entirely separated apart and the spacing between the plates is not regulated by the spacers; and (d) after (c), bringing the two plates together and pressing the plates into a closed configuration, wherein in the closed configuration: at least part of the sample is compressed by the two plates into a layer of highly uniform thickness, which is confined by the inner surfaces of the two plates and is regulated by the spacers, and the electrodes are in contact with the sample at the layer of uniform thickness; and (e) through the electrodes, measuring electric properties (e.g. currents, capacitance, potential, and/or conductance) of the sample at the layer of uniform thickness.

There are various types of samples that can be analyzed by the device and method of the present invention. One particular example is a blood sample. In certain embodiments, the sample comprises processed blood or blood component, such as but not limited to blood serum. In certain embodiments, the sample comprises whole blood. In certain embodiments, the sample further comprises added $Ca^{2+}$. In certain embodiments, the sample further comprises added citrate acid or salt. In some embodiments, the sample with added $Ca^{2+}$ and citrate can be used as controls.

In some embodiments, certain characteristics of the permittivity of the blood sample, and particular, the permittivity of the blood sample at the layer of highly uniform thickness when the plates are in the closed configuration, can be used as an indicator for blood coagulation properties. In certain embodiments, permittivity parameters, such as but not limited to $T_{peak}$ can be used to assess blood coagulation qualitatively or quantitatively. In certain embodiments, certain permittivity parameters can be used to calculate and/or estimate PT or aPPT.

Example for Measurement of Permittivity

Figure 25:
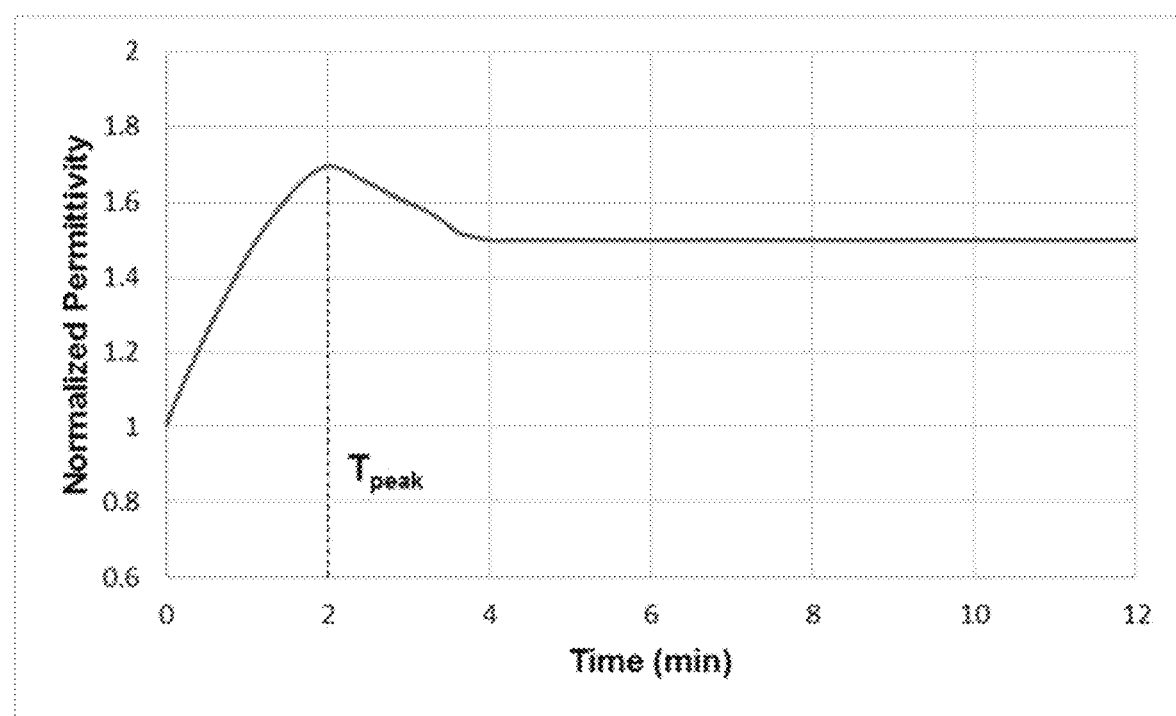
FIG. 25 shows am example of measurement results of sample permittivity.

FIG. 25 provides an example of permittivity measurement results. The blood sample is loaded into the device as shown in FIG. 23 according to the process as shown in FIG. 2; a 1 MHz AC with bias 0.1V is applied to the sample and the permittivity is measured. Time 0 is when the blood is added to the device. The results are shown in FIG. 25, which illustrates a normalized $T_{peak}$ of 2 minutes. The permittivity, along with the coagulation properties, of various samples, can be measured and assessed accordingly.

Example of QMAX Measurement of Blood Absorbance for Blood Coagulation Test

Figure 26:
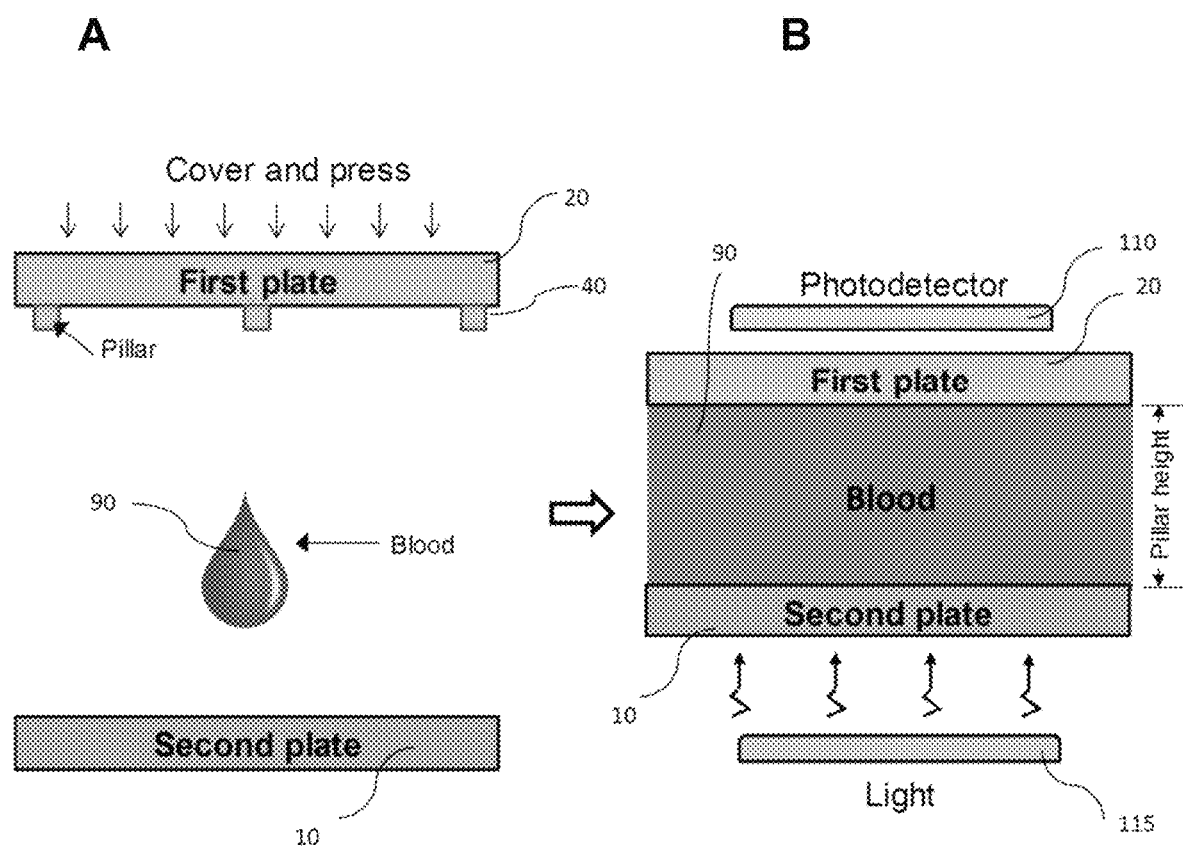
FIG. 26 is a schematic drawing for an exemplary embodiment of a QMAX (Q: quantification; M: magnifying; A: adding reagents; X: acceleration; also known as compressed regulated open flow (CROF)) device for measurement of absorbance of blood.

FIG. 26 shows an embodiment of a QMAX (Q: quantification; M: magnifying; A: adding reagents; X: acceleration; also known as compressed regulated open flow (CROF)) device, which comprises a first plate (In some embodiments marked as "substrate") 10, a second plate (In some embodiments marked as "X-plate") 20, and spacer (marked as "pillars") 40. Panel (A) of FIG. 26 shows a sectional view of the plates in an open configuration, in which the plates 10 and 20 are partially or entirely separated apart, allowing a sample (e.g. blood sample) 90 to be deposited on either one or both of the plates. As shown in panel (A), in some embodiments, the sample is blood. In certain embodiments, the sample comprises blood serum. In certain embodiments, the sample comprises whole blood. In certain embodiments, the sample is a blood sample comprising added $Ca^{2+}$. In certain embodiments, the sample is a blood sample comprising citrate salt or acid for anti-coagulation purposes. In some embodiments, the sample comprises added anticoagulant corn trypsin inhibitor (CTI). In some embodiments, the sample further comprises added anticoagulant penicillins. In some embodiments, the sample comprises added Activator cephalin. In some embodiments, the sample further comprises added Activator Tissue Factors (ATF).

Coagulation can also be affected by temperature. In some embodiments, temperature can be 0° C., 10° C., 20° C., 50° C., 100° C., or a range between any two of the values; and a preferred value of 37° C. that mimics body temperature. A unit of temperature controller can be added to maintain desired temperature.

In some embodiments, the surface of the first plate 10 facing the second plate 20 is defined as the inner surface; the surfaces of the second plate 20 that faces the first plate 10 is also defined as the inner surface of the second plate 20. As shown in panel (A) of FIG. 26, the first plate 10 can comprises spacers 40 that are fixed on the inner surface of the first plate 10. It should be noted, however, that in some embodiments that spacers 40 are fixed on the inner surface of the second plate 20 and in other embodiments on the inner surfaces of both the second plate 20 and the first plate 10.

The plates 10 and 20 are moveable relative to each other into different configuration. One of the configurations is an open configuration, in which the two plates are partially or entirely separated apart and the spacing between the plates are not regulated by the spacers 40. Panel (A) of FIG. 26 shows the plates in the open configuration, in which a sample 90, such as but not limited to blood, can be added to first plate 10, the second plate 20, or both of the plates 10 and 20. In some embodiments, the inner surface of a respective plate comprises a sample contact area, which occupies a part of the entirety of the inner surface. In certain embodiments, the spacers 40 are positioned within the sample contact area. In some embodiments, the spacers 40 are not fixed to any one of the plates, but are mixed in the sample 90. In some embodiments, the sample 90 is blood.

Another of the configurations between the plates 10 and 20 is a closed configuration. Panel (B) of FIG. 26 shows the sectional view of the plates at the closed configuration, in which the inner surfaces of the plates 10 and 20 are pressed against each other, at least part of the sample 90 is pressed into a layer of highly uniform thickness. In some embodiments, the layer of uniform thickness is confined by the inner surfaces of the two plates and the thickness is regulated by the height of the spacers 40. In some embodiments, the uniform thickness of the sample 90 is the same as the spacing between the plates 10 and 20; in certain embodiments, the thickness of the sample 90 and the spacing between the plates are the same as the height of the spacers 40.

In some embodiments, the device comprises an electromagnetic radiation source and a detector. In certain embodiments, the electromagnetic radiation source is configured to controllable emit electromagnetic waves that pass through or reflect from the plates when the plates are in the closed configuration.

In some embodiments, the plates are transparent and the electromagnetic waves pass through the plates. In some embodiments, one of the plates is reflective and the electromagnetic waves is reflected.

In some embodiments, the electromagnetic waves have the same wavelength. In certain embodiments, the electromagnetic waves are visible light, ultraviolet light, infrared light, or waves with other wavelengths. In some embodiments, the detector is further configured to calculate the absorption of the electromagnetic waves by the blood sample. In certain embodiments, the detector and the electromagnetic radiation source are on the same side of the plates when the plates are in the closed configuration. In certain embodiments, the detector and the electromagnetic radiation source are on different sides of the plates when the plates are in the closed configuration.

In some embodiments, the spacer has a height of 1 µm, 10 µm, 100 µm, 1 mm, 1 cm, or a range between any two of the values; and a preferred range of 10 µm to 100 µm that is physiologically relevant which provides a more realistic geometrical representation of the human microvessels.

In some embodiments, the first and second plate can be made of any material that is transparent or semi-transparent or reflective with flat or engineered solid surface. Examples are but not limited to plastic or glass.

As shown in panel (B) of FIG. 26, in some embodiments the device of the present invention further comprises a light source 115 and a photodetector 110.

Light can be provided by any objects that generate photons that can be detected by photodetector. Examples are but not limited to LED, halogen lamp or laser diode.

Light can be visible or invisible. In some embodiments, light has a wavelength of 1 nm, 10 nm, 100 nm, 1 µm, 10 µm, 100 μm, or a range between any two of the values; and a preferred range of 400 nm to 700 nm.

In some embodiments, light can be provided from outer side, or on, or in, or from inner side of either plate.

In some embodiments, the direction of light can be from first plate to second plate or vice versa.

The Process of Using the QMAX Device to Measure Absorbance

Figure 27:
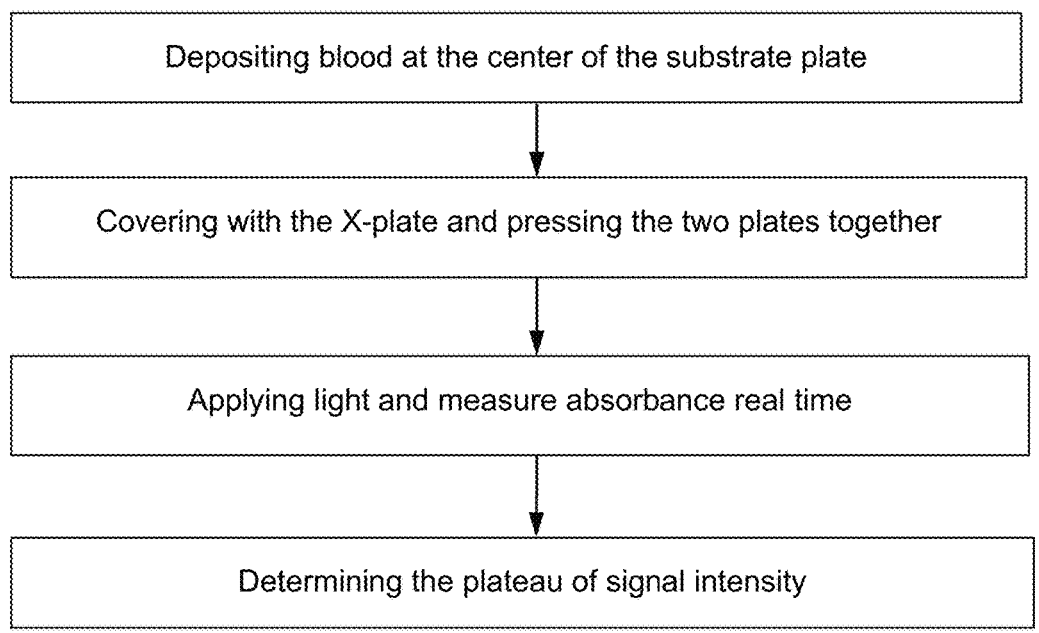
FIG. 27 is a flow chart showing the basic steps in an exemplary process to measure sample absorbance using a QMAX device.

FIG. 27 provides an exemplary flow chart for the process of measuring of absorbance of a blood sample. As shown in FIG. 27, in some embodiments, the process includes: (1) depositing blood at the center of the substrate plate; (2) covering with the X-plate and pressing the two plate together; (3) applying light and measure absorbance real time; and (4) determining the plateau of signal intensity.

In some embodiments, the method of analyzing absorbance of a liquid sample can comprise:
  (a) obtaining a device as shown in FIG. 26 and/or as described above for the measurement of absorbance,
  (b) depositing the blood sample on the one or both of the plates in the open configuration;
  (c) after (b), bringing the two plates together and pressing the plates into the closed configuration,
  (d) starting the electromagnetic radiation source to emit electromagnetic waves onto the layer of the sample confined in the plates; and
  (e) measuring absorption or reflection of the electromagnetic waves.

There are various types of samples that can be analyzed by the device and method of the present invention. One particular example is a blood sample. In certain embodiments, the sample comprises processed blood or blood component, such as but not limited to blood serum. In certain embodiments, the sample comprises whole blood. In certain embodiments, the sample further comprises added $Ca^{2+}$. In certain embodiments, the sample further comprises added citrate acid or salt. In some embodiments, the sample with added $Ca^{2+}$ and citrate can be used as controls.

In some embodiments, certain characteristics of the absorbance of the blood sample, and particular, the absorbance of the blood sample at the layer of highly uniform thickness when the plates are in the closed configuration, can be used as an indicator for blood coagulation properties. In certain embodiments, absorbance parameters, such as but not limited to the plateau of signal intensity can be used to assess blood coagulation qualitatively or quantitatively. In certain embodiments, certain absorbance parameters can be used to calculate and/or estimate PT or aPPT.

Example for Measurement of Absorbance

Figure 28:
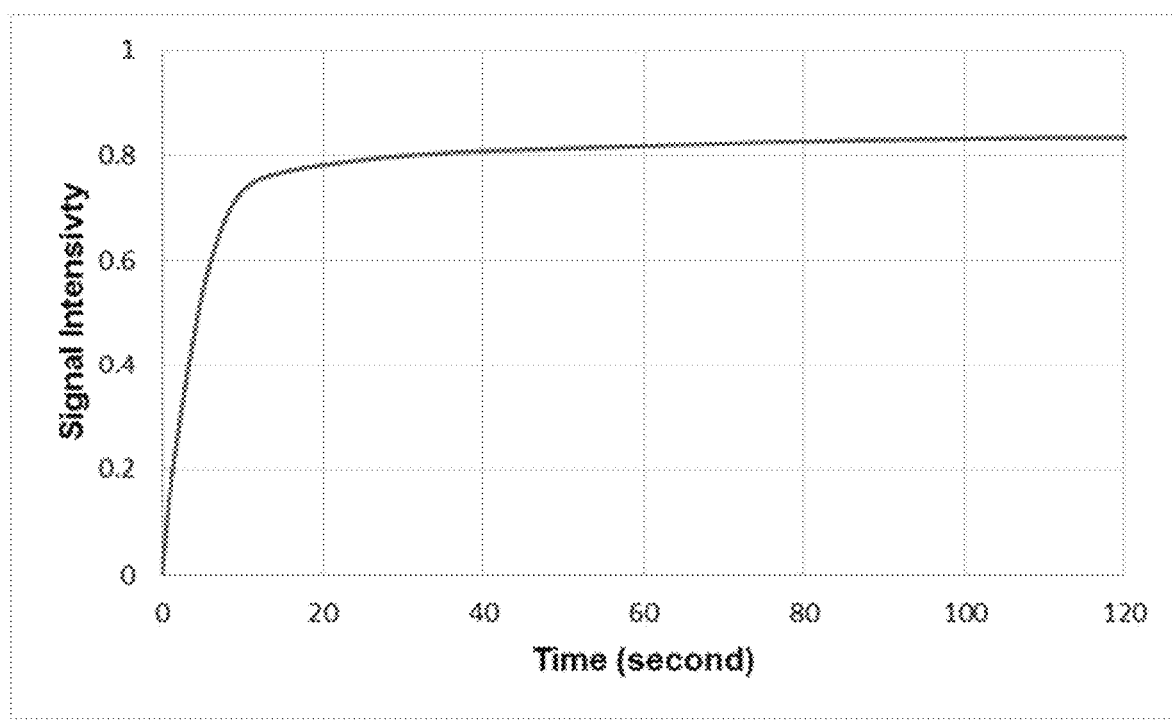
FIG. 28 shows an example of measurement results of sample absorbance.

FIG. 28 provides an example of absorbance measurement results. The blood sample is loaded into the device as shown in FIG. 26 according to the process as shown in FIG. 27; a white light source from LED is applied to the sample and the absorbance is measured. Time 0 is when the blood is added to the device. The results are shown in FIG. 28, which illustrates a plateau of absorption signal intensity after 20 seconds. The absorbance, along with the coagulation properties, of various samples, were measured and assessed accordingly.

A1. A device for analyzing blood coagulation, comprising:
  a first plate, a second plate, spacers, and a detection unit wherein:
    v. the plates are movable relative to each other into different configurations;
    vi. each of the plates respectively comprises an inner surface that has a sample contact area for contacting a blood sample;
    vii. the spacers have a predetermined substantially uniform height; and
      wherein one of the configurations is an open configuration, in which: the two plates are partially or entirely separated apart, the spacing between the plates is not regulated by the spacers, and the blood sample is deposited on one or both of the plates;
      wherein another of the configurations is a closed configuration, which is configured after the sample deposition in the open configuration, and in the closed configuration: at least one spacer is between the two plates, at least part of the blood sample deposited is compressed by the plates into a layer of highly uniform thickness and is substantially stagnant relative to the plates, wherein the uniform thickness of the layer is confined by the inner surfaces of the two plates and is regulated by the plates and the spacers; and
      wherein the plates and the detection unit are configured to measure coagulation of the blood sample.

B1. The device of embodiment A1, wherein the detection unit comprises:
  i. a source of electromagnetic radiation; and
  ii. a detector;
    wherein the electromagnetic radiation source is configured to controllable emit electromagnetic waves that pass through or reflect from the plates when the plates are in the closed configuration.

B2. The device of embodiment B1, wherein the plates are transparent and the electromagnetic waves pass through the plates.

B3. The device of embodiment B1, wherein one of the plates is reflective and the electromagnetic waves is reflected.

B4. The device of any prior B embodiments, wherein the electromagnetic waves have the same wavelength.

B5. The device of any prior B embodiments, wherein the electromagnetic waves are visible light, ultraviolet light, infrared light, or waves with other wavelengths.

B6. The device of any prior B embodiments, wherein the detector is further configured to calculate the absorption of the electromagnetic waves by the blood sample.

B7. The device of any prior B embodiments, wherein the detector and the electromagnetic radiation source are on the same side of the plates when the plates are in the closed configuration.

B8. The device of any prior B embodiments, wherein the detector and the electromagnetic radiation source are on different sides of the plates when the plates are in the closed configuration.

C1. A method of measuring blood coagulation, comprising:
  (a) obtaining a device of any of the B embodiments,
  (b) depositing the blood sample on the one or both of the plates in the open configuration;
  (c) after (b), bringing the two plates together and pressing the plates into the closed configuration,
  (d) starting the electromagnetic radiation source to emit electromagnetic waves onto the layer of the sample confined in the plates;

(e) measuring absorption or reflection of the electromagnetic waves.

C3. The method of embodiment C1, further comprising assessing the coagulation properties of the blood sample.

C3. The method of any prior C embodiments, further comprising calculating the prothrombin time (PT) and activated partial thromboplastin time (aPTT) based on the absorption or reflection of the blood sample.

D1. The device of embodiment A1, wherein the detection unit comprises one or a plurality of electrodes which are configured to measure the permittivity of the sample.

D2. The device of any prior D embodiments, wherein at least one of the spacers comprises one of the electrode.

D3. The device of any prior D embodiments, wherein all the electrodes are on one or both of the inner surfaces of the plates.

D4. The device of any prior D embodiments, wherein all the electrodes are on the outside surface of the plates.

D5. The device of any prior D embodiments, further comprising a barrier membrane, which is configured to allow the passing through of selected analytes in the sample, and block other analytes.

D6. The device of any prior D embodiments, further comprising a barrier membrane, wherein the sample is in communication with the barrier membrane through a barrier membrane contacting surface.

D7. The device of any prior D embodiments, further comprising a barrier membrane, which is made of insoluble, infusible synthetic organic polymer matrix which is bound with chemicals that selectively allow certain analytes in sample to pass through the barrier membrane.

D8. The device of any prior D embodiments, further comprising a barrier membrane, which is made of organic polymer matrix selected from the group consisting of poly(vinyl chloride) (PVD), polyvinylpyrrolidone, polydimethylsiloxane, perfluoropolyether, etc. The chemicals functions as selecting pass certain analyte are from ETH 157 carrier, ETh 227 carrier, ETH 2120 carrier, a bis(12-crown-4) compound, hemispherand, valinomycin, BBPA, KTpDIPB, and '70 o-nitrophenyl octyl ether, etc.

D9. The device of any prior D embodiments, wherein the barrier membrane is coated on top of the electrodes.

D10. The device of any prior D embodiments, wherein one of the electrodes comprises a perforated conductive sheet which provides the function of barrier membrane contacting surface.

D11. The device of any prior D embodiments, wherein the electrodes are connected to an electric circuit, which is configured to measure the permittivity of the sample.

D12. The device of any prior D embodiments, wherein the electrodes are made from a metal or conductive metallic oxide or metallic compound.

D13. The device of any prior D embodiments, further comprising an electricity source that applies an electrical potential to the measuring electrodes.

D14. The device of any prior D embodiments, wherein the electricity source provides an alternative current (AC) or a direct current (DC).

D15. The device of any prior D embodiments, wherein selected electrolytes in the sample pass through the barrier membrane and in communication with at least one of the electrode as a result of the electrical source.

E1. A method of analyzing permittivity of a blood sample, comprising:
(a) obtaining a device of any D embodiments;
(b) depositing the blood sample on one or both of the plates when the plates are in the open configuration,
(c) after (b), bringing the two plates together and pressing the plates into the closed configuration,
(e) measuring permittivity of the sample at the layer of uniform thickness by detecting electric signals from the electrodes.

E2. The method of any prior E embodiment, wherein the device further comprises a measuring unit that is configured to measure the permittivity of the sample.

E3. The method of any prior E embodiments, further comprising assessing coagulation of the blood sample based on permittivity of the blood sample.

E4. The method of any prior E embodiments, further comprising assessing prothrombin time (PT) of the blood sample.

E5. The method of any prior E embodiments, further comprising assessing activated partial thromboplastin time (aPTT) of the blood sample.

F1. The device or method of any prior embodiments, wherein the sample comprises blood serum.

F2. The device or method of any prior embodiments, wherein the sample comprises whole blood.

F3. The device or method of any prior embodiments, wherein the sample further comprises added $Ca^{2+}$.

F4. The device or method of any prior embodiments, wherein the sample further comprises added citrate acid or salt.

F5. The device or method of any prior embodiments, wherein the sample further comprises added anticoagulant corn trypsin inhibitor (CTI).

F6. The device or method of any prior embodiments, wherein the sample further comprises added anticoagulant penicillins.

F7. The device or method of any prior embodiments, wherein the sample further comprises added Activator cephalin.

F8. The device or method of any prior embodiments, wherein the sample further comprises added Activator Tissue Factors.

F9. The device or method of any prior embodiments, wherein the height of the spacer is less than 1 um, 10 um, 100 um, or 1 cm, or in a range between any of the two values.

F10. The device or method of any prior embodiments, wherein a coagulation regulator is predeposited and dried on one or both of the plates, F11. The device or method of any prior embodiments, wherein coagulation regulator is peptides, proteins (e.g. Tissue Factors) or small molecules (e.g. ions, antibiotics and other drugs).

E. Rapid AphaLISA Assay (007)

In biological and chemical assays (e.g. diagnostic testing), the binding of two beads in a solution is used for assaying, where each bead is a different type (often coated with a different capture agent), and is, prior to the binding, in a different location of the solution. However, the binding time is typically in the range of 30 mins to hours. The present invention provides the devices and methods that can reduce the binding time into a few minutes or even less than 60 sec.

One aspect of the present invention is to accelerate the bead binding time by making, prior to a binding, the two different types of beads located a vicinity from each other, such that the two types of beads will recombine without diffusing through a long distance (hence without a long diffusion time).

Another aspect of the present invention is to accelerate the bead binding time by (a) prior to providing a liquid sample, putting one type of the beads on an inner surface of a first plate and another of the beads on an inner surface of a second plate, (b) providing a sample to be assayed between the inner surfaces of the two plates, (c) pressing the plates into a final configuration that has a smaller plate-spacing than that before pressing the plates, and (d) releasing the beads on the inner surface of the plates into the solution, wherein the spacing in the final configuration is equal to or less than 150 microns.

Another aspect of the present invention is to accelerate the bead binding time by making at least portion of the final sample film having a significant uniform thickness.

Another aspect of the present invention is to accelerate the bead binding time by making at least portion of the final sample film having a significant uniform thickness, wherein the uniform thickness is regulated by a plurality of spacers.

Another aspect of the present invention is to accelerate the bead binding time by making at least portion of the final sample film having a significant uniform thickness, wherein the uniform thickness is regulated by a plurality of spacers, and the final sample film is achieved by hand pressing the outer surface of the plates.

Another aspect of the present invention is to accelerate the bead binding time of the bead pairs, wherein the bead pairs form the basis for the assay, and wherein one bead of the bead pair is a donor bead, and the other an acceptor bead, the donor bead releasing converting matter or energy that stimulates the acceptor bead in the proximity of the donor bead to provide or modify a signal.

1. Device

Figure 20:
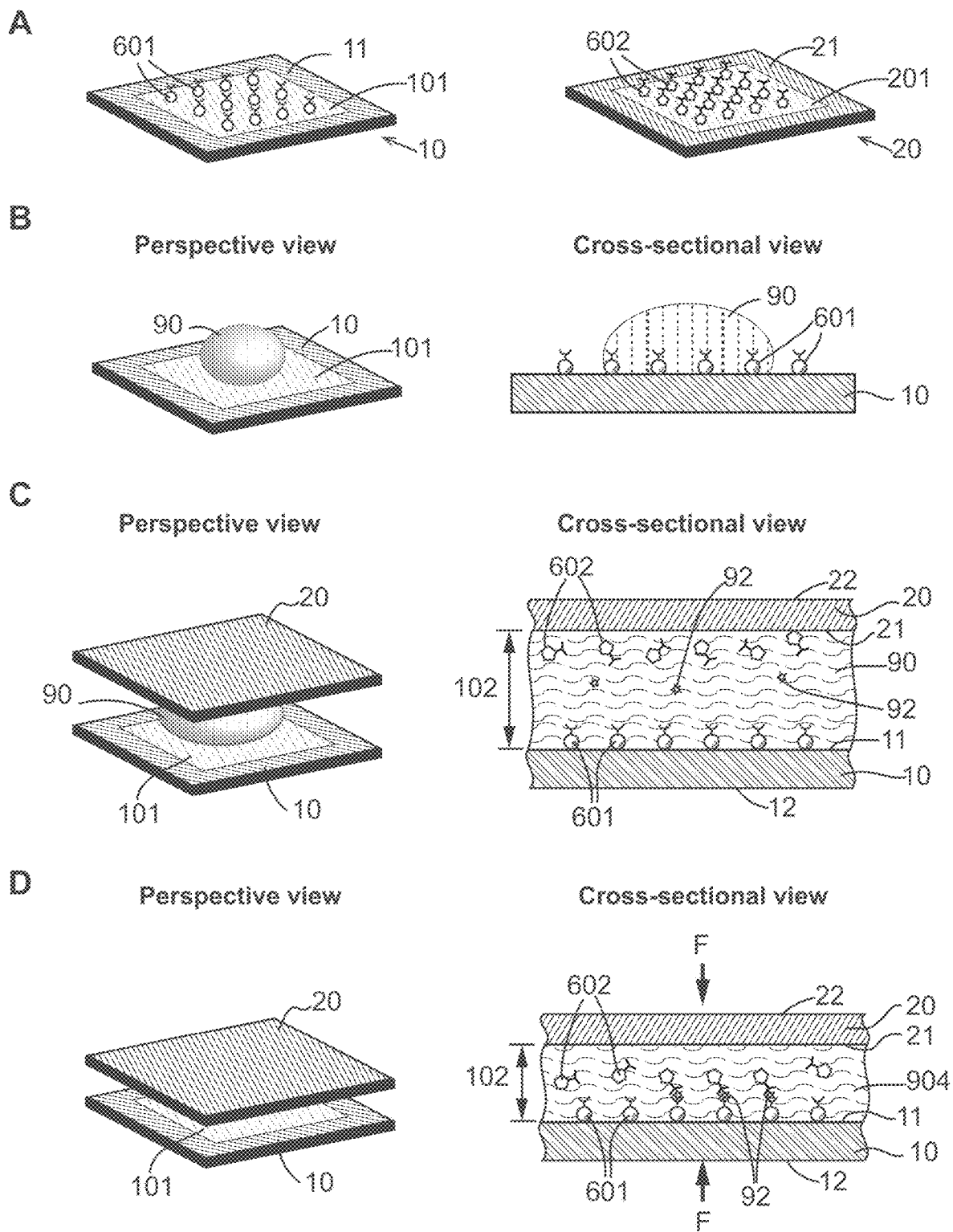
FIG. 20 shows an exemplary embodiment of a device for analyzing a liquid sample provided by the present invention.

One aspect of the present invention is a device for analyzing a liquid sample. FIG. 20 schematically shows an exemplary embodiment of the device, which comprises a first plate 10, a second plate 20, a spacing mechanism (not shown), and at least one first bead 601 and at least one second bead 602.

In particular, FIG. 20 panel (A) shows the perspective view of the first plate 10 and second plate 20. As illustrated in the figure, each plate respectively comprises an inner surface (11 and 21, respectively) and an outer surface (12 and 22, respectively, not shown here), and each inner surface has a sample contact area (not indicated) for contacting a sample that may contain a target analyte. Furthermore, the first plate inner surface 11 and the second plate inner surface 21 both have, in its respective sample contact area, a binding site (101 and 201 respectively) that has a predetermined area. As shown in the figure, at least one first bead 601 is coated on the first plate binding site 101, at least one second bead 602 is coated on the second plate binding site 201. It should be noted, however, there may be more than one binding sites on each respective plate, and each binding site may have one or a plurality of the first or second beads. It is also possible that the first bead 601 is coated on the second plate binding site 201, and the second bead 602 is coated on the first plate binding site 101. In some embodiments, the first bead 601 and the second bead 602 may coexist on the same plate inner surface, coated on different binding sites or even the same binding site(s), as long as their main functions in the assay as disclosed below is not affected by their physical proximity. In addition, it should be noted that the device serves as an example for the features shown in all figures and described thereof. In general, in the drawings, elements that are optional or alternatives are illustrated in dashed lines. Elements that serve a similar, or at least substantially similar, purpose are labeled with numbers consistent among the figures. Like numbers in each of the figures, and the corresponding elements, may not be discussed in detail herein with reference to each of the figures. Similarly, all elements may not be labeled or shown in each of the figures, but reference numerals associated therewith may be used for consistency. Elements, components, and/or features that are discussed with reference to one or more of the figures may be included in and/or used with any of the figures without departing from the scope of the present disclosure. Elements shown in each of the figures are for illustrative purposes only, their relative positioning, proportions, and/or sequences may be altered in particular embodiments without departing from the scope of the present disclosure.

1.1. Bead and Assay Type

The first bead 601 and the second bead 602 are respectively configured to serve at least two functions: affinity binding and providing a bead pair-related signal. It usually comprises a nanoparticle as the backbone such as, but not limited to, carbon nanotubes, fullerenes, dendrimers, quantum dots, noble metal nanoparticles, fluorophore-doped nanoparticles, rare earth-doped nanoparticles, superparamagnetic nanoparticles, and any combination thereof. The term "nanoparticle" as used herein refers to any type of nanoscale particles in the size of 1 nm to 5 μm. In some embodiments, the bead may further comprise a binding agent for the affinity binding as disclosed blow that is conjugated, or attached by any other interaction type, to the nanoparticle. The binding agent may be selected from a group of molecules such as, but not limited to, protein, peptide, peptidomimetics, streptavidin, biotin, oligonucleotide, oligonucleotide mimetics, any other affinity binding ligand and any combination thereof. In some embodiments, the bead may further comprise a signal unit that is contained within or attached to the nanoparticle and configured to provide or modify the bead pair-related signal.

The first bead 601 and the second bead 602 constitute a bead pair. They may be configured to bind to each other specifically in a target analyte-related manner, so that they may bind to each other in a specific manner either directly, or indirectly, or both, and their binding is affected by the concentration of the target analyte. In some embodiments, particularly in certain competitive bio/chemical assays the device may be used for, the first bead 601 and the second bead 602 may be configured to bind to each other directly, and their direct binding is affected by the concentration of the target analyte. For instance, the first bead 601 may also bind to the target analyte, which in turn competes and inhibits the binding between he first bead 601 and the second bead 602. In other embodiments, particularly in certain non-competitive assays the device may be used for, the first bead 601 and the second bead 602 may be configured to bind to each other indirectly, which is affected by the concentration of the target analyte. For instance, the first bead 601 and the second bead 602 may not be able to bind to each other directly, but they may both be configured to bind to the target analyte but at its different parts, forming a first bead-target analyte-second bead sandwich structure. It is also possible that such a sandwich structure may consist of other molecules or matters in between the first and second beads besides the target analyte. It is yet also possible that the first bead 601 and the second bead 602 may bind to each other through the mediation of other matter(s) than the target analyte, while the target analyte affects such a binding between the mediating matter(s) and the first bead and/or the second bead. In yet other embodiments, the first bead 601 and the second bead 602 may be configured so that they are able to bind to each other both directly and indirectly, and their distance, e.g. whether they bind directly or indirectly, or how many mediators exist in between the indirectly-bound two beads, is affected by the concentration of the target analyte.

The binding between the first bead 601 and the second bead 602 may be configured to bring about a detectable change in the signal related to the bead pair, such as, but not limited to, a luminescence signal, a chromatic signal, an electric signal, a magnetic signal, other forms of signal, or any combination thereof. In other words, the bead pair is configured for a proximity-dependent assay, in which the strength of the bead pair-related signal is proportional to the distance between the first bead and the second bead. In some embodiments, the binding between the first bead and the second bead, hence the proximity between the two, increases the bead pair-related signal. In other embodiments, the binding between the two beads decreases the bead pair-related signal. In some embodiments, the first bead, the second bead, or both are the sources for the bead pair-related signal. In other embodiments, there is an external source that provides the bead pair-related signal, which is regulated by the distance between the first and second beads.

In some embodiments, the first bead 601 may be a donor bead, and the second bead 602 a receptor bead, or vice versa, The donor bead may be excited spontaneously or upon stimulation, and may be configured to, in its excited state, release a converting energy or matter. For instance, the donor bead may comprise a radio-labeled molecule so that the spontaneous decay of its radioactive atoms releases electrons as a converting matter. Or in some cases, the donor bead become excited upon stimulation, like in the presence of an energy (e.g. light, magnetic, or heat stimulation), in the proximity of chemical compounds, or any other stimulation formats. The acceptor bead may be convertible by a certain level of the converting energy or matter and provide a signal in its converted state. The converting energy or matter may dissipate (in terms of its intensity or concentration) or degenerate (in terms of its existence) in a spatiotemporally-regulated manner, so that the acceptor bead may only provide a signal in the proximity of the excited donor bead, and/or in a certain period of time, or that in general the strength of the signal is dependent on the distance between the two beads, and/or the time the two beads are brought into proximity.

In some exemplary embodiments, the bead pair are configured for a luminescence oxygen-channeling assay, in which the donor bead contains photosensitive compounds that upon laser stimulation, releases a metastable species, which triggers a cascade of chemical events in nearby acceptor bead which contains luminescent compound. The cascade of chemical events induced by singlet oxygen results in luminescence emitted by the luminescent compound. Such an oxygen-channeling luminescence effect strictly depends on the distance between the donor and acceptor beads, in that the metastable species can only survive a short distance of travelling. The metastable species include, but not limited to, singlet oxygen, triplet states, dioxetanes, and dioxetane diones. In some exemplary embodiments, the bead pair are configured for a fluorescence resonance energy transfer assay, in which the donor bead contains a donor chromophore, in its excited state, may transfer energy in the form of light to an acceptor chromophore contained in the acceptor bead through nonradiative dipole-dipole coupling. The acceptor chromophore emits light of a different wavelength from that of the light emitted by the donor chromophore. The efficiency of this energy transfer is inversely proportional to the sixth power of the distance between donor and acceptor, making FRET extremely sensitive to small changes in distance. In some other exemplary embodiments, the bead pair are configured for a scintillation proximity assay (SPA), in which the donor bead contains a radio-labeled molecule releasing beta particles while spontaneously decaying, and the acceptor bead contains scintillation compounds that, in proximity of the donor bead, is stimulated by the electrons to emit light signal. The energy the electron possesses dissipates as the electron travels in a medium (e.g. sample), thus it requires the acceptor bead to be in proximity of the donor bead (e.g. be bound to), in order to be excited by a certain level of energy that incurs when the electron hits the acceptor donor bead. In other embodiments, the bead pair may also be configured in other different manners than the three exemplary assay formats, so long as it serves the basis for a proximity-dependent assay.

1.2. Plate Configurations, Reduction of Thickness and Acceleration of Binding

As shown in FIG. 20, the first plate 10 and the second plate 20 are movable relative to each other into different configurations. One of the configurations is an open configuration, as illustrated in panels (A) to (C), in which the first plate 10 and the second plate 20 are partially or completely separated from each other, and the spacing between them is not regulated by the spacing mechanism. Panel (B) shows that in the open configuration, the sample may be deposited on the first plate inner surface 11. It should be noted, however, the sample may be deposited on the second plate inner surface 21, or the inner surfaces of both plates.

Referring now to FIG. 20 panel (C), after the sample deposition, when the two plates are brought together to face each other and contact the sample with their sample contact areas, one or both of the first bead 601 and the second bead 602 may be released into the sample and diffuse in the sample. In some embodiments, as illustrated in panel (C), the second bead 602 is released into the sample, while the first bead 601 remains attached to the first plate binding site 101 (not indicated). In such cases, the first bead 601 may serve as a capture agent that captures and immobilizes the second bead 602 either directly or indirectly. In other embodiments, it may also be configured that the first bead 601 is released into the sample and the second bead 602 is to serve as the capture agent. In yet other embodiments, both the first bead 601 and the second bead 602 may be released into the sample, so that they may both diffuse in the sample.

In some embodiments, the first plate 10, second plate 20, or both may further comprise one or more amplification sites that are each capable of amplifying the bead pair-related signal when the bead pair is in proximity of the amplification site. For instance, the amplification site may amplify the signal when the bead pair in 100 nm or less, 200 nm or less, 500 nm or less, 1 µm or less, 5 µm or less, 20 nm or more, 80 nm or more, 320 nm or less, or 1.5 µm or more, from the amplification site. The binding site may be coated with a layer of noble metallic material, which may provide, among others, a plasmonic effect that enhances the fluorescence signal the bead pair, the analyte, other matters in the sample, and/or the binding site may carry.

Referring now to FIG. 20 panel (D), the plates are brought into another of its configurations, a closed configuration, by a compressing force (F) applied on the outer surfaces of both plates (12 and 22, respectively). In the closed configuration, the spacing 102 between the two plates is regulated by the spacing mechanism; and more importantly, the thickness of a relevant volume of the deposited sample is reduced, compared to that in the open configuration of the plates, into a layer of reduced thickness 904. The term "a relevant volume" as used herein refers to a part or entirety of the deposited sample. The reduced thickness of the layer 904 is confined by the inner surfaces of the plates (11 and 21) and in touch with both binding sites 101 and 201 (not shown), and is regulated by the plates (10 and 20) and the spacing mechanism. Moreover, as shown in the figure, at least one bead pair is in the layer of reduced thickness 904, which allows the diffusion of the second bead 602 and the potential binding between the first bead 601 and the second bead 602.

Reducing the spacing between the two plates 102 (hence the thickness of the relevant volume of the sample 904) may significantly reduce the diffusion distance of the first bead, the second bead, or both, and therefore the time needed for the binding between the first and second beads to reach equilibrium. Consequently, the speed for bio/chemical assays of a liquid sample using the present device can be significantly accelerated. In some embodiments, the spacing mechanism-regulated reduced thickness is 5 mm or less, 1 mm or less, 500 µm or less, 250 µm or less, 150 µm or less, 100 µm or less, 50 µm or less, 1 µm or less, 500 nm or less, 100 nm or less, 50 nm or less, 10 nm or less, 2 nm or more, 5 nm or more, 20 nm or more, 200 nm or more, 2 µm or more, 20 µm or more, 200 µm or more, or 2 mm or more. In some embodiments, the reduced thickness is substantially less than the average linear dimension of the predetermined area of the binding sites.

1.3. Spacing Mechanism and Layer of Uniform Thickness

In some embodiments, the spacing mechanism comprises a plurality of spacers that may be positioned between the first plate 10 and second plate 20 when the plates are in the closed configuration. In some embodiments, the spacers may have a range of different heights, but a maximum height of 5 mm or less, 1 mm or less, 500 µm or less, 250 µm or less, 150 µm or less, 100 µm or less, 50 µm or less, 1 µm or less, 500 nm or less, 100 nm or less, 50 nm or less, 10 nm or less, 2 nm or more, 5 nm or more, 20 nm or more, 200 nm or more, 2 µm or more, 20 µm or more, 200 µm or more, or 2 mm or more. In other embodiments, the spacers may have a predetermined substantially uniform height of 5 mm or less, 1 mm or less, 500 µm or less, 250 µm or less, 100 µm or less, 50 µm or less, 1 µm or less, 500 nm or less, 100 nm or less, 50 nm or less, 10 nm or less, 2 nm or more, 5 nm or more, 20 nm or more, 200 nm or more, 2 µm or more, 20 µm or more, 200 µm or more, or 2 mm or more. In some embodiments, the spacers may be fixed to the inner surface of one or both of the plates. In other embodiments, the spacers may be separate from the plates. In some embodiments, the spacers may have a predetermined constant inter-spacer distance that is 50 nm or more, 100 nm or more, 500 nm or more, 1 µm or more, 5 µm or more, 10 µm or more, 20 µm or more, 50 µm or more, 100 µm or more, 200 µm or more, 500 µm or more, 1 mm or less, 250 µm or less, 150 µm or less, 75 µm or less, 25 µm or less, 15 µm or less, 2 µm or less, 750 nm or less, 250 nm or less, 150 nm or less, 75 nm or less. In other embodiments, the spacers may have irregular inter-spacer distances. In some embodiments, at least one of the spacers is inside the sample contact area. In other embodiments, none of the spacers is inside the sample contact area. In some embodiments, the layer of reduced thickness has a substantially uniform thickness that is about the uniform height of the spacers.

FIG. 21 shows another exemplary embodiment of the device provided by the present invention. The device comprises a first plate 10, a second plate 20, and at least one first bead 601 and at least one second bead 602. Particularly, as shown in panel (A), the second plate 20 comprises a plurality of spacers 40 (not shown in the perspective view) that are fixed on its inner surface 21, and at least one of the spacers is inside the sample contact area (not indicated). It should be noted, however, the spacers 40 may also be fixed on the first plate inner surface 11 (not shown), or both of the first plate and second plate inner surfaces (11 and 21, not shown). In these embodiments, the spacers 40 serve as the spacing mechanism as disclosed above and are a part of the first plate 10, second plate 20, or both accordingly. In some embodiments, the spacers have a highly uniform height, and/or a predetermined constant inter-spacer distance. In the closed configuration of the two plates, as shown in panel (B), the spacing between the two plates 102 is regulated by the plates and the spacers 40. In some embodiments, the spacing 102 may be about equal to the uniform height of the spacers 40, and consequently, the layer of reduced thickness 904 may become a layer of highly uniform thickness and the uniform thickness is about the uniform height of the spacers. As shown in the figure, in this exemplary embodiment, the first bead 601 and the second bead 602 are both released into the sample and diffuse in the sample. Some of the first beads 601 and second beads 602 bind to the target analyte 92 in the sample, forming the first bead-target analyte-second bead sandwich.

In these particular embodiments, the two plates form a part of a compressed regulated open flow (CROF) device or otherwise named QMAX (Q: quantitative, M: multiplexing, A: adding reagents, X: acceleration) device, such as but not limited to the CORF device or QMAX device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

2. Method

Another aspect of the present invention is a method of a method of analyzing a liquid sample. FIG. 22 is a flow chart of an exemplary embodiment of the method. The assay method utilizes the device as disclosed above. As illustrated, the method may comprise:

(a) providing a first plate 10, second plate 20, a spacing mechanism, and at least one first bead 601 and at least one second bead 602, wherein as disclosed above:
  i. the first plate 10 and second plate 20 are movable relative to each other into different configurations;
  ii. each plate respectively comprises an outer surface and an inner surface that has a sample contact area for contacting a liquid sample containing a target analyte;

iii. both of the plates comprise, in a respective sample contact area, one or a plurality of binding sites (101 and 201, respectively) that have a predetermined area;

iv. the first bead 601 and the second bead 602 constitute a bead pair and are configured to bind to each other in a target analyte-related manner, and the binding between the first bead and the second bead is configured to bring about a change in a detectable signal related to the bead pair; and v. the first bead 601 and the second bead 602 are respectively coated on the binding site of one or both of the plates, and one or both of the beads in the bead pair are configured to be, upon contacting the sample, released into the sample and diffuse in the sample;

(b) depositing the liquid sample 90 containing a target analyte 92 on the inner surface of at least one of the two plates when the two plates are configured in an open configuration, in which: the two plates are partially or entirely separated apart and the spacing between the plates is not regulated by the spacing mechanism; and (c) compressing a relevant volume of the deposited sample 90 by bringing the two plates into a closed configuration, in which: the thickness of the relevant volume of the deposited sample is reduced, compared to that in the open configuration of the plates, into a layer of reduced thickness 904 that is confined by the inner surfaces of the plates and in touch with the binding site; the reduced thickness of the layer 904 is regulated by the plates and the spacing mechanism, and is 150 µm or less and substantially less than the average linear dimension of the predetermined area of the binding site; and at least one bead pair is in the layer of reduced thickness, wherein the relevant volume is a portion or an entire volume of the sample; and wherein reducing the thickness of the relevant volume of the sample reduces the time for the binding between the first bead and the second bead to reach equilibrium.

As disclosed, in the closed configuration of the two plates, the reduction of the thickness of the relevant volume of the sample may significantly reduce the time for the binding between the first bead and the second bead to reach equilibrium (termed "saturation time" hereinafter). In some embodiments, the reduced thickness is 5 mm or less, 1 mm or less, 500 µm or less, 250 µm or less, 100 µm or less, 50 µm or less, 1 µm or less, 500 nm or less, 100 nm or less, 50 nm or less, 10 nm or less, 2 nm or more, 5 nm or more, 20 nm or more, 200 nm or more, 2 µm or more, 20 µm or more, 200 µm or more, or 2 mm or more. In other embodiments, the reduced thickness is substantially less than the average linear dimension of the predetermined area of the binding sites.

In some embodiments, the method may further comprise a step of:

(d) after step (c) and while the plates are in the closed configuration, assessing the quantity of the analyte in a part or entirety of the layer of reduced thickness 904, through analyzing the bead pair-related signal, after incubating for a time that is about equal to or longer than the time that it takes for one or both beads of the bead pair to diffuse across the thickness of the layer of reduced thickness 904.

In some embodiments, the step (d) may comprise stopping the incubation after said time, and then assessing the quantity of the analyte in a part or entirety of the layer of reduced thickness 904.

In some embodiments, the signal analyzing in step (d) may comprise measuring the bead pair-related signal such as, but not limited to, (i) luminescence selected from photoluminescence, electroluminescence, and electrochemiluminescence; (ii) light absorption, reflection, transmission, diffraction, scattering, or diffusion; (iii) surface Raman scattering; (iv) electrical impedance selected from resistance, capacitance, and inductance; (v) magnetic relaxivity; (vi) any combination of (i)-(v).

As disclosed above, in some embodiments of the device for analyzing a liquid sample, the spacing mechanism may comprise spacers 40 that are fixed to the first plate 10, the second plate 20, or both, and that the first plate 10 and the second plate 20 may form part of the "CROF device". Correspondingly, in some embodiments, the assay method may comprise:

(a) providing a first plate, a second plate, at least one first bead, and at least one second bead, wherein:

i. the first plate and second plate are movable relative to each other into different configurations;

ii. each plate respectively comprises an outer surface and an inner surface that has a sample contact area for contacting a sample suspected of containing a target analyte;

iii. both of the plates comprise, in a respective sample contact area, one or a plurality of binding sites that have a predetermined area;

iv. one or both of the plates comprise a plurality of spacers that are fixed with the respective inner surface, wherein the spacers have a predetermined substantially uniform height and a predetermined constant inter-spacer distance, and at least one of the spacers is inside the sample contact area, v. the first bead and the second bead constitute a bead pair and are configured to bind to each other in a target analyte-related manner, and the binding between the first bead and the second bead is configured to bring about a change in a detectable signal related to the bead pair; and vi. the first bead and the second bead are respectively coated on the binding site of one or both of the plates, and one or both of the beads in the bead pair are configured to be, upon contacting the sample, released into the sample and diffuse in the sample;

(b) depositing the liquid sample on the inner surface of at least one of the two plates when the two plates are configured in an open configuration, in which: the two plates are partially or entirely separated apart and the spacing between the plates is not regulated by the spacers; and (c) compressing a relevant volume of the deposited sample by bringing the two plates into a closed configuration, in which: the thickness of the relevant volume of the deposited sample is reduced, compared to that in the open configuration of the plates, into a layer of highly uniform thickness that is confined by the inner surfaces of the plates and in touch with the binding sites; the uniform thickness of the layer is regulated by the plates and the spacers, and is 150 µm or less and substantially less than the average linear dimension of the predetermined area of the binding sites; and at least one bead pair is in the layer of uniform thickness, wherein the relevant volume is a portion or an entire volume of the sample; and wherein reducing the thickness of the relevant volume of the sample reduces the time for the binding between the first bead and the second bead to reach equilibrium.

In some embodiments, the method may further comprise a step of:

(d) after step (c) and while the plates are in the closed configuration, assessing the quantity of the analyte in a part or entirety of the layer of uniform thickness, through analyzing the bead pair-related signal, after incubating for a time that is about equal to or longer than the time that it takes for the nanoparticle label to diffuse across the thickness of the uniform thickness layer.

In these embodiments, the configuration of the spacers with substantially uniform height and constant inter-spacer distance and the achievement of a layer of highly uniform thickness with at least part of the deposited sample may provide manifold advantages. Particularly, the uniform thickness of the layer may be about equal to the uniform height of the spacers. In some embodiments, the reduction of sample thickness to the uniform thickness may uniformly reduce the time needed for the binding of the bead pair to reach equilibrium, and accelerate the assay in a uniform manner. In some embodiments, the relevant volume of the layer of uniform thickness may be determined by timing the predetermined uniform height with the lateral area of the relevant volume, therefore, the concentration of the target analyte may be determined, without knowing the exact volume of the sample that is deposited and being analyzed, by dividing the assessed quantity of the target analyte in the layer of uniform thickness by the volume of the uniform thickness layer. In other embodiments, only a part of the relevant volume, in which the target analyte is quantified, may be determined. The volume of said part may be calculated by times the spacer height with the lateral area of said part, which may be calculated based on the number of the spacers in the part and the predetermined spacer height and inter-spacer distance. Accordingly, the concentration of the analyte may be calculated by dividing the quantity of the analyte in said part of the layer of uniform thickness by the volume of said part. In some embodiments, the conformable pressing force may be removed after bringing the two plate into the closed configuration, as the two plates may remain self-held and the thickness of the layer of uniform thickness after removal of the conformable pressing force may be substantially the same as of the layer of uniform thickness before removing the conformable pressing force and deviate from the spacer height by less than 10%. Such configuration may allow for ease to operate the device.

Examples of Present Invention

A1. A device for analyzing a target analyte in a liquid sample, comprising:
  a first plate, a second plate, one first type bead, one second type bead, and a spacing mechanism, wherein:
    v. the first plate and second plate are movable relative to each other into different configurations, including an open configuration and a closed configuration;
    vi. each plate comprises, on its respective inner surface, a sample contact area for contacting a liquid sample that contains a target analyte;
    vii. the spacing mechanism is configured to regulate the spacing between the first plate and the second plate in the closed configuration;
    viii. in the open configuration, the first type bead is attached to the sample contact area of the first plate, and the second type bead is attached to the sample contact area of the second plate, wherein one or both of the attached first type bead and second type bead are released and diffuse in the sample after the sample contacts the beads; and
    ix. the first type bead and the second type bead are configured to bind specifically to each other either directly or indirectly;
      wherein in the direct binding, the first type bead is configured to specifically bind to the target analyte, which competitively inhibits the binding between the first type bead and the second type bead;
      wherein in the indirect binding, the first type bead and the second type bead are configured to specifically bind to the target analyte at different locations, forming the indirect binding through mediation of the target analyte;
      wherein in the open configuration: the two plates are partially or entirely separated apart and the spacing between the plates is not regulated by the spacing mechanism;
      wherein in the closed configuration: the thickness of a relevant volume of the deposited sample is reduced, compared to that in the open configuration of the plates, into a layer of reduced thickness that is confined by the inner surfaces of the plates, regulated by the plates and the spacing mechanism, and is 150 µm or less; and at least one first type bead and at least one second type bead are in the layer of reduced thickness; and
      wherein the relevant volume is a portion or an entire volume of the sample.

A2. The device of embodiment A1, wherein the binding between the first type bead and the second type bead is configured to bring about a signal.

A3. The device of embodiment A1, wherein the binding between the first type bead and the second type bead is configured to bring about an increase or decrease in a signal provided by the first type bead and/or the second type bead.

A4. The device of any one of embodiment A2 or A3, wherein the signal is:
  i. luminescence selected from photoluminescence, electroluminescence, and electrochemiluminescence;
  ii. light absorption, reflection, transmission, diffraction, scattering, or diffusion;
  iii. surface Raman scattering;
  iv. electrical impedance selected from resistance, capacitance, and inductance;
  v. magnetic relaxivity; or
  vi. any combination of i-v.

A5. The device of any one of prior embodiments, wherein the first type bead and the second type bead are configured for a luminescence oxygen-channeling assay, in which:
  i. the first type bead comprises a photosensitizer, wherein the photosensitizer is capable, in its excited state, of releasing an intrinsically metastable species;

ii. the second type bead comprises a chemiluminescent compound capable of chemiluminescence upon reaction with the intrinsically metastable species; and
iii. the binding between the first type bead and the second type bead enables the reaction between the chemiluminescent compound of the second type bead and the metastable species released from the first type bead.

A6. The device of embodiment A5, wherein the metastable species is selected from the group consisting of: singlet oxygen, triplet states, dioxetanes, and dioxetane diones.

A7. The device of any one of prior embodiments, wherein the first type bead and the second type bead are configured for a fluorescence resonance energy transfer assay, in which:
 i. the first type bead comprises a donor chromophore capable of, in its excited state, emitting an exciting light;
 ii. the second type bead comprises an acceptor chromophore capable of, upon stimulation by the exciting light, emitting an excited light of a different wavelength from that of the exciting light.
 iii. the binding between the first type bead and the second type bead enables the stimulation of the acceptor chromophore of the second type bead by the exciting light emitted from the first type bead.

A8. The device of any one of prior embodiments, wherein the first type bead and the second type bead are configured for a scintillation proximity assay, in which:
 i. the first type bead comprises a radio-labeled molecule capable of releasing beta particles spontaneously;
 ii. the second type bead comprises scintillation compounds that, in proximity of the donor bead, is stimulated by the beat particles to emit a light.
 iii. the binding between the first type bead and the second type bead enables the stimulation of the scintillation compounds of the second type bead by the beta particles released from the first type bead.

A9. The device of any one of prior embodiments, wherein the spacing mechanism comprises a plurality of spacers and in the closed configuration the spacers are positioned between the inner surfaces of the two plates.

A10. The device of embodiment A9, wherein the spacers have a maximum height of 150 µm or less.

A11. The device of embodiment A9, wherein the spacers have a predetermined substantially uniform height that is 150 µm or less.

A12. The device of any one of embodiments A9-A11, wherein the spacers have a predetermined constant inter-spacer distance.

A13. The device of any one of embodiments A9-A12, wherein the spacers are fixed with the respective inner surface of one or both of the plates.

A14. The device of any one of embodiments A9-A13, wherein at least one of the spacers is inside the sample contact area.

A15. The device of any one of embodiments A9-A14, wherein the layer of reduced thickness has a substantially uniform thickness that is about the uniform height of the spacers.

B1. A device for analyzing a liquid sample, comprising: a first plate, a second plate, one first type bead, and one second type bead, wherein:
 i. the first plate and second plate are movable relative to each other into different configurations, including an open configuration and a closed configuration;
 ii. each plate comprises, on its respective inner surface, a sample contact area for contacting a liquid sample that contains a target analyte;
 iii. one or both of the plates comprise a plurality of spacers that are fixed with the inner surface, wherein the spacers have a predetermined substantially uniform height and a predetermined constant inter-spacer distance, and at least one of the spacers is inside the sample contact area,
 iv. in the open configuration, the first type bead is attached to the sample contact area of the first plate, and the second type bead is attached to the sample contact area of the second plate, wherein one or both of the attached first type bead and second type bead are released and diffuse in the sample after the sample contacts the beads; and
 v. the first type bead and the second type bead are configured to bind specifically to each other either directly or indirectly;
 wherein in the direct binding, the first type bead is configured to specifically bind the target analyte, which competitively inhibits the binding between the first type bead and the second type bead;
 wherein in the indirect binding mode, the first type bead and the second type bead are configured to specifically bind to the target analyte at different locations, forming the indirect binding through mediation of the target analyte;
 wherein in the open configuration: the two plates are partially or entirely separated apart and the spacing between the plates is not regulated by the spacers;
 wherein in the closed configuration: the thickness of a relevant volume of the deposited sample is reduced, compared to that in the open configuration of the plates, into a layer of substantially uniform thickness that is confined by the inner surfaces of the plates, regulated by the plates and the spacers, and is 150 µm or less; and at least one first type bead and at least one second type bead are in the layer of reduced thickness; and
 wherein the relevant volume is a portion or an entire volume of the sample.

C1. A method of analyzing a liquid sample, comprising the steps of:
 (f) providing a first plate, a second plate, one first type bead, one second type bead, and a spacing mechanism, wherein:
  v. the first plate and second plate are movable relative to each other into different configurations, including an open configuration and a closed configuration;
  vi. each plate comprises, on its respective inner surface, a sample contact area for contacting a liquid sample that contains a target analyte;
  vii. the spacing mechanism is configured to regulate the spacing between the first plate and the second plate in the closed configuration;
  viii. in the open configuration, the first type bead is attached to the sample contact area of the first plate, and the second type bead is attached to the sample contact area of the second plate, wherein one or both of the attached first type bead and second type bead are released and diffuse in the sample after the sample contacts the beads; and
  ix. the first type bead and the second type bead are configured to bind specifically to each either directly or indirectly;

x. wherein in the direct binding, the first type bead is configured to specifically bind the target analyte, which competitively inhibits the binding between the first type bead and the second type bead;

xi. wherein in the indirect binding, the first type bead and the second type bead are configured to specifically bind to the target analyte at different locations thereof, forming the indirect binding through mediation of the target analyte;

(g) depositing the liquid sample on the inner surface of at least one of the two plates when the two plates are configured in the open configuration, in which: the two plates are partially or entirely separated apart and the spacing between the plates is not regulated by the spacing mechanism; and (h) compressing a relevant volume of the deposited sample by bringing the two plates into the closed configuration, in which: the thickness of the relevant volume of the deposited sample is reduced, compared to that in the open configuration of the plates, into a layer of reduced thickness that is confined by the inner surfaces of the plates, regulated by the plates and the spacing mechanism, and is 150 µm or less; and at least one first type bead and at least one second type bead is in the layer of reduced thickness, wherein the relevant volume is a portion or an entire volume of the sample; and wherein reducing the thickness of the relevant volume of the sample reduces the time for the binding between the first type bead and the second type bead to reach equilibrium.

C2. The method of embodiment C1, further comprising:
(i) after step (c) and while the plates are in the closed configuration, assessing the quantity of the target analyte in a part or entirety of the layer of reduced thickness, through analyzing a signal related to the binding between the first type bead and the second type bead, after incubating for a time that is about equal to or longer than the time that it takes for the first type bead and/or the second type bead to diffuse across the thickness of the layer of reduced thickness, wherein the signal is brought about or changed by the binding between the first type bead and the second type bead.

C3. The method of embodiment C2, wherein the signal is:
i. luminescence selected from photoluminescence, electroluminescence, and electrochemiluminescence;
ii. light absorption, reflection, transmission, diffraction, scattering, or diffusion;
iii. surface Raman scattering;
iv. electrical impedance selected from resistance, capacitance, and inductance;
v. magnetic relaxivity; or
vi. any combination of i-v.

C4. The method of any one of prior embodiments, wherein the first type bead and the second type bead are configured for a luminescence oxygen-channeling assay, in which:
i. the first type bead comprises a photosensitizer, wherein the photosensitizer is capable, in its excited state, of releasing an intrinsically metastable species;
ii. the second type bead comprises a chemiluminescent compound capable of chemiluminescence upon reaction with the intrinsically metastable species; and iii. the binding between the first type bead and the second type bead enables the reaction between the chemiluminescent compound of the second type bead and the metastable species released from the first type bead.

C5. The method of embodiment C4, wherein the metastable species is selected from the group consisting of: singlet oxygen, triplet states, dioxetanes, and dioxetane diones.

C6. The method of any one of prior embodiments, wherein the first type bead and the second type bead are configured for a fluorescence resonance energy transfer assay, in which:
i. the first type bead comprises a donor chromophore capable of, in its excited state, emitting an exciting light;
ii. the second type bead comprises an acceptor chromophore capable of, upon stimulation by the exciting light, emitting an excited light of a different wavelength from that of the exciting light.
iii. the binding between the first type bead and the second type bead enables the stimulation of the acceptor chromophore of the second type bead by the exciting light emitted from the first type bead.

C7. The method of any one of prior embodiments, wherein the first type bead and the second type bead are configured for a scintillation proximity assay, in which:
i. the first type bead comprises a radio-labeled molecule capable of releasing beta particles spontaneously;
ii. the second type bead comprises scintillation compounds that, in proximity of the donor bead, is stimulated by the beat particles to emit a light.
iii. the binding between the first type bead and the second type bead enables the stimulation of the scintillation compounds of the second type bead by the beta particles released from the first type bead.

C8. The method of any one of prior embodiments, wherein the spacing mechanism comprises a plurality of spacers and the spacers are positioned between the inner surfaces of the two plates in the closed configuration.

C9. The method of embodiment C8, wherein the spacers have a maximum height of 150 µm or less.

C10. The method of embodiment C8, wherein the spacers have a predetermined substantially uniform height that is 150 µm or less.

C11. The method of any one of embodiments C8-C10, wherein the spacers have a predetermined constant inter-spacer distance.

C12. The method of any one of embodiments C8-C11, wherein the spacers are fixed with the inner surface of one or both of the plates.

C13. The method of any one of embodiments C8-C12, wherein at least one of the spacers is inside the sample contact area.

C14. The method of any one of embodiments C8-C13, wherein the layer of reduced thickness has a substantially uniform thickness that is about the uniform height of the spacers.

D1. A method of analyzing a liquid sample, comprising the steps of:
(d) providing a first plate, a second plate, one first type bead, and one second type bead, wherein:
vii. the first plate and second plate are movable relative to each other into different configurations, including an open configuration and a closed configuration;

viii. each plate comprises, on its respective inner surface, a sample contact area for contacting a liquid sample that contains a target analyte;

ix. one or both of the plates comprise a plurality of spacers that are fixed with the inner surface, wherein the spacers have a predetermined substantially uniform height and a predetermined constant inter-spacer distance, and at least one of the spacers is inside the sample contact area, x. in the open configuration, the first type bead is attached to the sample contact area of the first plate, and the second type bead is attached to the sample contact area of the second plate, wherein one or both of the attached first type bead and second type bead are released and diffuse in the sample after the sample contacts the beads; and xi. the first type bead and the second type bead are configured to bind specifically to each either directly or indirectly, wherein in the direct binding, the first type bead is configured to specifically bind the target analyte, which competitively inhibits the binding between the first type bead and the second type bead; and wherein in the indirect binding, the first type bead and the second type bead are configured to specifically bind to the target analyte at different locations, forming the indirect binding through mediation of the target analyte;

(e) depositing the liquid sample on the inner surface of at least one of the two plates when the two plates are configured in an open configuration, in which: the two plates are partially or entirely separated apart and the spacing between the plates is not regulated by the spacers; and (f) compressing a relevant volume of the deposited sample by bringing the two plates into a closed configuration, in which: the thickness of the relevant volume of the deposited sample is reduced, compared to that in the open configuration of the plates, into a layer of highly uniform thickness that is confined by the inner surfaces of the plates, regulated by the plates and the spacers, and is 150 µm or less; and at least one first type bead and at least one second type bead are in the layer of uniform thickness, wherein the relevant volume is a portion or an entire volume of the sample; and wherein reducing the thickness of the relevant volume of the sample reduces the time for the binding between the first type bead and the second type bead to reach equilibrium.

D2. The method of embodiment D1, wherein the compressing in step (c) comprises:

bringing the two plates together; and conformable pressing, either in parallel or sequentially, an area of at least one of the plates to press the plates together to the closed configuration, wherein the conformable pressing generates a substantially uniform pressure on the plates over the relevant volume of the sample, and the pressing spreads the relevant volume of the sample laterally between the sample contact surfaces of the plates.

D3. The method of any one of embodiment D1 or D2, further comprising:

(d) after step (c) and while the plates are in the closed configuration, assessing the quantity of the target analyte in a part or entirety of the layer of uniform thickness, through analyzing a signal related to the binding between the first type bead and/or the second type bead, after incubating for a time that is about equal to or longer than the time that it takes for the first type bead and/or the second type bead to diffuse across the thickness of the uniform thickness layer, wherein the signal is brought about or changed by the binding between the first type bead and the second type bead.

D4. The method of embodiment D3, further comprising a step after step (c) and before step (d): after the plates are in the closed configuration, removing the conformable pressing force, wherein the thickness of the layer of uniform thickness after removal of the conformable pressing force: (i) is substantially the same as of the layer of uniform thickness before removing the conformable pressing force and (ii) deviates from the spacer height by less than 10%.

D5. The method of any one of embodiments D1-D4, wherein during the deposition of step (c), the amount of the sample deposited on the plate is unknown.

E1. The method of any one of prior method embodiments, wherein step (d) comprises: stopping the incubation after said time, and then assessing the quantity of the target analyte in a part or entirety of the layer of uniform thickness.

E2. The method of any one of prior method embodiments, wherein during step (c), the conformable pressing is performed by human hand.

E3. The method of any one of prior method embodiments, wherein the conformable pressing of step (c) is provided by a pressured liquid, a pressed gas, or a conformal material.

E4. The method of any one of prior method embodiments, further comprising one or more washing steps.

E5. The method of any one of prior method embodiments, wherein the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

(4) E6. The method of any one of prior embodiments, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

(5)

(6) E7. The method of any one of prior embodiments, wherein the sample is an environmental gaseous sample from a source selected from the group consisting of: the air, underwater heat vents, industrial exhaust, vehicular exhaust, and any combination thereof.

(7)

(8) E8. The method of any one of prior embodiments, wherein the sample is a foodstuff sample selected from the group consisting of: raw ingredients, cooked food, plant and animal sources of food, preprocessed food, and partially or fully processed food, and any combination thereof.

F1. The device or method of any one of prior embodiments, wherein the time for the binding between the first type bead and the second type bead to reach equilibrium is about equal to or less than 60 seconds.

F2. The device or method of any one of prior embodiments, wherein one or both plates comprise one or a plurality of amplification sites that are each capable of amplifying the signal when the bound first type bead and second type bead are within 500 nm from an amplification site.

F3. The device or method of any one of prior embodiments, wherein the first type bead and the second type bead respectively comprise an affinity binding agent selected from the group consisting of: protein, peptide, peptidomimetics, streptavidin, biotin, oligonucleotide, oligonucleotide mimetics, any other affinity ligand and any combination thereof.

F4. The device or method of any one of prior embodiments, wherein only one of the first type bead and the second type bead is configured to be, upon contacting the sample, released into the sample and diffuse in the sample, while the other bead of the two is configured to remain attached to the respective inner surface upon contacting the sample.

F5. The device or method of any one of prior embodiments, wherein both the first type bead and the second type bead are configured to be, upon contacting the sample, released into the sample and diffuse in the sample.

F6. The device or method of any one of prior embodiments, wherein the first type bead and the second type bead respectively comprise a nanoparticle that has a broadest dimension in the range of 1 nm to 5 μm.

F7. The device or method of any one of prior embodiments, wherein the first type bead and the second type bead respectively comprise a nanoparticle that has a broadest dimension in the range of 1 nm to 500 nm.

F8. The device or method of any one of prior embodiments, wherein the first type bead and the second type bead respectively comprise a nanoparticle that is selected from the group consisting of: carbon nanotubes, fullerenes, dendrimers, quantum dots, noble metal nanoparticles, fluorophore-doped nanoparticles, rare earth-doped nanoparticles, superparamagnetic nanoparticles, and any combination thereof.

F9. The device or method of any one of prior embodiments, wherein the plates have a thickness of less than 200 μm.

F10. The device or method of any one of prior embodiments, wherein the plates have a thickness of less than 100 μm.

F11. The device or method of any one of prior embodiments, wherein each of the plates has an area of less than 5 cm$^2$.

F12. The device or method of any one of prior embodiments, wherein each of the plates has an area of less than 2 cm$^2$.

F13. The device or method of any one of prior embodiments, wherein at least one of the plates is partially or entirely transparent.

F14. The device or method of any one of prior embodiments, wherein at least one of the plates is made from a flexible polymer.

F15. The device or method of any one of prior embodiments, wherein at least one of the plates is a flexible plate, and the thickness of the flexible plate times the Young's modulus of the flexible plate is in the range of 60 to 75 GPa-μm.

F16. The device or method of any one of prior embodiments, wherein the uniform height of the pillars is in the range of 0.5 to 100 μm.

F17. The device or method of any one of prior embodiments, wherein the uniform height is in the range of 0.5 to 20 μm.

F18. The device or method of any one of prior embodiments, wherein the constant inter-spacer distance of the pillars is in the range of 7 to 50 μm.

F19. The device or method of any one of prior embodiments, wherein the constant inter-spacer distance of the pillars is in the range of 5 to 200 μm.

F20. The device or method of any one of prior embodiments, wherein the spacers are pillars with a cross sectional shape selected from round, polygonal, circular, square, rectangular, oval, elliptical, or any combination of the same.

F21. The device or method of any one of prior embodiments, wherein the spacers have a pillar shape and a substantially flat top surface, wherein, for each spacer, the ratio of the lateral dimension of the spacer to its height is at least 1.

F22. The device or method of any one of prior embodiments, wherein each spacer has the ratio of the lateral dimension of the spacer to its height is at least 1.

F23. The device or method of any one of prior embodiments, wherein the minimum lateral dimension of spacer is less than or substantially equal to the minimum dimension of a target analyte in the sample.

F24. The device or method of any one of prior embodiments, wherein the spacers have a pillar shape, and the sidewall corners of the spacers have a round shape with a radius of curvature at least 1 μm.

F25. The device or method of any one of prior embodiments, wherein the spacers have a density of at least 100/mm$^2$.

F26. The device or method of any one of prior embodiments, wherein the spacers have a density of at least 1000/mm$^2$.

F27. The device or method of any one of prior embodiments, wherein the spacers have a filling factor of at least 1%, wherein the filling factor is the ratio of the spacer area in contact with the layer of uniform thickness to the total plate area in contact with the layer of uniform thickness.

F28. The device or method of any one of prior embodiments, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

F29. The device or method of any one of prior embodiments, wherein
at least one of the plates is flexible, and
for the flexible plate, the fourth power of the inter-spacer-distance (ISD) divided by the thickness of the flexible plate (h) and the Young's modulus (E) of the flexible plate, ISD$^4$/(hE), is equal to or less than 106 um$^3$/GPa.

F30. The device or method of any one of prior embodiments, wherein the spacers are fixed on a plate by directly embossing the plate or injection molding of the plate.

F31. The device or method of any one of prior embodiments, wherein the materials of the plate and the spacers are independently selected from polystyrene, PMMG, PC, COC, COP, or another plastic.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels

The devices, systems, and methods herein disclosed can employ various types of labels that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A device for performing a competitive assay, comprising:
   a first plate, a second plate, spacers, a binding site, and a competitive agent, wherein:
   (a) the first plate and the second plate are movable relative to each other into different configurations, wherein each of the plates has a sample contact area for contacting a sample that contains or is suspected of containing a target analyte;
   (b) one or both of the sample contact areas has the binding site, wherein the binding site comprises an immobilized capture agent that binds a target analyte in a sample;

(c) the competitive agent that is capable of, upon contacting the sample, diffusing in the sample, wherein the competitive agent competes with the analyte for binding to the capture agent at the binding site;

wherein the spacers have a predetermined height of and has an average thickness in a range of 0.01 to 200 µm;

wherein at least one of the spacers is located inside one of the sample contact areas, and the spacers have a predetermined inter-spacer distance (ISD);

wherein at least one of the first and second plates is a flexible plate, the flexible plate having a thickness and Young's modulus, and a fourth power of the ISD divided by the thickness of the flexible plate (h) and the Young's modulus (E) of the flexible plate, $ISD^4/(hE)$ is equal to or less than $10^6$ µm$^3$/GPa, and the thickness of the flexible plate times the Young's modulus of the flexible plate is in a range of 60 to 750 GPa-µm, wherein one of the configurations is an open configuration; in the open configuration, the first and second plates are partially or entirely separated apart so that a spacing between the sample contact areas of the first and second plates is larger than 300 µm; and wherein another configuration is a closed configuration; in the closed configuration, the first and second plates are operable to compress the sample into a layer of substantially uniform thickness regulated by the spacers, and the spacing between the sample contact areas of the first and second plates is 200 µm or less.

2. The device of claim 1, wherein one of the plates further comprising a storage site.

3. The device of claim 2, wherein the storage site further comprises another reagent, in addition to the competitive agent.

4. The device of claim 2, wherein the storage site further stores a detection agent, a releasing agent that frees 25OH Vitamin D from the binding site.

5. The device of claim 1, wherein the binding site comprises, in addition to the immobilized capture agent, another reagent that is, upon contacting the sample, capable of diffusion in the sample.

6. The device of claim 1, wherein the first plate comprises a plurality of binding sites and the second plate comprises a plurality of corresponding storage sites.

7. The device of claim 1, wherein one of the plates further comprising a storage site that comprises the competitive agent.

8. The device of claim 1, wherein the capture agent at the binding site is on an amplification surface that is on the one or both sample contact areas, the amplification surface amplifies an optical signal of the analytes or the captured competitive agents.

9. The device of claim 1, wherein the target analyte is 25OH Vitamin D.

10. The device of claim 9, wherein the capture agent is an antibody that specifically binds to 25OH Vitamin D.

11. The device of claim 1, wherein the capture agent specifically binds to free 25OH Vitamin D.

12. A system for analyzing a sample comprising:
(a) the device of claim 1;
(b) a reading device for producing an image of signals emanating from the binding site of the second plate;
(c) a device assembly that operably connects the reading device to the closed configuration of the first plate and second plate;
(d) a memory for storing said image; and
(e) programming for identifying and counting individual binding events as nanoparticles in an area of the image.

13. The device of claim 1, wherein the sample contact area in the first plate further comprises a reagent storage site, wherein the reagent storage site stores a reagent and is not in the same location of the sample contact area as that of the binding site.

14. The device of claim 1, wherein the competitive agent comprises a label.

15. The device of claim 14, wherein the label is a nanoparticle label, and wherein a time for the binding between the capture agent and the nanoparticle label to reach equilibrium is about equal to or less than 60 seconds.

16. The device of claim 1, wherein the binding site is between a pair of electrodes.

17. The device of claim 1, wherein the spacers are pillars and have a height in the range of 0.5 to 100 µM.

18. The device of claim 1, wherein the inter-spacer distance is in the range of 7 to 80 µm.

19. The device of claim 1, wherein the spacers are pillars, and the inter-spacer distance of the pillars is in the range of 5 to 200 µm.

20. The device of claim 1, wherein the spacers are pillars with a cross sectional shape selected from round, polygonal, circular, square, rectangular, oval, elliptical, or any combination of the same.

21. The device of claim 1, wherein each of the spacers has a pillar shape and a flat top surface, wherein, for each spacer, a ratio of the lateral dimension of the spacer to its height is at least 1.

22. The device of claim 1, wherein the spacers have a filling factor of at least 1%, wherein the filling factor is a ratio of spacer area to the total area.

23. The device of claim 1, wherein the Young's modulus of the spacers times a filling factor of the spacers is equal or larger than 10 MPa, and the filling factor is a ratio of the spacer area in contact with the layer of uniform thickness to the total plate area.

24. The device of claim 1, wherein the spacers have a filling factor of at least 2.3%, wherein the filling factor is a ratio of spacer area to the total area.

25. A method for performing a competitive assay, comprising:
(a) providing the device of claim 1;
(b) providing, on one or both of the sample contact areas, a binding site, wherein the binding site comprises immobilized capture agent that binds the target analyte;
(c) providing a competitive agent that is capable of, upon contacting the sample, diffusing in the sample, wherein the competitive agent competes with the target analyte for binding to the capture agents at the binding site;
(d) depositing, in the open configuration, the sample on one or both of the sample contact areas, wherein in the open configuration;
(e) after (c), bringing the first and second plates to the closed configuration, wherein, in the closed configuration, at least part of the sample deposited in (c) is confined between the sample contact areas of the first and second plates to form the layer of substantial uniform thickness; and
(f) detecting a signal from (i) the competitive agent that is captured by the binding site, (ii) an analyte that is captured by the binding site, or (iii) both (i) and (ii).

26. The method of claim 25, wherein the binding site comprises, in addition to immobilized capture agent, another reagent that is, upon contacting the sample, capable of diffusion in the sample.

27. The method of claim 25, wherein one of the plates further comprising a storage site that comprises the competitive agent.

28. The method of claim 25, wherein the first plate comprises a plurality of binding sites and the second plate comprises a plurality of corresponding storage sites.

29. The method of claim 25, wherein the capture agents at the binding site are on an amplification surface that amplifies an optical signal of the analytes or the captured competitive agents.

30. The method of claim 25, wherein the detection of the signal is electrical, optical, or both.

31. The method of claim 25, wherein the target analyte is 25OH vitamin D.

32. The method of claim 25, wherein the sample is a blood sample (whole blood, plasma, or serum).

33. The method of claim 25, wherein the step (f) of detecting is performed without washing.

34. The method of claim 25, further comprising a step of washing, wherein the washing is conducted by squeezing a sponge to release the wash solution onto the inner surface of the first plate and releasing the sponge to reabsorb the wash solution.

35. The method of claim 25, wherein the sample contact area in the first plate further comprises a reagent storage site, wherein the reagent storage site stores a reagent and is not in the same location of the sample contact area as that of the binding site.

36. The method of claim 25, wherein the competitive agent comprises a label.

37. The method of claim 36, wherein the label is a nanoparticle label, and wherein the time for the binding between the binding agent and the nanoparticle label to reach equilibrium is about equal to or less than 60 seconds.

38. The method of claim 25, wherein the target analyte is a protein, peptide, DNA, RNA, nucleic acid, small molecule, cell, or nanoparticle.

39. The method of claim 25, wherein the signals are luminescence signals selected from the group consisting of fluorescence, electroluminescence, chemiluminescence, and electrochemiluminescence signals.

40. The method of claim 25, wherein the liquid sample is made from a biological sample selected from amniotic fluid, aqueous humour, vitreous humour, whole blood, fractionated blood, plasma, serum, breast milk, cerebrospinal fluid (CSF), cerumen (earwax), chyle, chime, endolymph, perilymph, feces, breath, gastric acid, gastric juice, lymph, mucus, pericardial fluid, peritoneal fluid, pleural fluid, pus, rheum, saliva, exhaled breath condensates, sebum, sputum, sweat, synovial fluid, tears, vomit, and urine.

41. The method of claim 25, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

42. The method of claim 25, wherein the sample is an environmental gaseous sample from a source selected from the group consisting of: the air, underwater heat vents, industrial exhaust, vehicular exhaust, and any combination thereof.

43. The method of claim 25, wherein the sample is a foodstuff sample selected from the group consisting of: raw ingredients, cooked food, plant and animal sources of food, preprocessed food, and partially or fully processed food, and any combination thereof.

44. The method of claim 25, wherein the spacers are pillars having a height in the range of 0.5 to 100 μm.

45. The method of claim 25, wherein the spacers are pillars, and the inter-spacer distance of the pillars is in the range of 5 to 200 μm.

46. The method of claim 25, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

* * * * *